(12) United States Patent
Saitoh et al.

(10) Patent No.: US 7,387,845 B2
(45) Date of Patent: Jun. 17, 2008

(54) MONOAMINO COMPOUND AND ORGANIC LUMINESCENCE DEVICE USING THE SAME

(75) Inventors: Akihito Saitoh, Yokohama (JP); Mizuho Hiraoka, Kawasaki (JP); Akihiro Senoo, Kawasaki (JP); Hiroshi Tanabe, Yokohama (JP); Naoki Yamada, Inaqi (JP); Chika Negishi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 428 days.

(21) Appl. No.: 10/525,622

(22) PCT Filed: Aug. 25, 2003

(86) PCT No.: PCT/JP03/10700

§ 371 (c)(1),
(2), (4) Date: Feb. 25, 2005

(87) PCT Pub. No.: WO2004/020388

PCT Pub. Date: Mar. 11, 2004

(65) Prior Publication Data

US 2005/0244670 A1 Nov. 3, 2005

(30) Foreign Application Priority Data

Aug. 28, 2002 (JP) ............................... 2002-248745

(51) Int. Cl.
*H05B 33/14* (2006.01)
(52) U.S. Cl. .................. 428/690; 428/917; 313/504; 313/506
(58) Field of Classification Search .................. 546/98; 548/445; 564/426, 427, 428, 433; 428/690, 428/917; 313/504, 506
See application file for complete search history.

(56) References Cited

U.S. PATENT DOCUMENTS

| | | | |
|---|---|---|---|
| 4,539,507 A | 9/1985 | Van Slyke et al. | 313/504 |
| 4,720,432 A | 1/1988 | Van Slyke et al. | 428/457 |
| 4,885,211 A | 12/1989 | Tang et al. | 428/457 |
| 5,130,603 A | 7/1992 | Tokailin et al. | 313/504 |
| 5,151,629 A | 9/1992 | Van Slyke et al. | 313/504 |
| 5,227,252 A | 7/1993 | Murayama et al. | 428/690 |
| 5,247,190 A | 9/1993 | Friend et al. | 257/40 |
| 5,317,169 A | 5/1994 | Nakano et al. | 257/40 |
| 5,382,477 A | 1/1995 | Saito et al. | 428/690 |
| 5,409,783 A | 4/1995 | Tang et al. | 428/690 |
| 5,422,210 A | 6/1995 | Maruyama et al. | 430/59 |
| 5,514,878 A | 5/1996 | Holmes et al. | 257/40 |
| 5,672,678 A | 9/1997 | Holmes et al. | 528/373 |
| 5,726,457 A | 3/1998 | Nakano et al. | 257/40 |
| 5,900,327 A | 5/1999 | Pei et al. | 428/690 |
| 5,989,737 A | 11/1999 | Xie et al. | 428/690 |
| 6,093,864 A | 7/2000 | Tokailin et al. | 585/25 |
| 6,387,545 B1 | 5/2002 | Liu et al. | 428/690 |
| 6,743,948 B1 | 6/2004 | Hosokawa et al. | 564/426 |
| 2003/0065190 A1 | 4/2003 | Spreitzer et al. | 548/134 |
| 2003/0072966 A1 | 4/2003 | Hosokawa et al. | 428/690 |
| 2003/0232216 A1 | 12/2003 | Saitoh et al. | 428/690 |
| 2004/0253389 A1 | 12/2004 | Suzuki et al. | 428/1.1 |
| 2004/0263067 A1 | 12/2004 | Saitoh et al. | 313/504 |
| 2004/0265632 A1 | 12/2004 | Okinaka et al. | 428/690 |
| 2005/0038296 A1 | 2/2005 | Hosokawa et al. | 564/426 |
| 2005/0099115 A1 | 5/2005 | Saitoh et al. | 314/504 |
| 2005/0106414 A1 | 5/2005 | Saitoh et al. | 428/690 |

FOREIGN PATENT DOCUMENTS

| | | |
|---|---|---|
| EP | 504794 A1 | 3/1992 |
| EP | 0918259 A2 | 10/1998 |
| JP | 62-195667 | * 8/1987 |
| JP | 1-278789 | 11/1989 |
| JP | 2-190862 | 7/1990 |
| JP | 02-247278 | 10/1990 |
| JP | 03-249759 | * 11/1991 |
| JP | 03-255190 | 11/1991 |
| JP | 04-145192 | 5/1992 |
| JP | 4-276760 | 10/1992 |
| JP | 5-100464 | 4/1993 |
| JP | 05-202356 | 8/1993 |
| JP | 05-247460 | 9/1993 |
| JP | 09-202878 | 8/1997 |
| JP | 09-227576 | 9/1997 |
| JP | 10-255985 | 9/1998 |
| JP | 11-184108 | 7/1999 |
| JP | 11-312587 | 11/1999 |

(Continued)

OTHER PUBLICATIONS

Tang, et al; "Organic Electroluminescent Devices"; Appl. Phys. Lett. vol. 51, No. 12, pp. 913-915 (1987).

(Continued)

*Primary Examiner*—Fiona T Powers
(74) *Attorney, Agent, or Firm*—Fitzpatrick, Cella, Harper & Scinto

(57) ABSTRACT

A novel monoamino compound is provided. Using the monoamino compound, an organic luminescence device is provided, which exhibits a luminescence hue with extremely high purity, and having an optical output of a high luminance with a high efficiency and a long life time. The monoamino compound is represented by the following general formula [1]

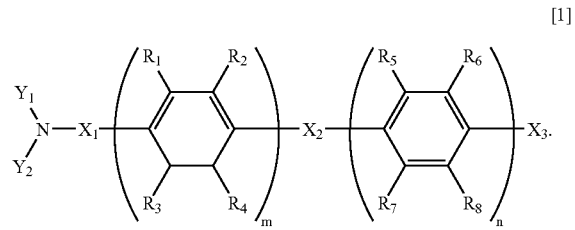

10 Claims, 3 Drawing Sheets

FOREIGN PATENT DOCUMENTS

| | | | |
|---|---|---|---|
| JP | 2002-8866 | | 1/2000 |
| JP | 2000-5069166 | | 6/2000 |
| JP | 2000-247932 | * | 9/2000 |
| JP | 2000-273056 | | 10/2000 |
| JP | 2001-052868 | | 2/2001 |
| JP | 2001-192651 | | 7/2001 |
| JP | 2002-502889 | | 1/2002 |
| JP | 2002-503037 | | 1/2002 |
| WO | WO 97/33323 | | 9/1997 |
| WO | WO 99/40051 | | 8/1999 |
| WO | WO 99/40655 | | 8/1999 |

OTHER PUBLICATIONS

Burroughes, et al; Light-emitting diodes based on conjugated polymers; Nature, vol. 347, pp. 539-541 (1990).

Kawai et al., Formation of Intramolecular Exciplexes in Electrogenated Chemiluminescence, J. Phys. Chem, 84, 2368-2374.

* cited by examiner

MONOAMINO COMPOUND AND ORGANIC LUMINESCENCE DEVICE USING THE SAME

TECHNICAL FIELD

The present invention relates to a monoamino compound and an organic luminescence device, and more particularly to a device that emits light by applying an electric filed on a thin film made of an organic compound.

BACKGROUND ART

An organic luminescence device is a device where a thin film including a fluorescent organic compound is sandwiched between an anode and a cathode, an electron and a hole are injected from the respective electrodes to generate an exciton of the fluorescent compound, and light which is emitted when the exciton returns to the ground state is utilized.

According to the study of Kodak company in 1987 (Appl. Phys. Lett. 51, 913 (1987)), there has been reported a luminescence with approximately 1000 cd/m$^2$ at an applied voltage of approximately 10 V in a device having a separated-function type two-layer configuration using ITO as an anode, a magnesium-silver alloy as a cathode, an aluminum quinolinol complex as an electron-transporting material and a luminescent material, and a triphenyl amine derivative as a hole-transporting material. The related patents include U.S. Pat. No. 4,539,507 B, U.S. Pat. No. 4,720,432 B, U.S. Pat. No. 4,885,211 B, and so on.

In addition, it is possible to generate luminescence in the range of ultraviolet to infrared lights by changing the types of the fluorescent organic compound, and in recent years various types of compounds have been studied actively. For instance, it is described in U.S. Pat. No. 5,151,629 B, U.S. Pat. No. 5,409,783 B, and U.S. Pat. No. 5,382,477 B, JP 2-247278 A, JP 3-255190 A, JP 5-202356 A, JP 9-202878 A, JP 9-227576 A, and so on.

Furthermore, in addition to the organic luminescence device using the low molecular weight material as mentioned above, an organic luminescence device using a conjugate polymer has been reported by a group of the Cambridge University (Nature, 347, 539 (1990)). In this report, luminescence from a single layer is confirmed by the film formation of polyphenylene vinylene (PPV) using a coating system. The related patents of the organic luminescence device using the conjugate polymer include U.S. Pat. No. 5,247,190 B, U.S. Pat. No. 5,514,878 B, U.S. Pat. No. 5,672,678 B, JP 4-145192 A, JP 5-247460 A, and so on.

In this way, the recent progress in the organic luminescence device is remarkable, and the characteristics thereof suggest the possibility of applications for various purposes, which enable the luminescence device with a high luminance, a variety of luminescence wavelengths, a high-speed response, and a thin and lightweight form.

However, many problems still remain to be solved regarding the durability with respect to a change with time due to a long-term usage, deterioration caused by an atmospheric gas including oxygen, moisture, or the like, and so on. Besides, in the case of considering the applications to a full color display and so on, under the present conditions, there are needs for an optical output of higher luminance or higher conversion efficiency, and for luminescences of blue, green, and red having good color purity.

For instance, JP 2001-52868 A discloses a diamine compound but no blue luminescence with a high color purity (chromaticity coordinates: x, y=0.14 to 0.15, 0.09 to 0.10) has been obtained. In addition, an example of using a compound having a similar diamine skeleton is disclosed in JP 11-312587 A. However, there has been obtained no blue luminescence with a high color purity.

DISCLOSURE OF THE INVENTION

The present invention has been made for solving such a problem inherent to the prior art and an object of the present invention is to provide a novel monoamino compound.

In addition, another object of the present invention is to provide an organic luminescence device having a luminescence hue with an extremely high purity, and also having an optical output of a high luminance with a high efficiency and a long life time.

Furthermore, another object of the present invention is to provide an organic luminescence device which can be produced easily at a comparatively low cost.

For solving the above problems, the present inventors have finally completed the present invention as a result of extensive studies.

Therefore, a monoamino compound according to the present invention is represented by the following general formula [1]:

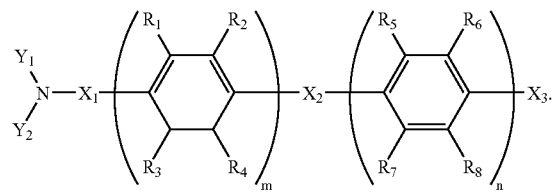

[1]

(where $X_1$ and $X_2$ represent divalent groups respectively selected from the group consisting of a substituted or unsubstituted alkylene group, aralkylene group, arylene group and heterocyclic group; and an alkylene group, an aralkylene group, an alkenylene group, an amino group, a silyl group, a carbonyl group, an ether group and a thioether group, each of which has a coupling group including a substituted or unsubstituted arylene group or a divalent heterocyclic group, in which $X_1$ and $X_2$ may be identical with or different from each other, and also $X_1$ and $X_2$ may be directly bonded with each other;

$X_3$ represents a group selected from the group consisting of a hydrogen atom, a halogen group, and substituted or unsubstituted alkyl group, aralkyl group, aryl group, and heterocyclic group, in which $X_3$ may be identical with or different from $X_1$ or $X_2$;

$Y_1$ and $Y_2$ represent groups respectively selected from the group consisting of a substituted or unsubstituted alkyl group, aralkyl group, aryl group and heterocyclic group; a substituted or unsubstituted alkylene group, aralkylene group, alkenylene group, amino group, and silyl group, each of which has a coupling group including a substituted or unsubstituted arylene group or a divalent heterocyclic group; and an unsubstituted carbonyl group, ether group, and thioether group, each of which has a coupling group including a substituted or unsubstituted arylene group or a divalent heterocyclic group, in which $Y_1$ and $Y_2$ may be identical with or different from each other;

$Y_1$ and $Y_2$, or $X_1$, $Y_1$, and $Y_2$ may be bonded with each other to form a ring;

$R_1$ to $R_8$ are groups respectively selected from the group consisting of a hydrogen atom, a halogen group, and a substituted or unsubstituted alkyl group, aralkyl group, and aryl group, in which $R_1$ to $R_8$ may be identical with or different from each other; and m+n denotes an integer number of 4 to 10 when all of $R_1$ to $R_8$ are hydrogen atoms, and $X_1$ and $X_2$ are directly bonded with each other, and $X_3$ is a hydrogen atom, or denotes an integer number of 1 to 10 under the other conditions.)

Further, an organic luminescence device according to the present invention includes at least a pair of electrodes including an anode and a cathode and one or a plurality of layers containing an organic compound sandwiched between the pair of electrodes, in which at least one of the layers containing the organic compound contains at least one of the compounds represented by the general formula [1].

BEST MODE FOR CARRYING OUT THE INVENTION

Figure 1:
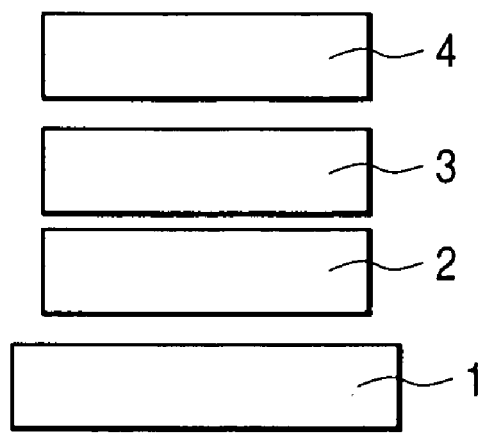
FIG. 1 is a cross-sectional diagram that illustrates an example of an organic luminescence device in accordance with the present invention.

Hereinafter, the present invention will be described in detail.

At first, a monoamino compound of the present invention will be described.

The monoamino compound of the present invention is represented by the above general formula [I].

The monoamino compound of the present invention can be mainly used as a material for an organic luminescence device, and when the compound is used as a luminescent material, a device having a high color purity, a high luminescence efficiency, and a long life time can be obtained even in a single layer. In addition, a luminescence spectrum having a narrower half-value width, i.e., luminescence having a more excellent color purity, can be obtained by introducing a comparatively-rigid structure such as p-phenylene skeleton into a main chain of a molecule. Furthermore, as a Stokes shift is prevented, it becomes possible to prevent the shift of a luminescence wavelength and to shift the absorbance toward longer wavelengths. In the case of using the compound as a dopant material, it also becomes possible to use a host material having a luminescence spectrum on relatively longer wavelengths.

The monoamino compound of the present invention can be used for the objects of both the dopant material and the host material in a luminescent layer, so that a device having a high color purity, a high luminescence efficiency, and a long life time can be obtained. In particular, a higher-efficient device that retains luminescence with a high color purity and has a higher efficiency can be obtained by the use of it as a dopant material in combination with an appropriate host material which tends to cause an energy shift.

Specific examples of substituents in the above general formula [1] will be described below.

The substituted or unsubstituted, chain and cyclic alkyl group includes a methyl group, an ethyl group, a n-propyl group, a n-butyl group, a n-hexyl group, a n-decyl group, an iso-propyl group, an iso-butyl group, a tert-butyl group, a tert-octyl group, a trifluoromethyl group, a cyclohexyl group, a cyclohexylmethyl group, and the like, but the group is not limited thereto.

The substituted or unsubstituted aralkyl group includes a benzyl group, a phenethyl group, and the like, but the group is not limited thereto.

The substituted or unsubstituted aryl group includes a phenyl group, a 4-methylphenyl group, a 4-methoxyphenyl group, a 4-ethylphenyl group, a 4-fluorophenyl group, a 3,5-dimethylphenyl group, a triphenylamino group, a biphenyl group, a terphenyl group, a naphthyl group, an anthracenyl group, a phenanthrelyl group, a pyrenyl group, a tetracenyl group, a pentacenyl group, a fluorenyl group, a triphenylenyl group, a perylenyl group, and the like, but the group is not limited thereto.

The substituted or unsubstituted heterocyclic group includes a pyrrolyl group, a pyridyl group, a bipyridyl group, a methylpyridyl group, a terpyrrolyl group, a thienyl group, a terthienyl group, a propylthienyl group, a furyl group, a quinolyl group, a carbazolyl group, an oxazolyl group, an oxadiazolyl group, a thiazolyl group, a thiadiazolyl group, and the like, but the group is not limited thereto.

The substituted or unsubstituted alkylene group includes a methylene group, an ethylene group, a propylene group, an iso-propylene group, a butylene group, a tert-butylene group, a hexylene group, a heptylene group, a cyclohexylene group, a cyclohexylmethylene group, and the like, but the group is not limited thereto.

The substituted or unsubstituted aralkylene group includes a benzylene group, a phenylethylene group, a phenethylene group, and the like, but the group is not limited thereto.

The substituted or unsubstituted arylene group includes a phenylene group, a biphenylene group, a 2,3,5,6-tetrafluorophenylene group, a 2,5-dimethylphenylene group, a naphtylene group, an anthracenylene group, a phenanthrenylene group, a tetracenylene group, a pentacenylene group, a perylenylene group, and the like, but the group is not limited thereto.

The substituted or unsubstituted divalent heterocyclic group includes a furanylene group, a pyrrorylene group, a pyridinylene group, a terpyridinylene group, a thiophenylene group, a terthiophenylene group, an oxazolylene group, a thiazolylene group, a carbazolylene group, and the like, but the group is not limited thereto.

The substituted or nonsubstituted alkenyl group includes a vinyl group, an allyl group (a 2-propenyl group), a 1-propenyl group, an iso-propenyl group, a 2-butenyl group, and the like, but the group is not limited thereto.

The substituted or unsubstituted amino group includes an amino group, a methylamino group, an ethylamino group, a dimethylamino group, a diethylamino group, a methylethylamino group, a benzylamino group, a methylbenzylamino group, a dibenzylamino group, an anilino group, a diphenylamino group, a phenyltolylamino group, a ditolylamino group, a dianisolylamino group, and the like, but the group is not limited thereto.

The substituted or unsubstituted carbonyl group includes an acetyl group, a propionyl group, an isobutyryl group, a methacryloyl group, a benzoyl group, a naphthoyl group, an anthroyl group, a trioyl group, and the like, but the group is not limited thereto.

The substituted or unsubstituted alkoxy group includes a methoxy group, an ethoxy group, a propoxy group, a 2-ethyl-octyloxy group, a phenoxy group, a 4-butylphenoxy group, a benzyloxy group, and the like, but the group is naturally not limited thereto.

The substituted or unsubstituted sulfide group includes a methylsulfide group, an ethylsulfide group, a phenylsulfide group, a 4-methylphenylsulfide group, and the like, but the group is not limited thereto.

As substituent groups which the above mentioned substituent groups may have include alkyl groups such as a methyl group, an ethyl group, a n-propyl group, an isopropyl group, a ter-butyl group, an octyl group, a benzyl group, and a phenethyl group; aralkyl groups; alkoxy groups such as a methoxy group, an ethoxy group, a propoxy group, a 2-ethyl-octyloxy group, a phenoxy group, a 4-butylphenoxy group, and a benzyloxy group; aryl groups such as a phenyl group, a 4-methylphenyl group, a 4-ethylphenyl group, a 3-chlorophenyl group, a 3,5-dimethylphenyl group, a triphenylamino group, a biphenyl group, a terphenyl group, a naphthyl group, an anthryl group, a phenanthryl group, and a pyrenyl group; heterocyclic groups such as a pyridyl group, a bipyridyl group, a methylpyridyl group, a thienyl group, a terthienyl group, a propylthienyl group, a furyl group, a quinolyl group, a carbazolyl group, and an N-ethylcarbazolyl group; halogen groups; a cyano group; a nitro group; and the like, but the groups are not limited thereto.

Next, although a typical example of the compound represented by the general formula [1] will be given, the present invention is not limited to those compounds.

TABLE 1

| [1] | m,n | R1-R4 | R5-R8 | X1 | X2 | X3 | Y1 | Y2 |
|---|---|---|---|---|---|---|---|---|
| 1 | 1,0 | H | — | Single bond | Single bond | 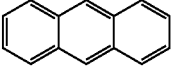 | Ph | Ph |
| 2 | 1,0 | H | — | Single bond | Single bond | 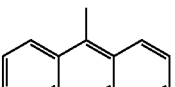 | 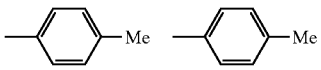 |  |
| 3 | 1,0 | H | — | 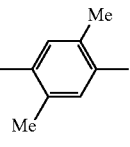 | Single bond | 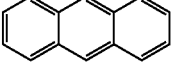 |  | 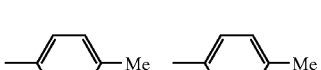 |
| 4 | 1,0 | H | — |  | Single bond | 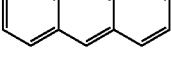 |  |  |
| 5 | 1,0 | H | — | Single bond | Single bond | 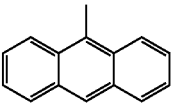 | Ph | 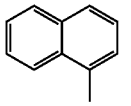 |
| 6 | 1,0 | H | — | Single bond | Single bond | 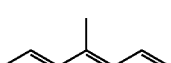 | Ph | 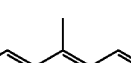 |
| 7 | 1,0 | H | — | Single bond | Single bond | 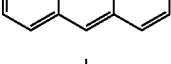 | Ph | 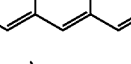 |
| 8 | 1,0 | H | — | Single bond | Single bond | 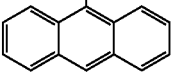 | Ph | 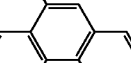 |

TABLE 1-continued
| [1] | m,n | R1-R4 | R5-R8 | X1 | X2 | X3 | Y1 | Y2 |
|---|---|---|---|---|---|---|---|---|
| 9 | 1,0 | H | — | Single bond | Single bond | 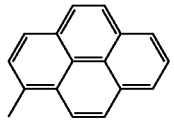 | Ph | Ph |
| 10 | 1,0 | H | — | Single bond | Single bond | 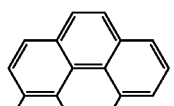 | 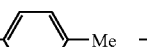 | 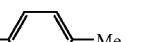 |
| 11 | 1,0 | H | — | 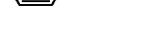 | Single bond |  | 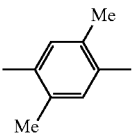 | 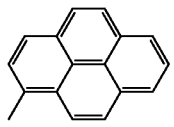 |
| 12 | 1,0 | H | — | 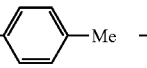 | Single bond | 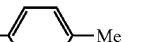 |  |  |
| 13 | 1,0 | H | — | Single bond | Single bond | 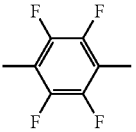 | Ph | 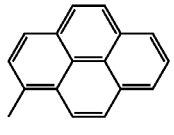 |
| 14 | 1,0 | H | — | Single bond | Single bond | 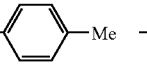 | Ph | 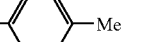 |
| 15 | 1,0 | H | — | Single bond | Single bond |  | Ph |  |
TABLE 2
| [1] | m,n | R1-R4 | R5-R8 | X1 | X2 | X3 | Y1 | Y2 |
|---|---|---|---|---|---|---|---|---|
| 16 | 1,0 | H | — | Single bond | Single bond | 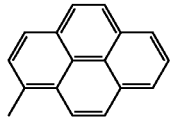 | Ph | 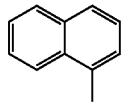 |
| 17 | 1,0 | F | — | Single bond | Single bond | 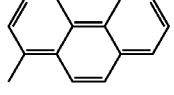 | 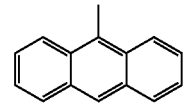 | 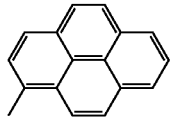 |
| 18 | 1,0 | F | — | Single bond | Single bond | 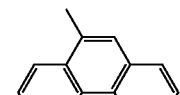 | Ph | 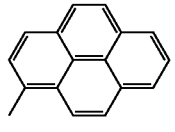 |

TABLE 2-continued
| [1] | m,n | R1-R4 | R5-R8 | X1 | X2 | X3 | Y1 | Y2 |
|---|---|---|---|---|---|---|---|---|
| 19 | 1,0 | F | — | Single bond | Single bond | 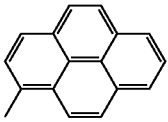 | 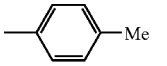 | 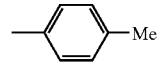 |
| 20 | 1,0 | F | — | Single bond | Single bond | 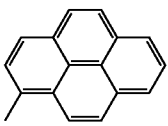 | Ph | 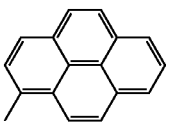 |
| 21 | 2,0 | H | — | Single bond | Single bond | 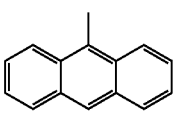 | Ph | Ph |
| 22 | 2,0 | H | — | Single bond | Single bond | 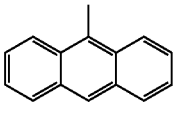 | 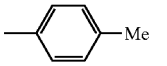 |  |
| 23 | 2,0 | H | — | Single bond | Single bond | 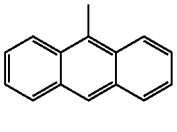 | 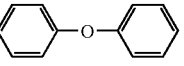 | 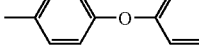 |
| 24 | 2,0 | H | — | 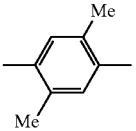 | Single bond | 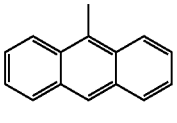 | 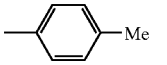 | 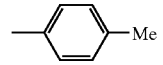 |
| 25 | 2,0 | H | — | 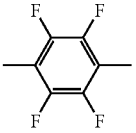 | Single bond | 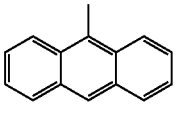 | 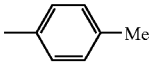 | 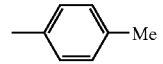 |
| 26 | 2,0 | H | — | 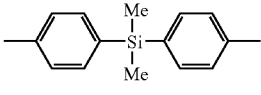 | Single bond | 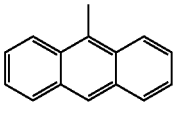 | 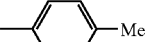 | 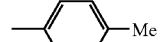 |
| 27 | 2,0 | H | — | Single bond | Single bond | 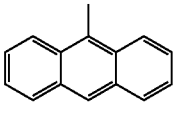 | Ph | 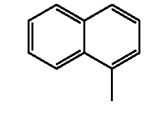 |
| 28 | 2,0 | H | — | Single bond | Single bond | 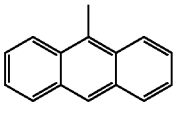 | Ph | 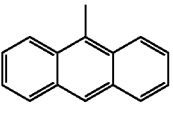 |
| 29 | 2,0 | H | — | Single bond | Single bond | 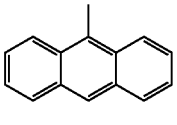 | Ph | 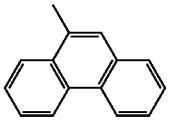 |

TABLE 2-continued
| [1] | m,n | R1-R4 | R5-R8 | X1 | X2 | X3 | Y1 | Y2 |
|---|---|---|---|---|---|---|---|---|
| 30 | 2,0 | H | — | Single bond | Single bond | 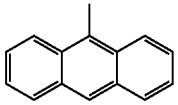 | Ph | 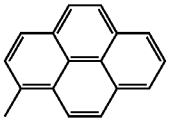 |
TABLE 3
| [1] | m,n | R1-R4 | R5-R8 | X1 | X2 | X3 | Y1 | Y2 |
|---|---|---|---|---|---|---|---|---|
| 31 | 2,0 | H | — | Single bond | Single bond | 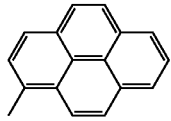 | Ph | Ph |
| 32 | 2,0 | H | — | Single bond | Single bond | 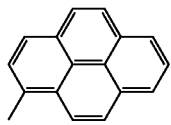 | 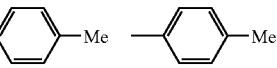 |  |
| 33 | 2,0 | H | — | 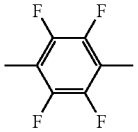 | Single bond | 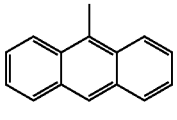 | 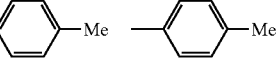 |  |
| 34 | 2,0 | H | — | Single bond | Single bond | 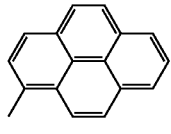 | Ph | 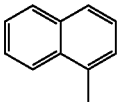 |
| 35 | 2,0 | H | — | Single bond | Single bond | 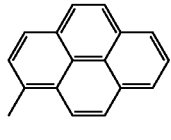 | Ph | 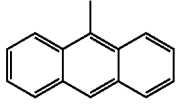 |
| 36 | 2,0 | H | — | Single bond | Single bond | 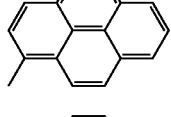 | Ph |  |
| 37 | 2,0 | H | — | Single bond | Single bond | 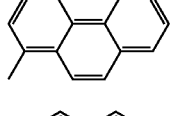 | Ph | 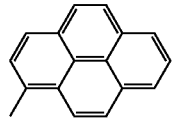 |
| 38 | 2,0 | F | — | Single bond | Single bond | 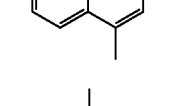 | Ph | 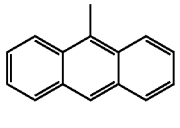 |
| 39 | 2,0 | F | — | Single bond | Single bond | 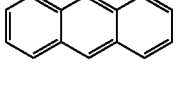 |  |  |

TABLE 3-continued
| [1] | m,n | R1-R4 | R5-R8 | X1 | X2 | X3 | Y1 | Y2 |
|---|---|---|---|---|---|---|---|---|
| 40 | 2,0 | F | — | Single bond | Single bond | 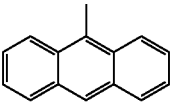 | Ph | 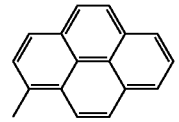 |
| 41 | 2,0 | F | — | Single bond | Single bond | 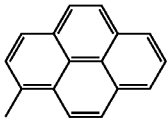 | 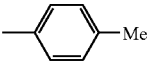 | 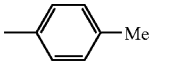 |
| 42 | 2,0 | F | — | Single bond | Single bond | 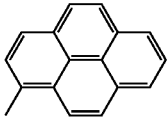 | Ph | 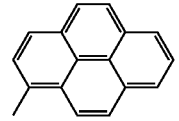 |
| 43 | 2,0 | F | — | Single bond | Single bond | F |  | 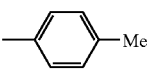 |
| 44 | 3,0 | H | — | Single bond | Single bond | 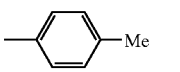 | Ph | Ph |
| 45 | 3,0 | H | — | Single bond | Single bond | 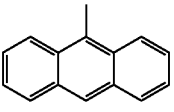 | 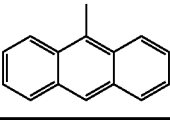 | 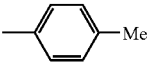 |
TABLE 4
| [1] | m,n | R1-R4 | R5-R8 | X1 | X2 | X3 | Y1 | Y2 |
|---|---|---|---|---|---|---|---|---|
| 46 | 3,0 | H | — | Single bond | Single bond | 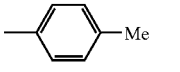 | 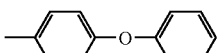 | 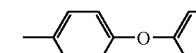 |
| 47 | 3,0 | H | — |  | Single bond | 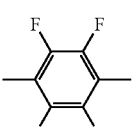 |  | 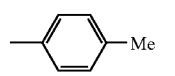 |
| 48 | 3,0 | H | — | Single bond | Single bond | 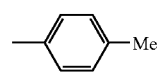 | Ph |  |
| 49 | 3,0 | H | — | Single bond | Single bond | 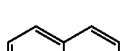 | Ph |  |
| 50 | 3,0 | H | — | Single bond | Single bond |  | Ph |  |

TABLE 4-continued
| [1] | m,n | R1-R4 | R5-R8 | X1 | X2 | X3 | Y1 | Y2 |
|---|---|---|---|---|---|---|---|---|
| 51 | 3,0 | H | — | Single bond | Single bond | 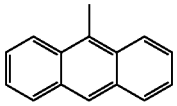 | Ph | 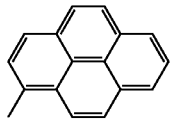 |
| 52 | 3,0 | H | — | Single bond | Single bond | 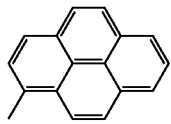 | Ph | Ph |
| 53 | 3,0 | H | — | Single bond | Single bond | 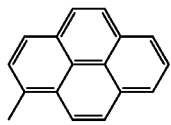 | 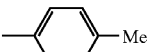—Me | 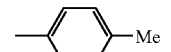—Me |
| 54 | 3,0 | H | — | Single bond | Single bond | 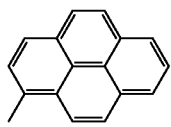 | Ph | 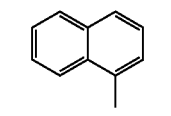 |
| 55 | 3,0 | H | — | Single bond | Single bond | 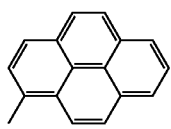 | Ph | 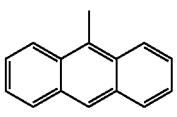 |
| 56 | 3,0 | H | — | Single bond | Single bond | 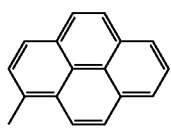 | Ph | 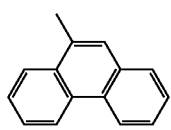 |
| 57 | 3,0 | H | — | Single bond | Single bond | 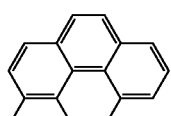 | Ph | 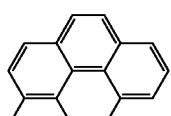 |
| 58 | 3,0 | F | — | Single bond | Single bond | 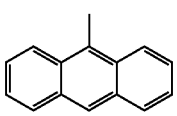 | 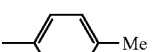—Me | 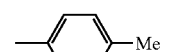—Me |
| 59 | 3,0 | F | — | Single bond | Single bond | 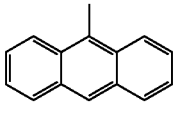 | Ph | 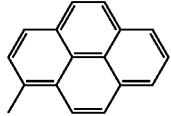 |
| 60 | 3,0 | F | — | Single bond | Single bond | 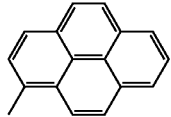 | 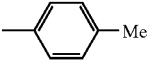—Me | 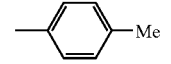—Me |

TABLE 5

| [1] | m,n | R1-R4 | R5-R8 | X1 | X2 | X3 | Y1 | Y2 |
|---|---|---|---|---|---|---|---|---|
| 61 | 3,0 | F | — | Single bond | Single bond | 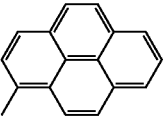 | Ph | 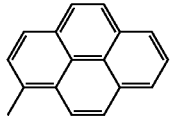 |
| 62 | 3,0 | F | — | Single bond | Single bond | F | 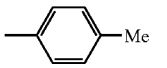 | 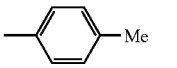 |
| 63 | 4,0 | H | — | Single bond | Single bond | H | 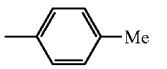 | 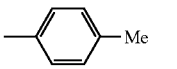 |
| 64 | 4,0 | H | — | Single bond | Single bond | 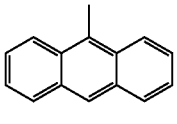 | 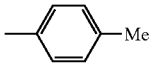 | 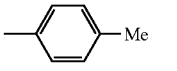 |
| 65 | 4,0 | H | — | Single bond | Single bond | H | Ph | 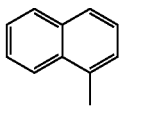 |
| 66 | 4,0 | H | — | Single bond | Single bond | H | Ph | 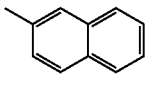 |
| 67 | 4,0 | H | — | Single bond | Single bond | H | Ph | 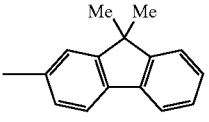 |
| 68 | 4,0 | H | — | Single bond | Single bond | H | Ph |  |
| 69 | 4,0 | H | — | Single bond | Single bond | H | 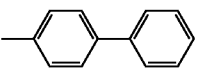 | 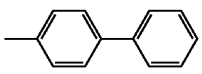 |
| 70 | 4,0 | H | — | Single bond | Single bond | H | Ph | 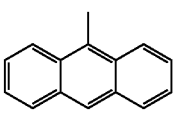 |
| 71 | 4,0 | H | — | Single bond | Single bond | H | Ph | 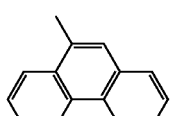 |
| 72 | 4,0 | H | — | Single bond | Single bond | H | Ph | 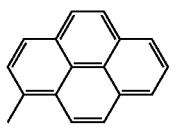 |
| 73 | 4,0 | F | — | Single bond | Single bond | F | 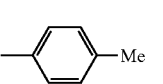 | 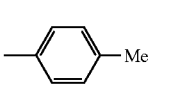 |
| 74 | 4,0 | F | — | Single bond | Single bond | F | Ph | 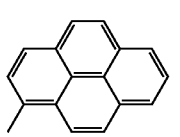 |

TABLE 5-continued

| [1] | m,n | R1-R4 | R5-R8 | X1 | X2 | X3 | Y1 | Y2 |
|---|---|---|---|---|---|---|---|---|
| 75 | 5,0 | H | — | Single bond | Single bond | H | 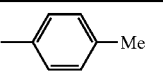 —Me | 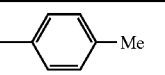 —Me |

TABLE 6

| [1] | m,n | R1-R4 | R5-R8 | X1 | X2 | X3 | Y1 | Y2 |
|---|---|---|---|---|---|---|---|---|
| 76 | 5,0 | H | — | Single bond | Single bond | H | Ph | 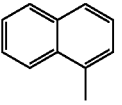 |
| 77 | 5,0 | H | — | Single bond | Single bond | H | Ph | 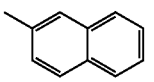 |
| 78 | 5,0 | H | — | Single bond | Single bond | H | Ph | 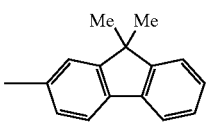 |
| 79 | 5,0 | H | — | Single bond | Single bond | H | Ph | 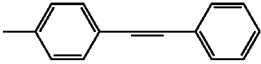 |
| 80 | 5,0 | H | — | Single bond | Single bond | H | 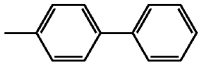 | 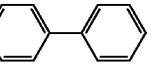 |
| 81 | 5,0 | H | — | Single bond | Single bond | H | Ph | 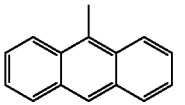 |
| 82 | 1,1 | H | F | Single bond | Single bond | F | 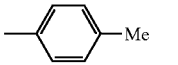—Me | 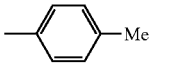—Me |
| 83 | 2,1 | H | F | Single bond | Single bond | F | 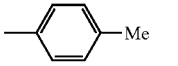—Me | 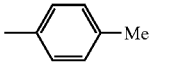—Me |
| 84 | 2,2 | H | F | Single bond | Single bond | F | 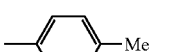—Me | 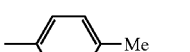—Me |
| 85 | 1,1 | H | H | Single bond | 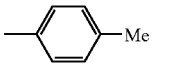 | H | 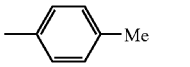—Me | 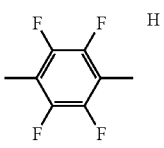—Me |
| 86 | 1,1 | H | H | Single bond | 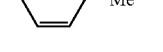 | H | 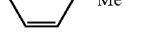—Me | 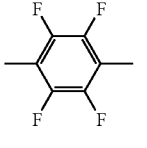—Me |
| 87 | 1,1 | H | H | Single bond | 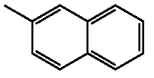 | H | Ph | 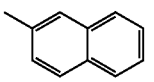 |

TABLE 6-continued

| [1] | m,n | R1-R4 | R5-R8 | X1 | X2 | X3 | Y1 | Y2 |
|---|---|---|---|---|---|---|---|---|
| 88 | 1,1 | H | H | Single bond | tetrafluorophenylene (F at 2,3,5,6) | H | Ph | 9,9-dimethylfluoren-2-yl |
| 89 | 1,1 | H | H | Single bond | tetrafluorophenylene (F at 2,3,5,6) | H | Ph | 4-(phenylethynyl)phenyl |
| 90 | 1,1 | H | H | Single bond | tetrafluorophenylene (F at 2,3,5,6) | H | biphenyl-4-yl | biphenyl-4-yl |

TABLE 7

| [1] | m,n | R1-R4 | R5-R8 | X1 | X2 | X3 | Y1 | Y2 |
|---|---|---|---|---|---|---|---|---|
| 91 | 1,1 | H | H | Single bond | tetrafluorophenylene (F at 2,3,5,6) | H | Ph | pyren-1-yl |
| 92 | 1,1 | H | H | Single bond | thiophene-2,5-diyl | H | 4-MeC$_6$H$_4$ | 4-MeC$_6$H$_4$ |
| 93 | 1,1 | H | H | Single bond | pyridine-2,6-diyl | H | 4-MeC$_6$H$_4$ | 4-MeC$_6$H$_4$ |
| 94 | 1,1 | H | H | Single bond | 4,4'-(dimethylsilanediyl)diphenylene | H | 4-MeC$_6$H$_4$ | 4-MeC$_6$H$_4$ |
| 95 | 1,1 | H | H | Single bond | 4,4'-oxydiphenylene | H | 4-MeC$_6$H$_4$ | 4-MeC$_6$H$_4$ |
| 96 | 1,1 | H | H | Single bond | 4,4'-(propane-2,2-diyl)diphenylene | H | 4-MeC$_6$H$_4$ | 4-MeC$_6$H$_4$ |
| 97 | 1,1 | H | H | Single bond | naphthalene-1,4-diyl | H | 4-MeC$_6$H$_4$ | 4-MeC$_6$H$_4$ |
| 98 | 1,1 | H | H | Single bond | anthracene-9,10-diyl | H | 4-MeC$_6$H$_4$ | 4-MeC$_6$H$_4$ |

TABLE 7-continued
| [1] | m,n | R1-R4 | R5-R8 | X1 | X2 | X3 | Y1 | Y2 |
|---|---|---|---|---|---|---|---|---|
| 99 | 1,1 | H | H | Single bond | 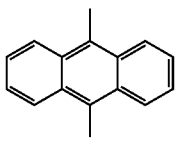 | H | Ph | 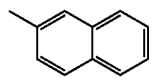 |
| 100 | 1,1 | H | H | Single bond | 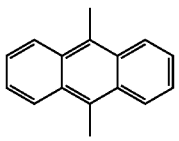 | H | Ph | 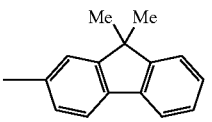 |
| 101 | 1,1 | H | H | Single bond | 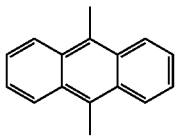 | H | Ph | 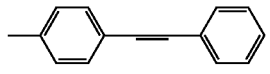 |
| 102 | 1,1 | H | H | Single bond | 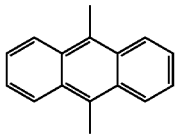 | H | 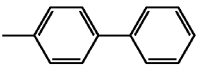 | 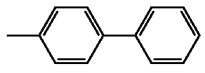 |
| 103 | 1,1 | H | H | Single bond | 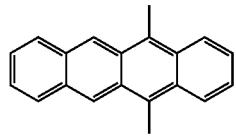 | H | 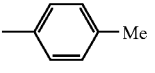 | 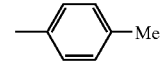 |
| 104 | 1,1 | H | H | Single bond | 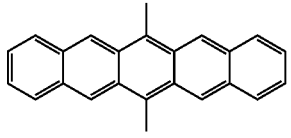 | H | 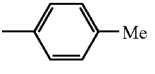 | 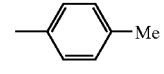 |
| 105 | 1,1 | H | H | Single bond | 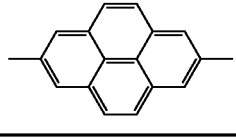 | H | 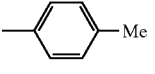 | 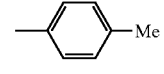 |
TABLE 8
| [1] | m,n | R1-R4 | R5-R8 | X1 | X2 | X3 | Y1 | Y2 |
|---|---|---|---|---|---|---|---|---|
| 106 | 1,1 | H | H | Single bond | 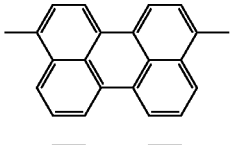 | H | 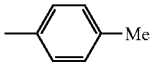 | 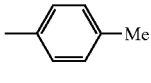 |
| 107 | 1,1 | H | H | Single bond | 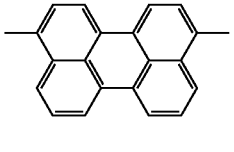 | H | 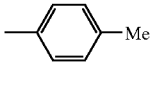 | 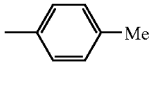 |

TABLE 8-continued
| [1] | m,n | R1-R4 | R5-R8 | X1 | X2 | X3 | Y1 | Y2 |
|---|---|---|---|---|---|---|---|---|
| 108 | 1,1 | H | H | Single bond | 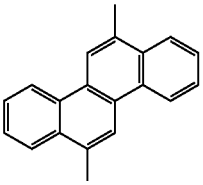 | H | 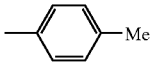 | 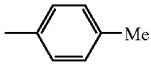 |
| 109 | 1,2 | H | H | Single bond | 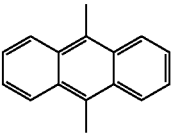 | H | 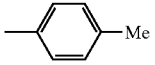 | 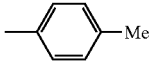 |
| 110 | 2,2 | H | H | Single bond | 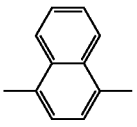 | H | 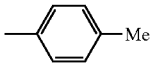 | 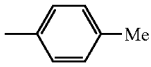 |
| 111 | 2,2 | H | H | Single bond | 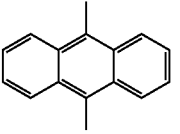 | H | 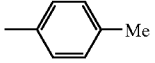 | 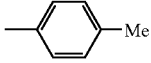 |
| 112 | 2,2 | H | H | Single bond | 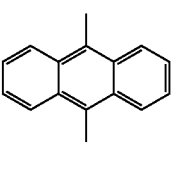 | H | Ph | 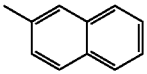 |
| 113 | 2,2 | H | H | Single bond | 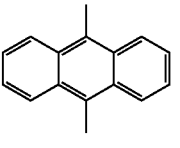 | H | Ph | 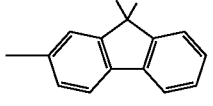 |
| 114 | 2,2 | H | H | Single bond | 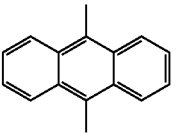 | H | Ph |  |
| 115 | 2,2 | H | H | Single bond | 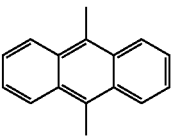 | H | 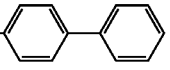 | 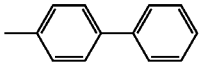 |
| 116 | 2,2 | H | H | Single bond | 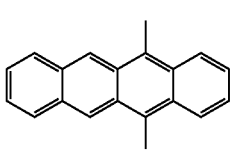 | H | 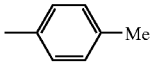 | 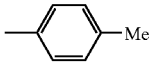 |
| 117 | 1,1 | H | F | Single bond | 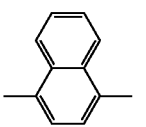 | F | 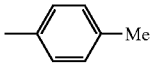 | 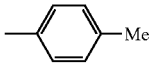 |

TABLE 8-continued

| [1] | m,n | R1-R4 | R5-R8 | X1 | X2 | X3 | Y1 | Y2 |
|---|---|---|---|---|---|---|---|---|
| 118 | 1,1 | H | F | Single bond | anthracene | F | —C6H4—Me | —C6H4—Me |
| 119 | 1,1 | H | F | Single bond | tetracene | F | —C6H4—Me | —C6H4—Me |
| 120 | 1,1 | H | H | naphthalene | anthracene | H | —C6H4—Me | —C6H4—Me |
| 121 | 2,2 | H | H | naphthalene | anthracene | H | —C6H4—Me | —C6H4—Me |

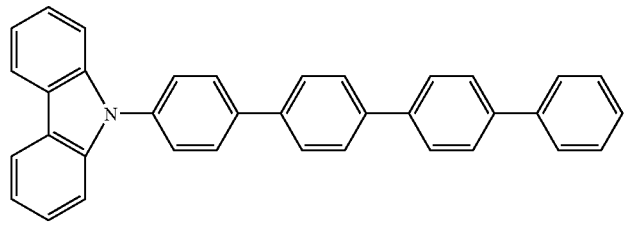

[1]-122

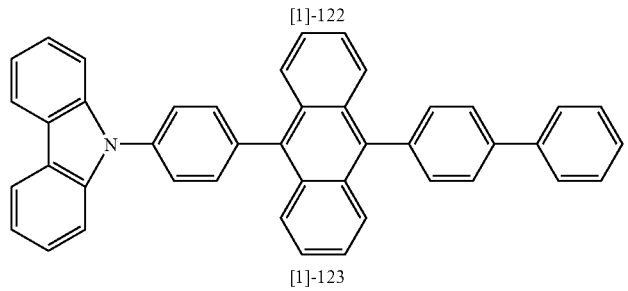

[1]-123

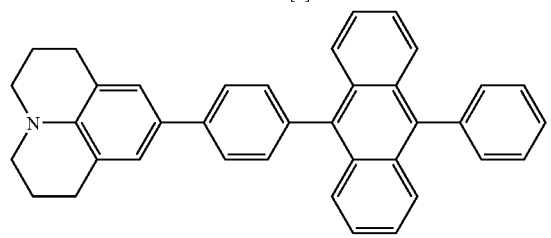

[1]-124

Next, the organic luminescence device according to the present invention will be described detail.

The organic luminescence device according to the present invention comprises at least a pair of electrodes including an anode and a cathode and one or a plurality of layers containing an organic compound sandwiched between the pair of electrodes, wherein at least one of the layers containing the organic compound contains at least one of the monoamino compounds represented by the above-described general formula [1].

The layer containing the compound represented by the general formula [1] preferably contains at least one of the compounds represented by the following general formulae [2] to [6]. In addition the layer containing the compound represented by the general formula [1] is preferably a luminescent layer.

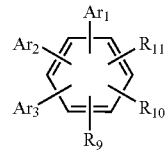

[2]

(wherein $Ar_1$ to $Ar_3$ represent groups respectively selected from the group consisting of a substituted or unsubstituted aryl group and heterocyclic group, in which $Ar_1$ to $Ar_3$ may be identical with or different from each other, or one of them may be a hydrogen atom, a substituted or unsubstituted alkyl group, or a substituted or unsubstituted aralkyl group; and $R_9$ to $R_{11}$ represent groups respectively selected from the group consisting of a hydrogen atom, a halogen group, substituted or unsubstituted alkyl group and aralkyl group, a substituted amino group, and a cyano group.)

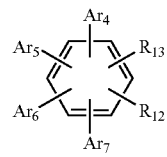

[3]

(wherein $Ar_4$ to $Ar_7$ represent groups respectively selected from the group consisting of a substituted or unsubstituted aryl group and heterocyclic group, in which $Ar_4$ to $Ar_7$ may be identical with or different from each other; and $R_{12}$ and $R_{13}$ represent groups selected from the group consisting of a hydrogen atom, a halogen group, substituted or unsubstituted alkyl group and aralkyl group, a substituted amino group, and a cyano group.)

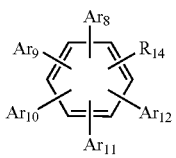

[4]

(wherein $Ar_8$ to $Ar_{12}$ represent groups respectively selected from the group consisting of a substituted or unsubstituted aryl group and heterocyclic group, in which $Ar_8$ to $Ar_{12}$ may be identical with or different from each other; and $R_{14}$ represents a group selected from the group consisting of a hydrogen atom, a halogen group, substituted or unsubstituted alkyl group, aralkyl group, aryl group and heterocyclic group, a substituted amino group, and a cyano group.)

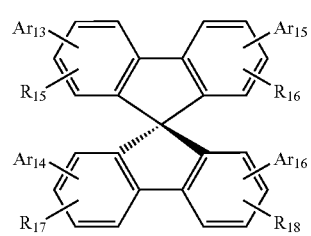

[5]

(wherein $Ar_{13}$ to $Ar_{16}$ represent groups respectively selected from the group consisting of a substituted or unsubstituted aryl group and heterocyclic group, in which $Ar_{13}$ to $Ar_{16}$ may be identical with or different from each other, or at most three of $Ar_{13}$ to $Ar_{16}$ may be a hydrogen atom, a substituted or unsubstituted alkyl group, or a substituted or unsubstituted aralkyl group; and $R_{15}$ to $R_{18}$ represent groups respectively selected from the group consisting of a hydrogen atom, a halogen group, substituted or unsubstituted alkyl group, aralkyl group, aryl group and heterocyclic group, a substituted amino group, and a cyano group.)

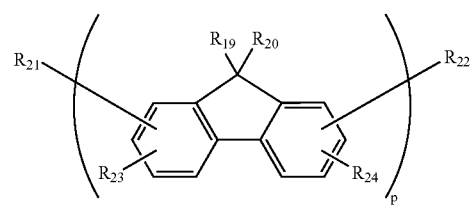

[6]

(wherein $R_{19}$ and $R_{20}$ represent groups respectively selected from the group consisting of a hydrogen atom, and substituted or unsubstituted alkyl group, aralkyl group, and aryl group, in which the $R_{19}$ groups or the $R_{20}$ groups bonded with different fluorene groups may be identical with or different from each other, and $R_{19}$ and $R_{20}$ bonded with the same fluorene group may be identical with or different from each other; and $R_{21}$ to $R_{24}$ represent groups respectively selected from the group consisting of a hydrogen atom, a halogen group, substituted or unsubstituted alkyl group, aralkyl group, and alkoxy group, a substituted silyl group, and a cyano group; and p is an integer number of 2 to 10.)

Each of the compounds represented by the general formulas [2] to [6] can be used for the purposes of both the dopant material and the host material in a luminescent layer, so that a device having a high color purity, a high luminescence efficiency, and a long life time can be obtained. A device that retains luminescence with a high color purity and has a higher efficiency can be obtained by the use of a compound represented by the general formula [1] as a dopant material and combining the compound with an appropriate host material that tends to cause an energy shift, for example the compounds represented by the general formulas [2] to [6]. The concentration of the dopant to the host material is preferably 0.01% by weight to 50% by weight, more preferably 0.5% by weight to 10% by weight.

Specific examples of substituents in the general formulae [2] to [6] are in common with those of the above general formula [1]. The followings are typical examples of the compounds represented by the general formulae [2] to [6], but the present invention is not limited to those compounds.

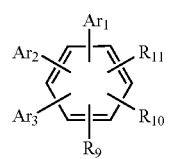
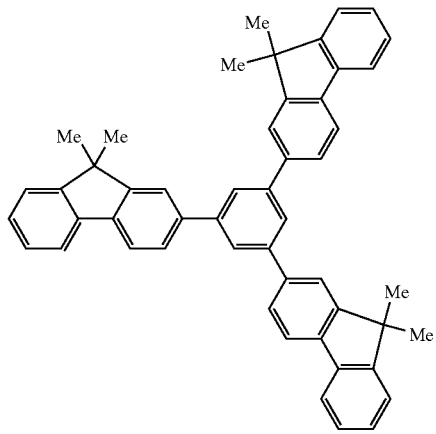
[2]
[2]-1
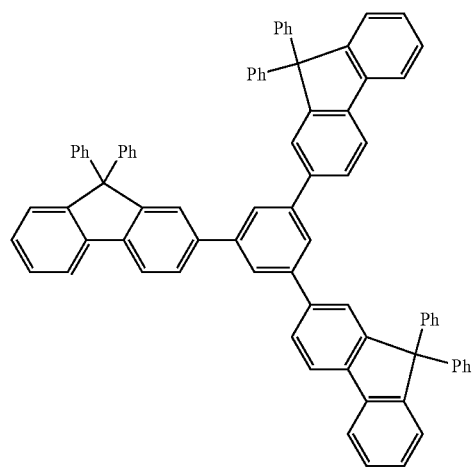
[2]-2
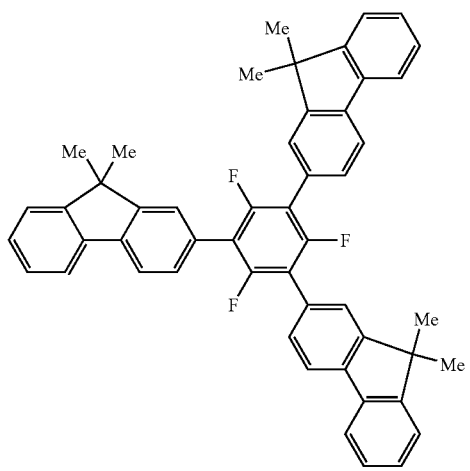
[2]-3
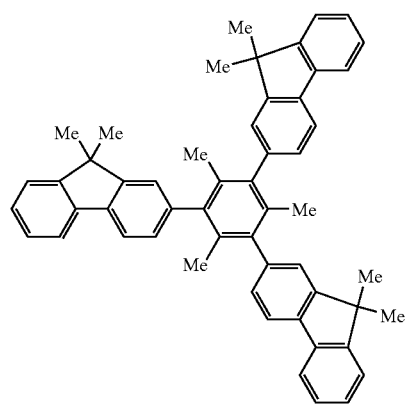
[2]-4
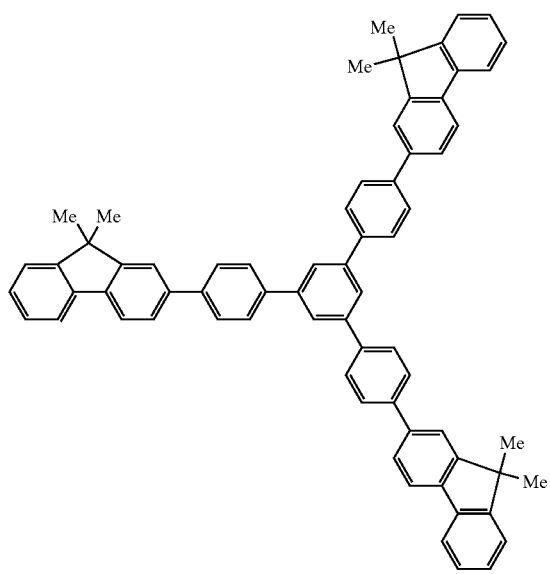
[2]-5

-continued
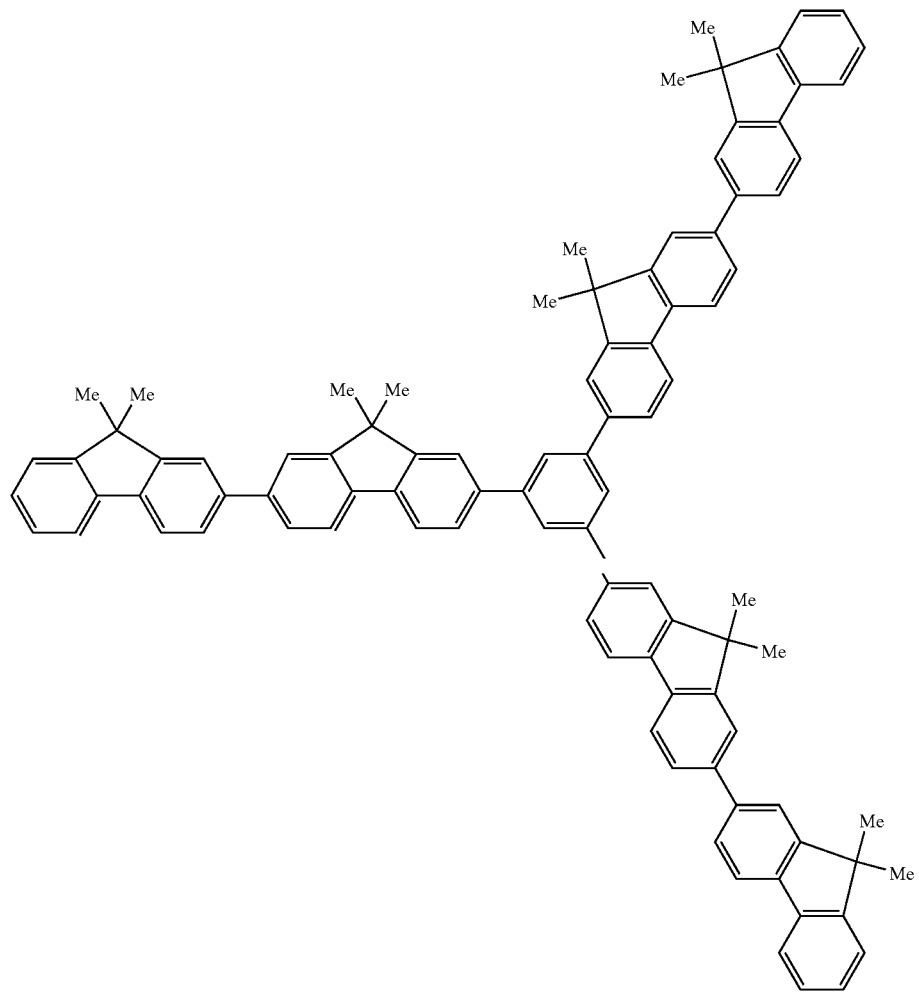
[2]-6
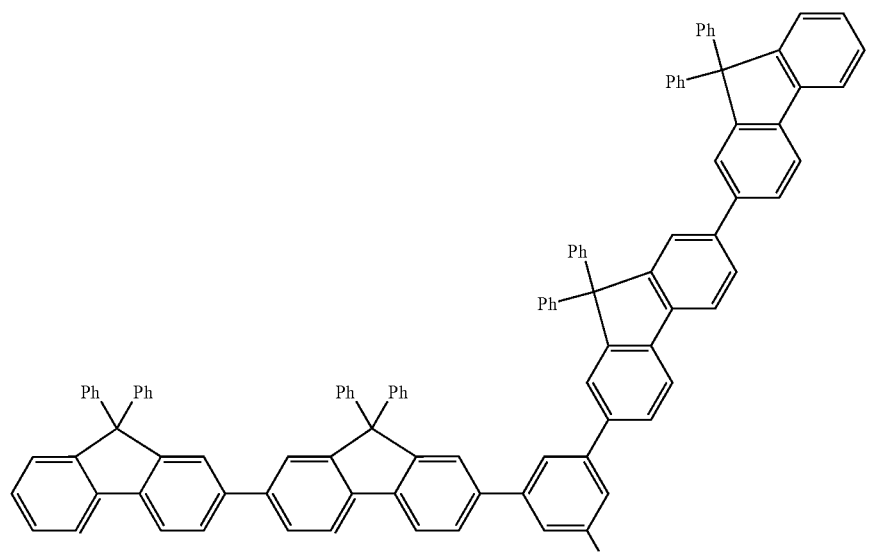
[2]-7

-continued
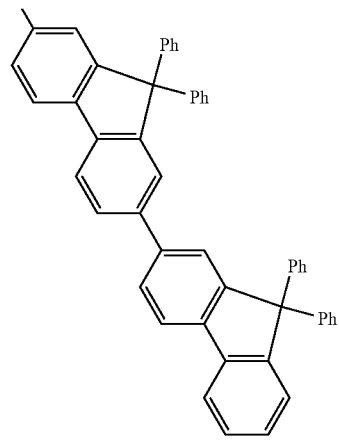
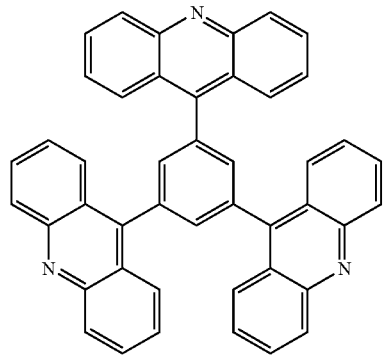
[2]-8
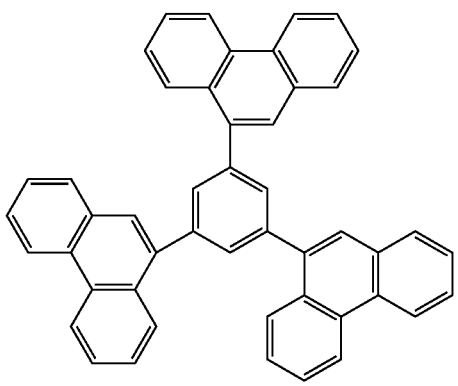
[2]-9
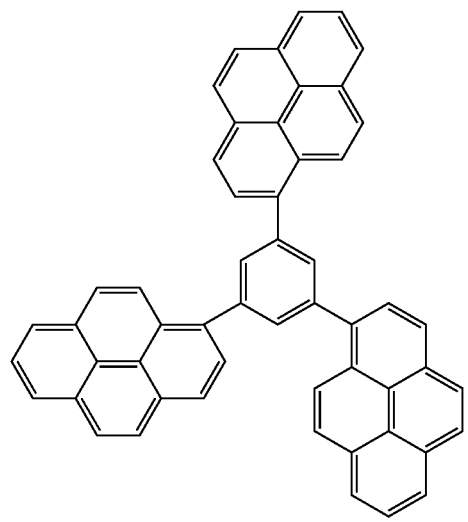
[2]-10

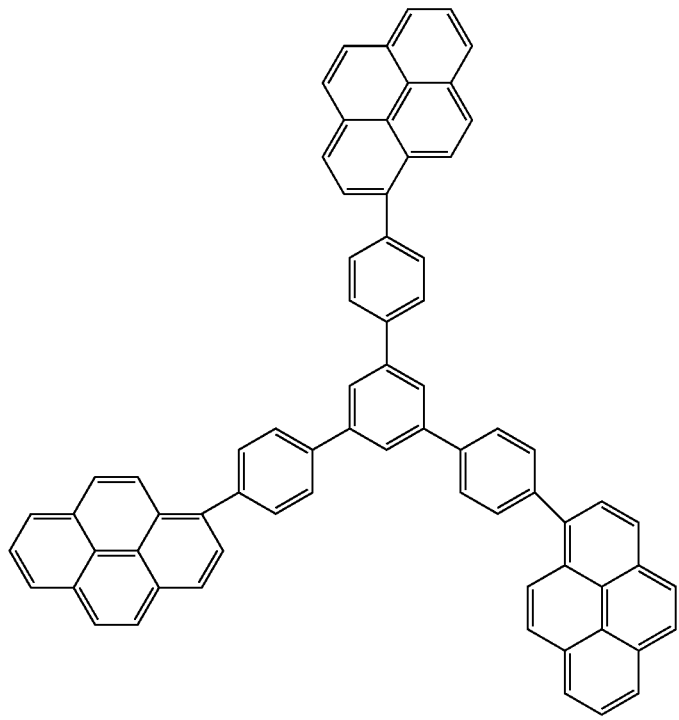
[2]-11
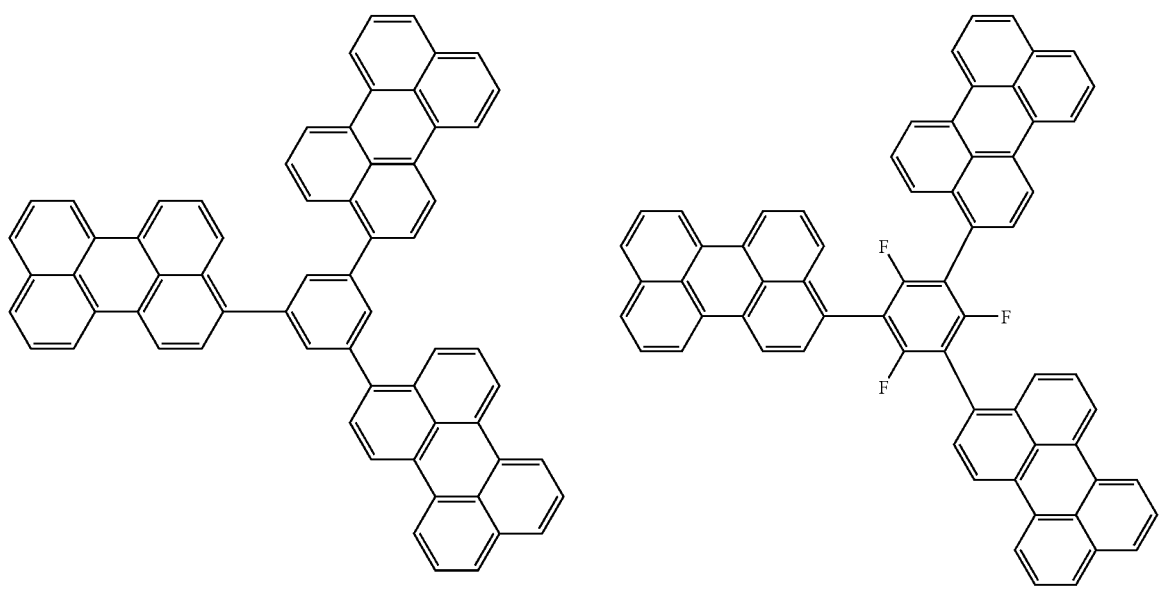
[2]-12
[2]-13

-continued
[2]-14
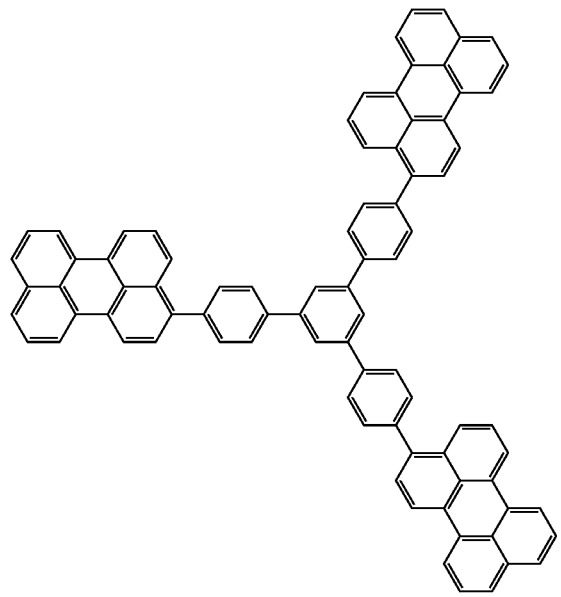
[2]-15
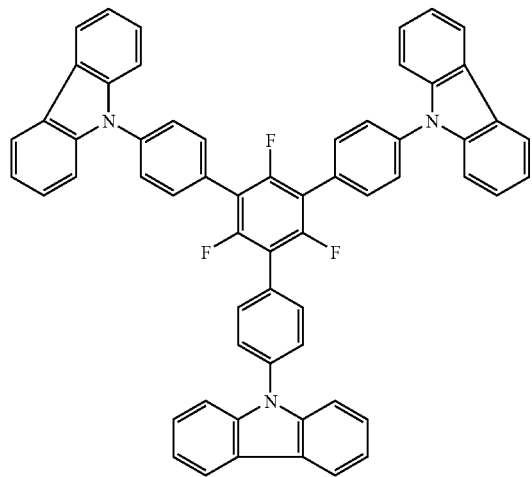
[3]
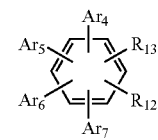
[3]-1
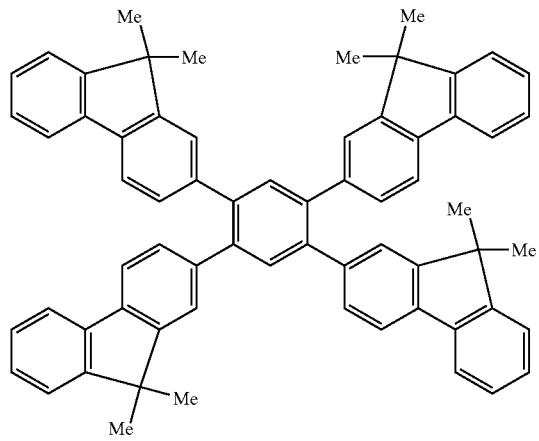
[3]-2
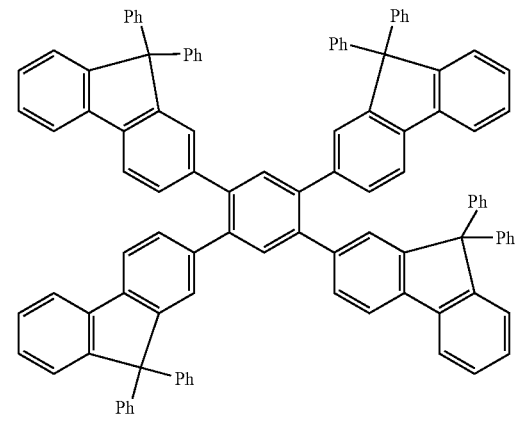

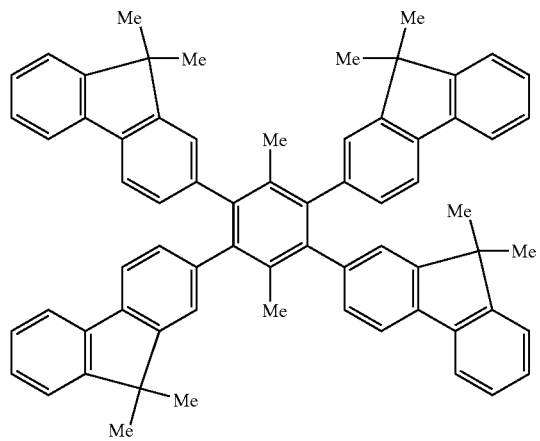
[3]-3
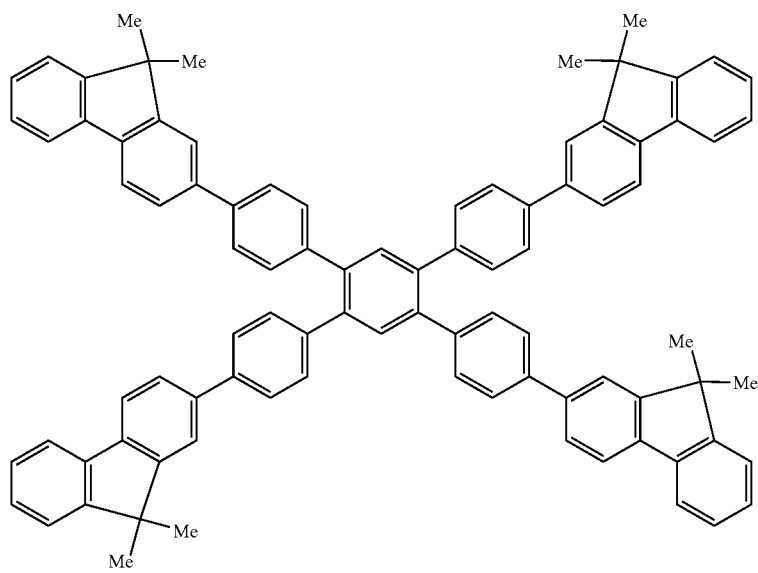
[3]-4
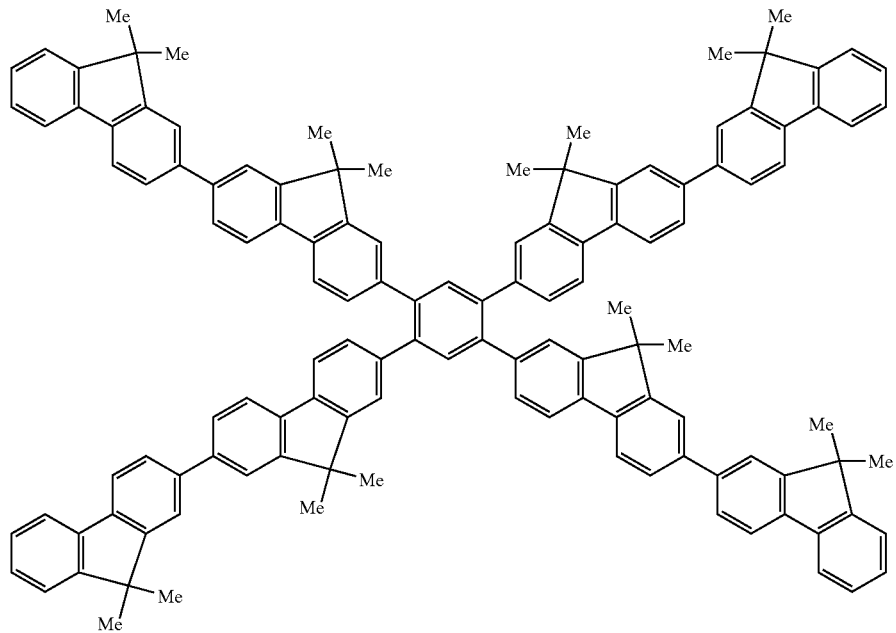
[3]-5

[3]-6
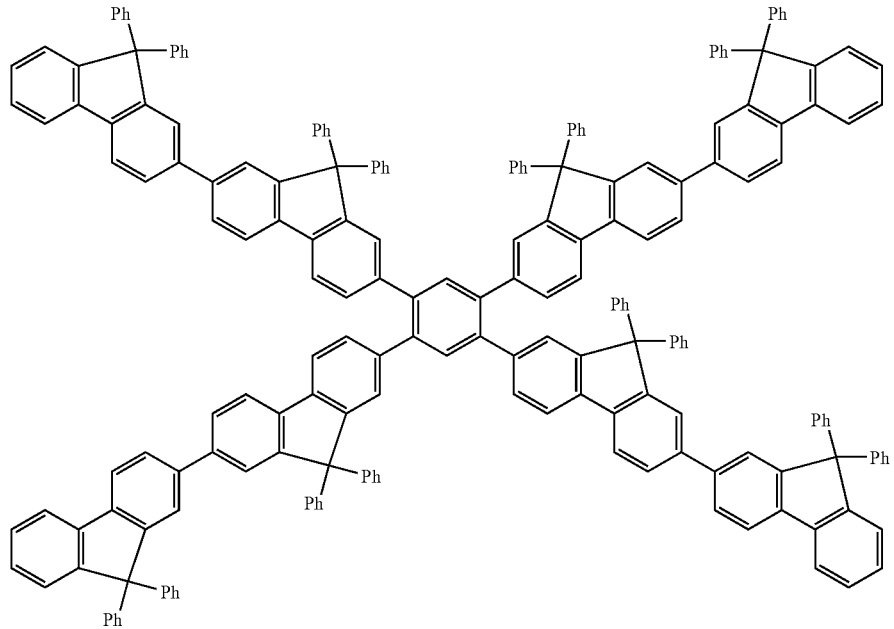
[3]-7
[3]-8
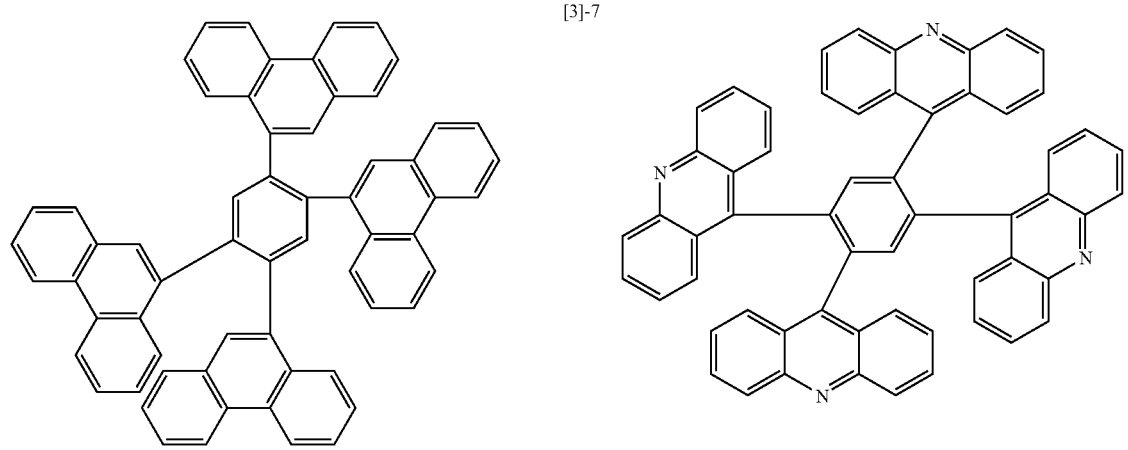
[3]-9
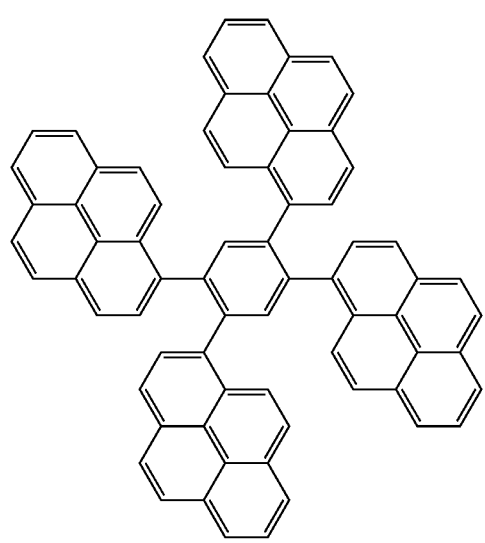

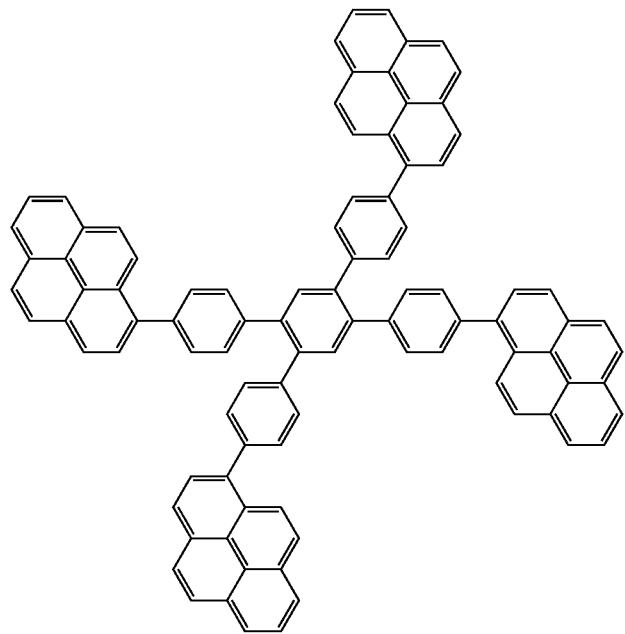
[3]-10
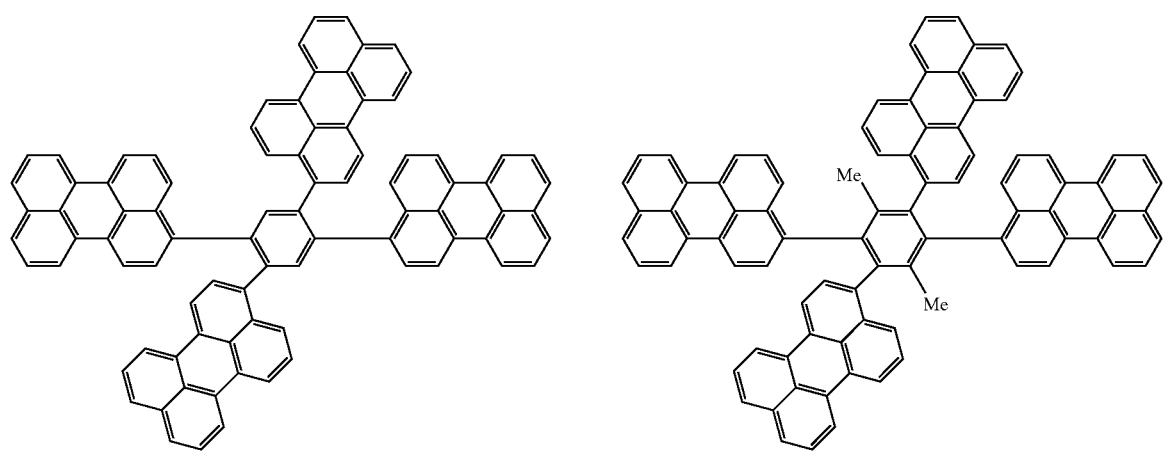
[3]-11
[3]-12

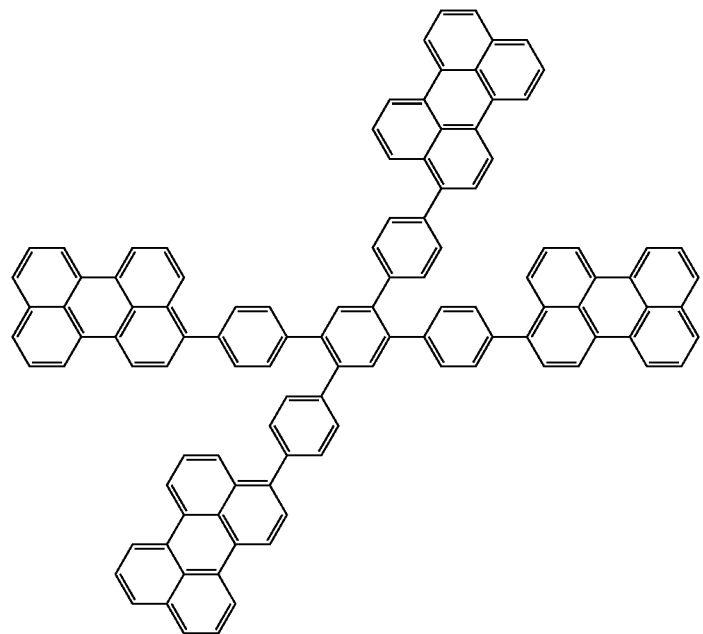
[3]-13
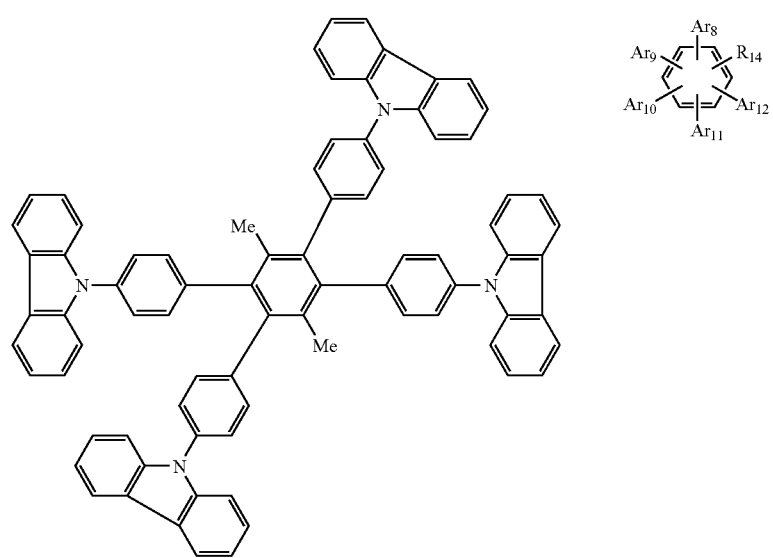
[3]-14
[4]

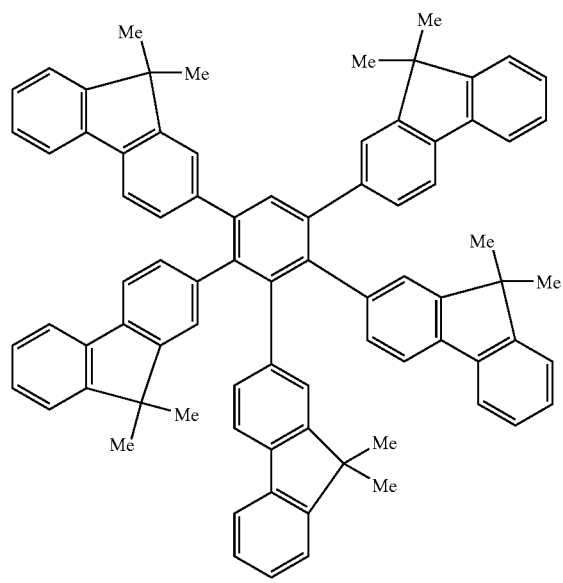

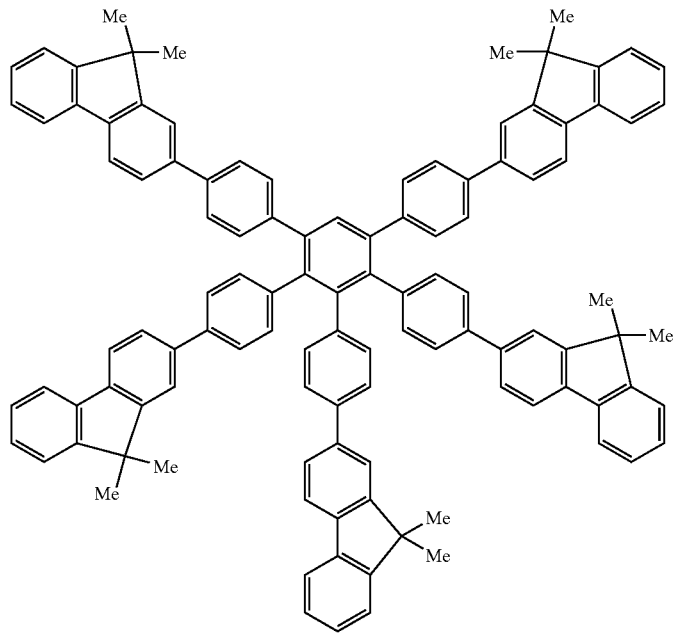
[4]-4
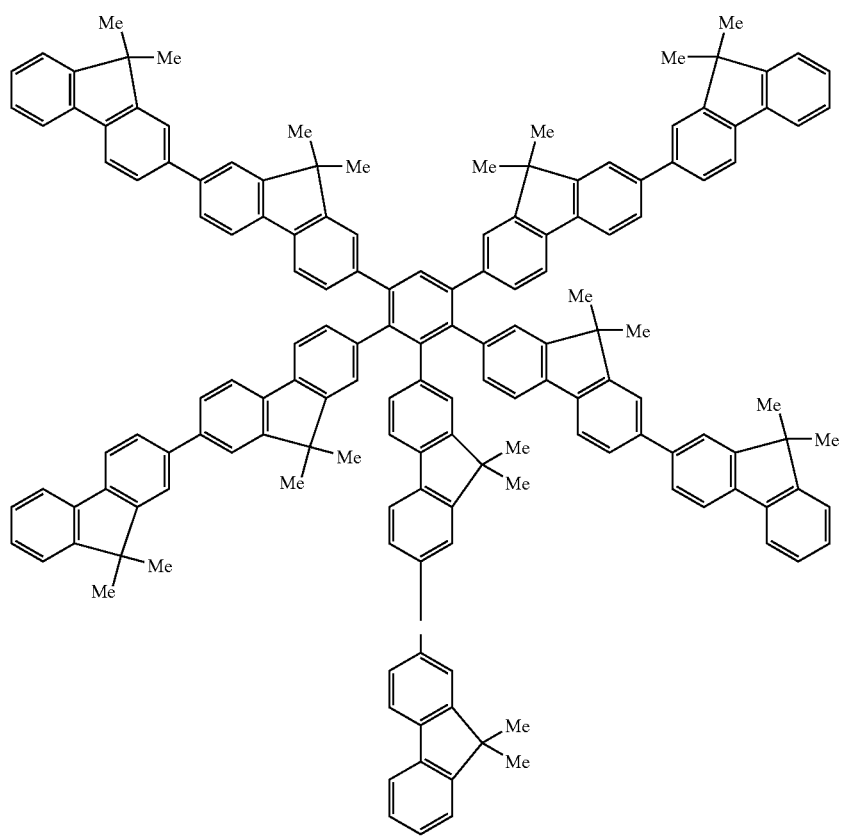
[4]-5

-continued
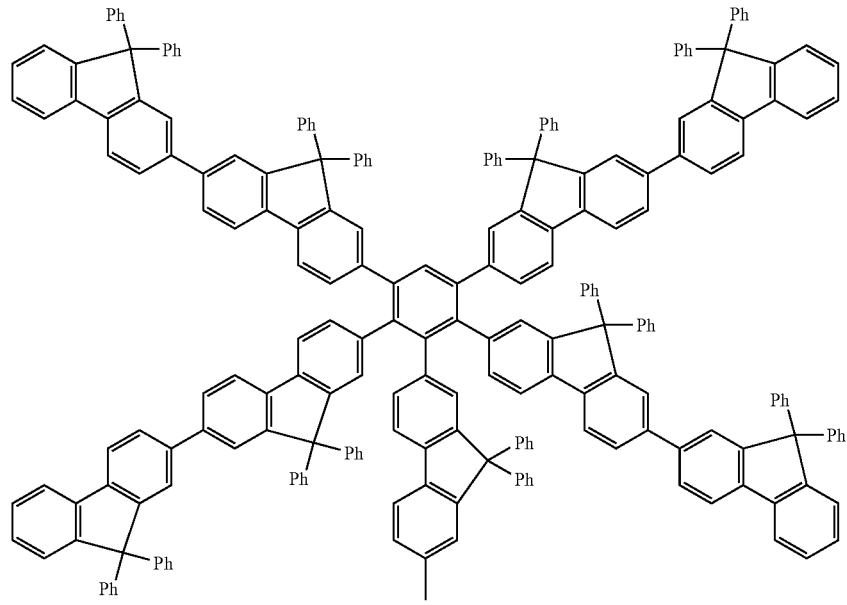
[4]-6
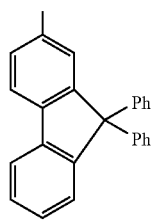
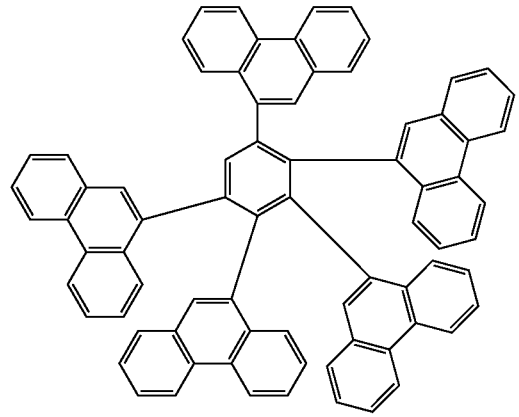
[4]-7
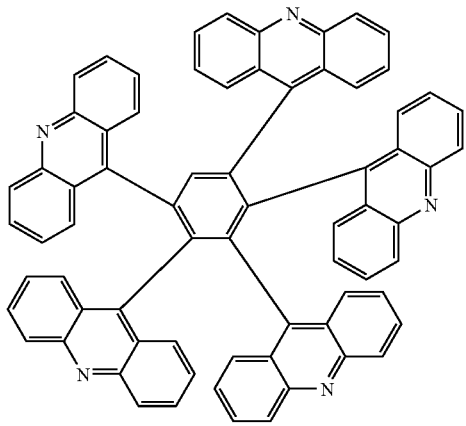
[4]-8

[4]-9
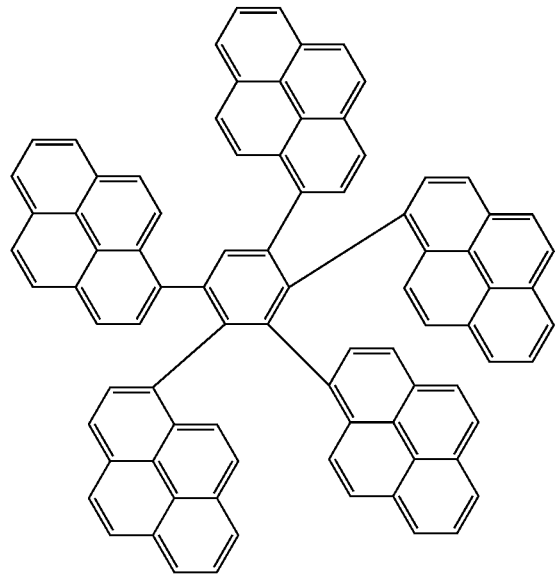
[4]-10
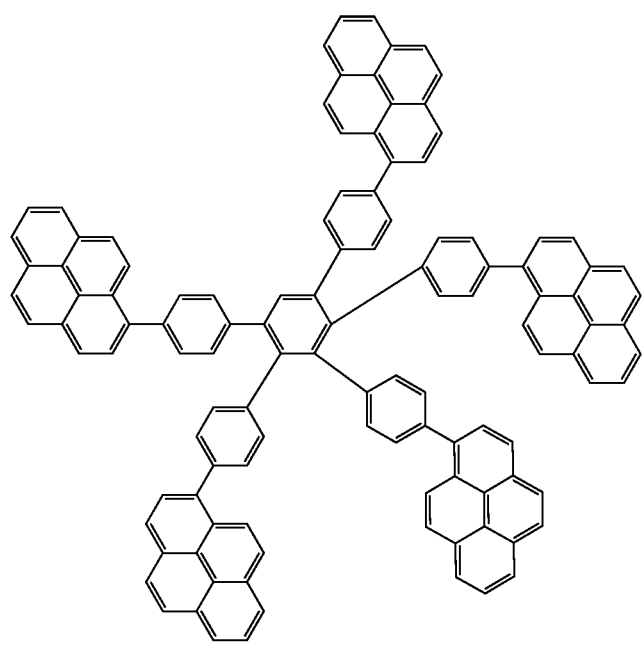

-continued
[4]-11
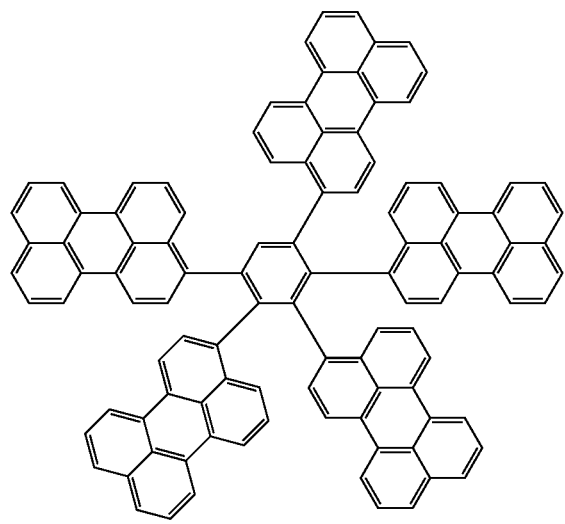
[4]-12
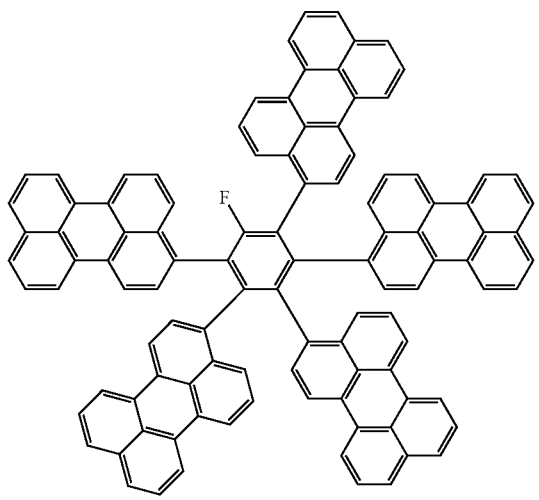
[4]-13
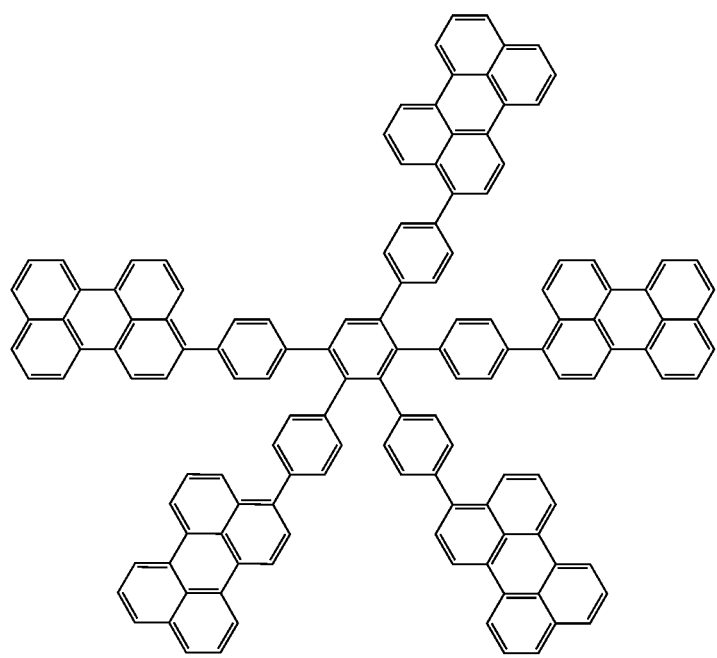

[4]-14
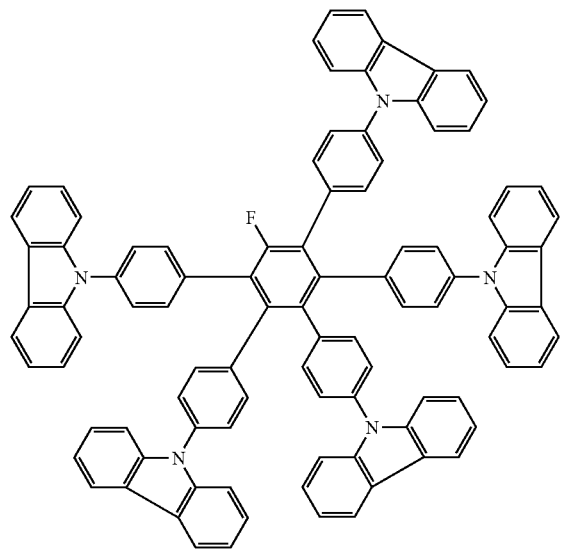
[4]-15
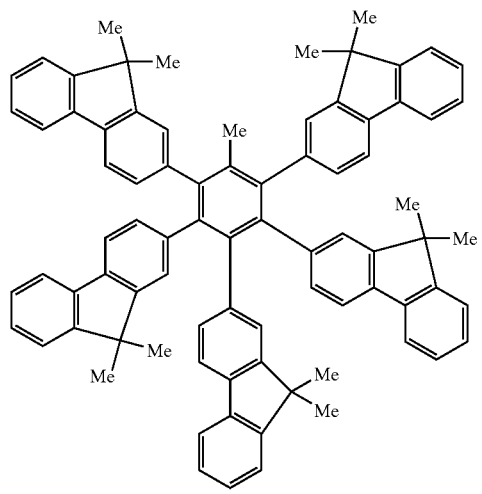
[4]-16
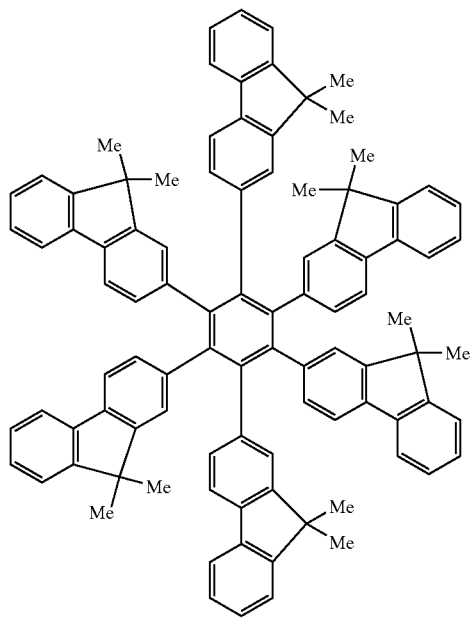

[4]-17
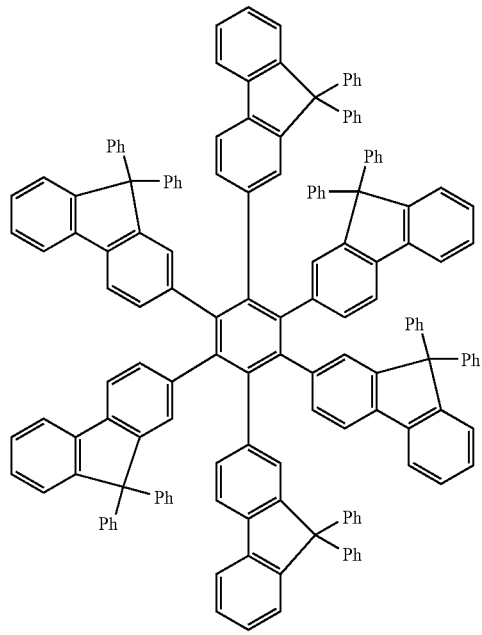
[4]-18
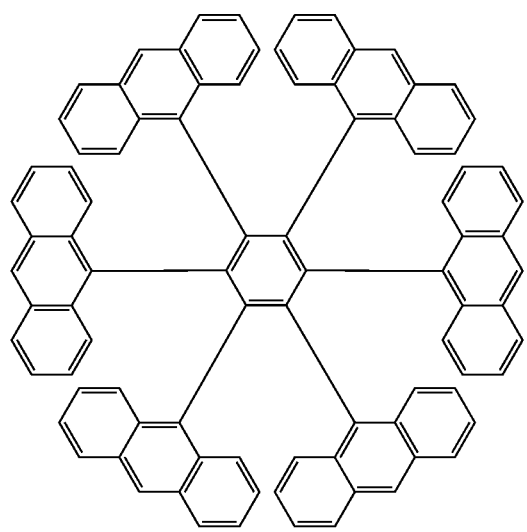
[4]-19
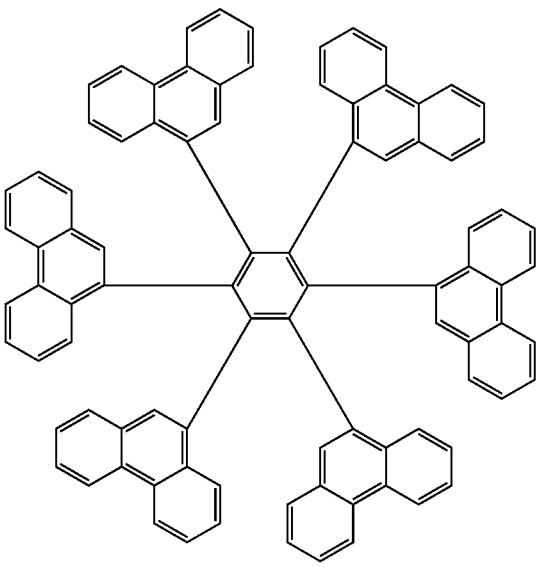

-continued
[4]-20
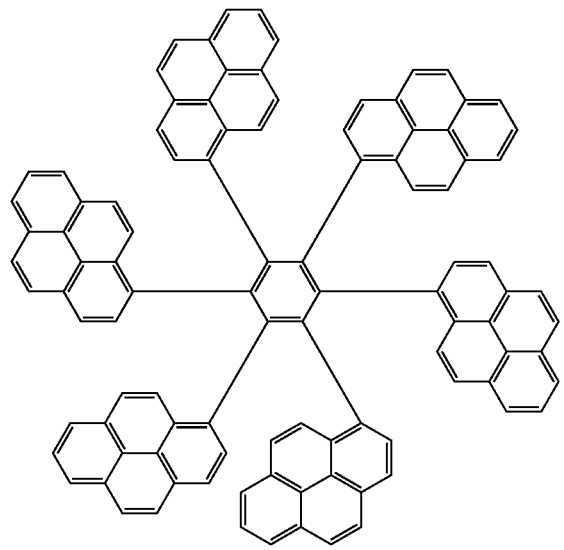
[4]-21
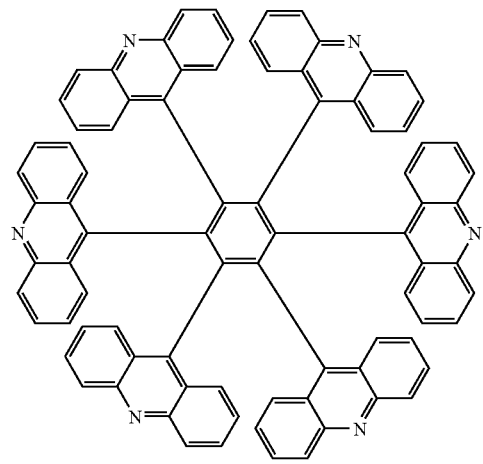
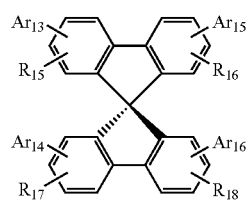
[5]
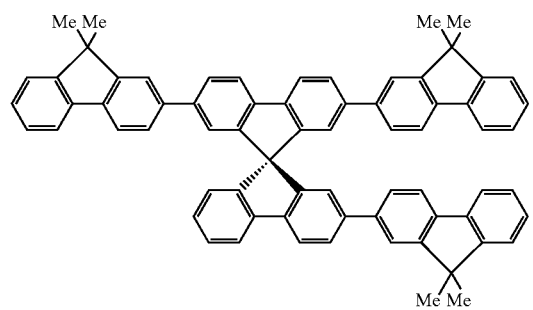
[5]-1
[5]-2
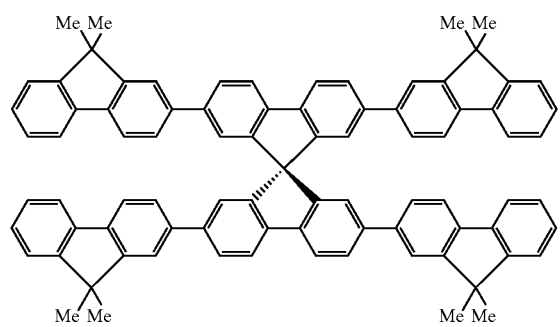
[5]-3
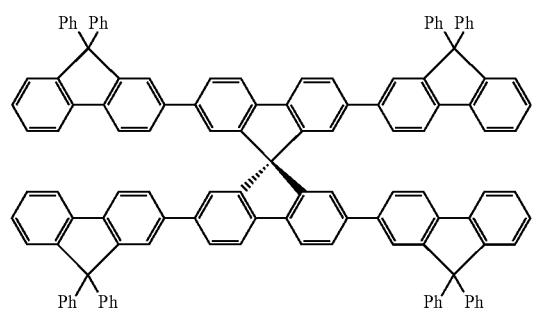
[5]-4
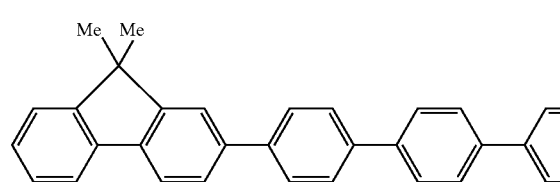

-continued
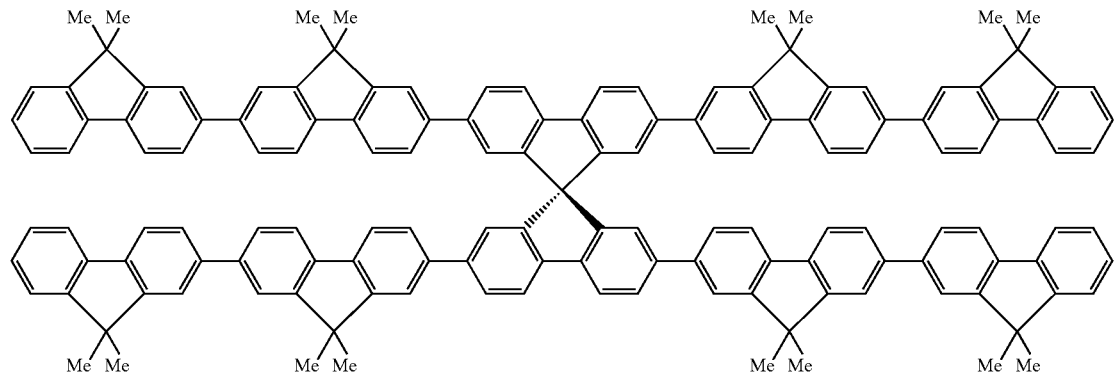
[5]-5
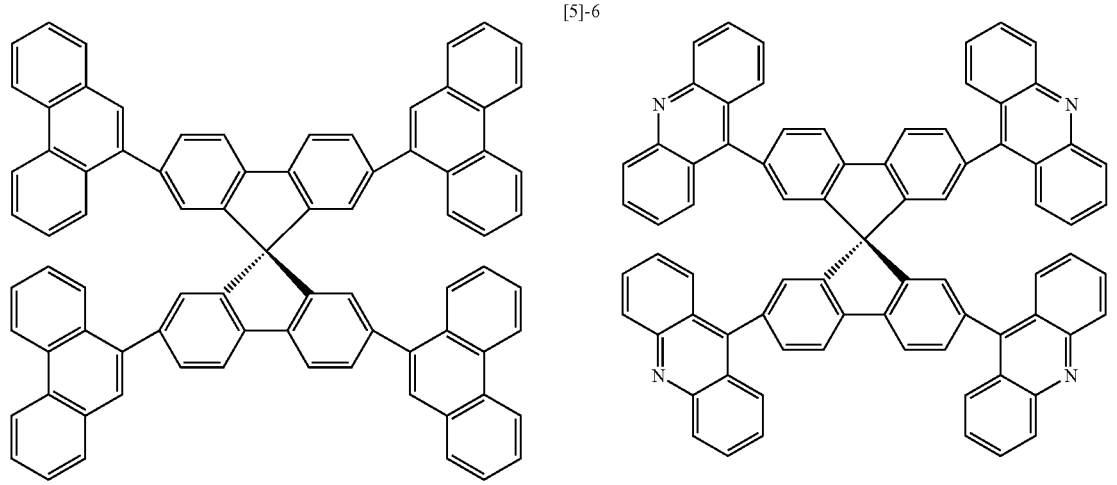
[5]-6 [5]-7
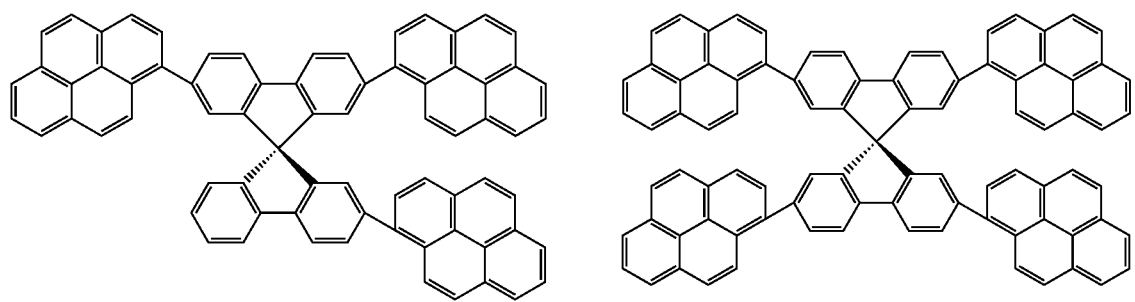
[5]-8 [5]-9
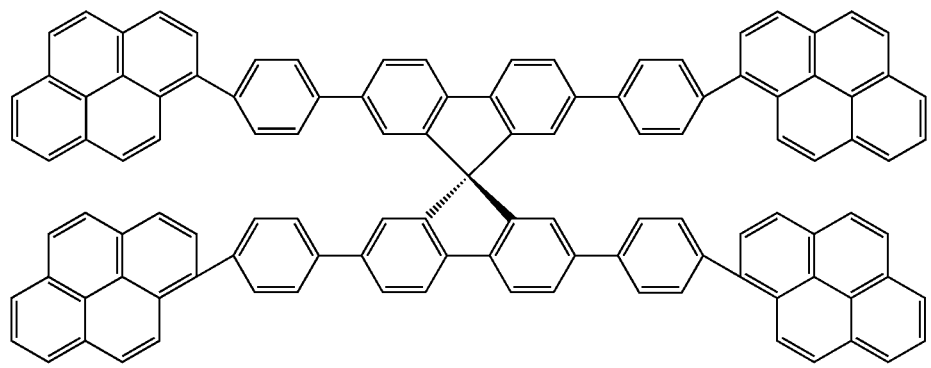
[5]-10

-continued
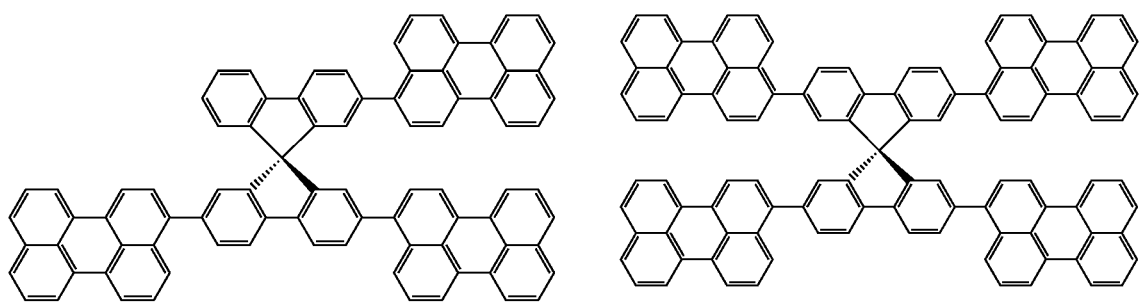
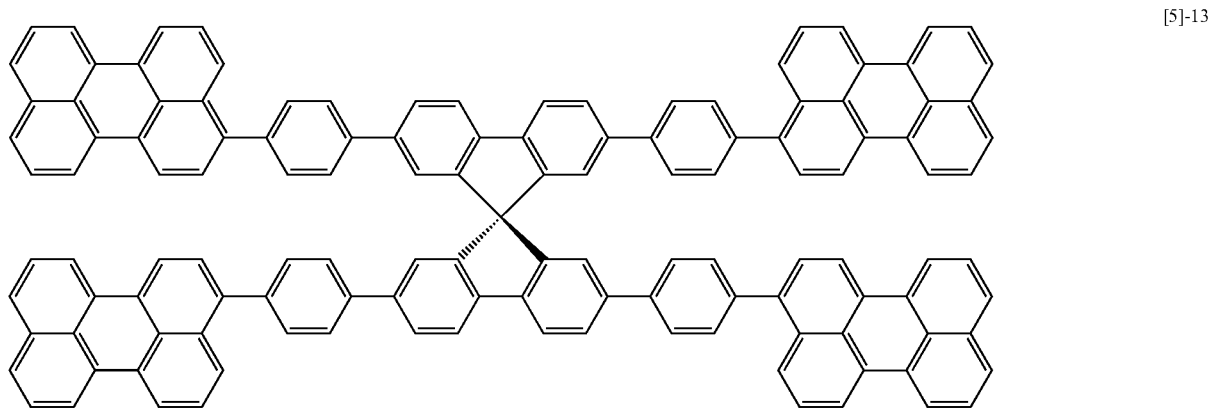
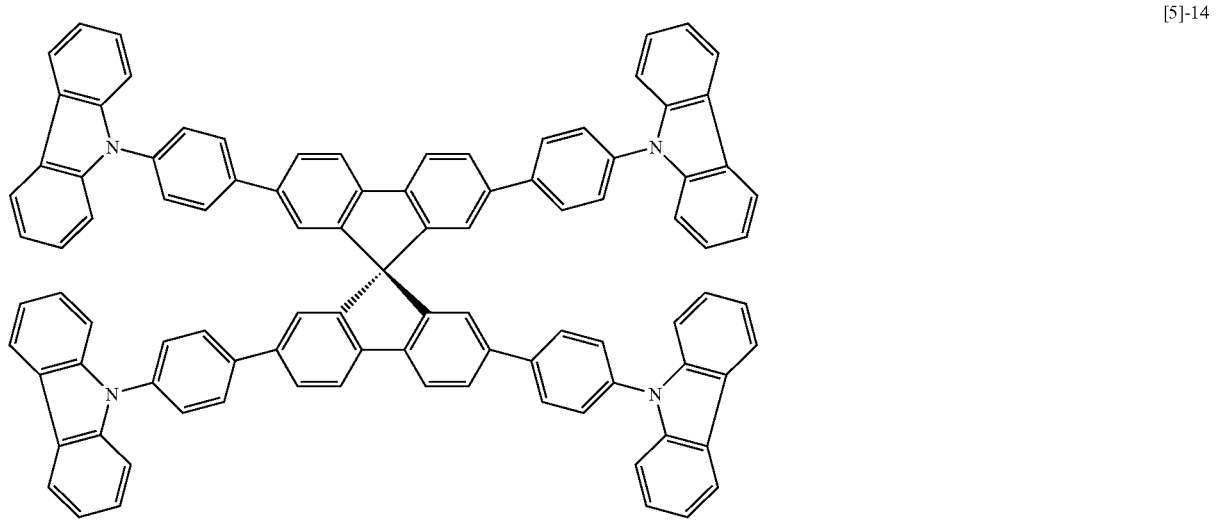
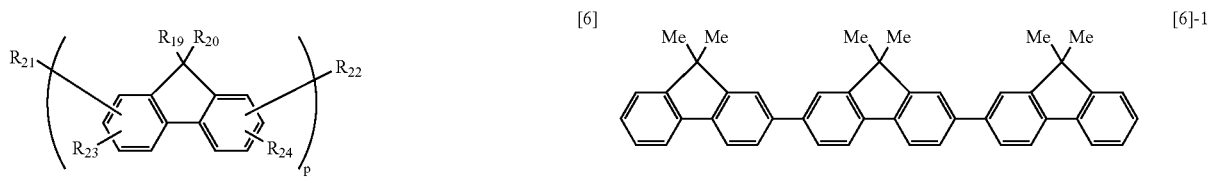
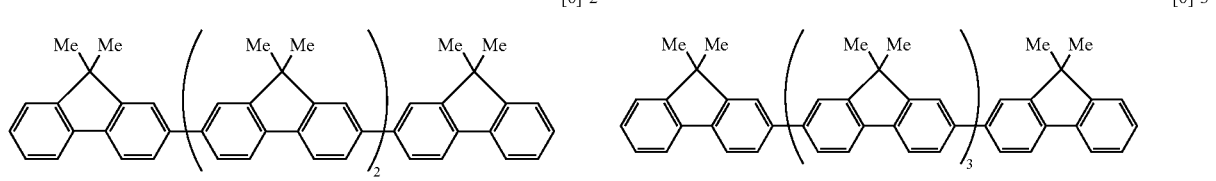

-continued

[6]-4
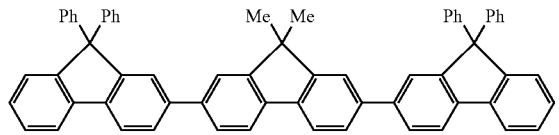

[6]-5
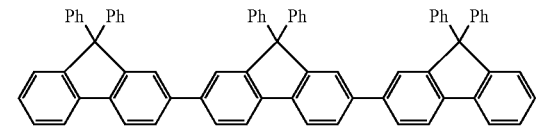

[6]-6
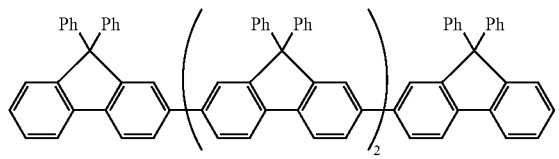

[6]-7
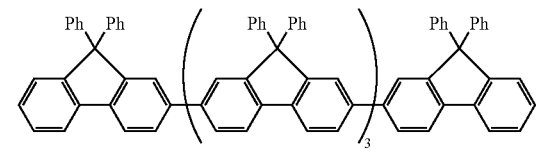

Preferable examples of the organic luminescence device of the present invention are shown in FIGS. 1 to 6.

FIG. 1 is a cross-sectional diagram that illustrates an example of the organic luminescence device of the present invention. In FIG. 1, the device comprises an anode 2, a luminescent layer 3, and a cathode 4, which are formed on a substrate 1 in that order. The luminescence device used herein is useful when it singly has a hole-transporting ability, an electron-transporting ability, and a luminescence property in itself or when it is used in combination with compounds having those characteristics.

Figure 2:
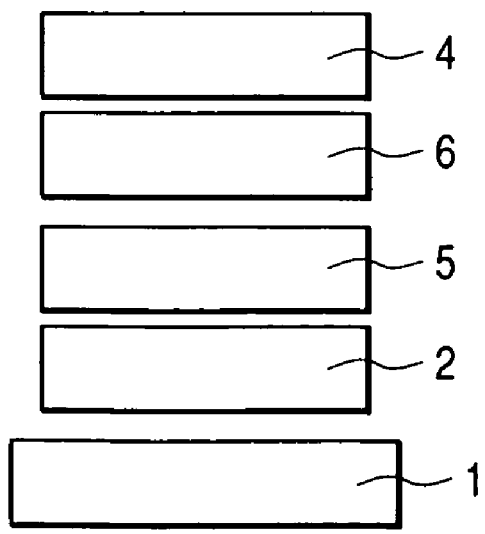
FIG. 2 is a cross-sectional diagram that illustrates another example of the organic luminescence device in accordance with the present invention.

FIG. 2 is a cross-sectional diagram that illustrates another example of the organic luminescence device of the present invention. In FIG. 2, the device comprises an anode 2, a hole-transporting layer 5, an electron-transporting layer 6, and a cathode 4, which are formed on a substrate 1 in that order. In this case, a luminescent material is useful when a material having one or both of a hole-transporting property and an electron-transporting property is used for the respective layers and the luminescent material is used in combination with a hole-transporting material or an electron-transporting material having no luminescence property. In addition, in this case, the luminescent layer 3 is composed of either the hole-transporting layer 5 or the electron-transporting layer 6.

Figure 3:
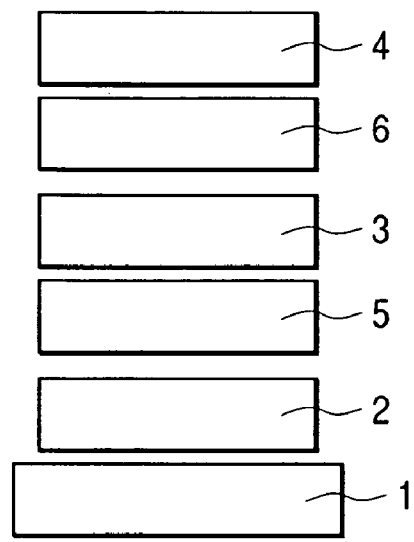
FIG. 3 is a cross-sectional diagram that illustrates another example of the organic luminescence device in accordance with the present invention.

FIG. 3 is a cross-sectional diagram that illustrates another example of the organic luminescence device of the present invention. In FIG. 3, the device comprises an anode 2, a hole-transporting layer 5, a luminescent layer 3, an electron-transporting layer 6, and a cathode 4, which are formed on a substrate 1 in that order. This is one in which a carrier-transporting function and a luminescence function are separated from each other, and is used appropriately in combination with compounds having a hole-transporting property, an electron-transporting property, and a luminescence property, respectively. Thus, the degree of freedom in selecting a material increases extremely. In addition, various kinds of compounds having different luminescent wavelengths can be used. Therefore, it becomes possible to diversify luminescence hue. Furthermore, it also becomes possible to increase the luminescence efficiency by effectively confining each carrier or exciton in the middle luminescent layer 3.

Figure 4:
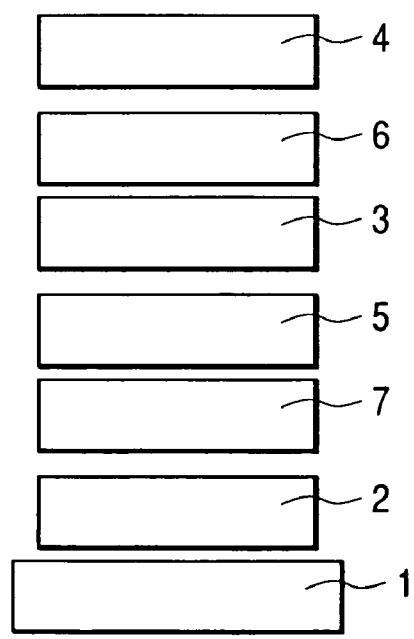
FIG. 4 is a cross-sectional diagram that illustrates another example of the organic luminescence device in accordance with the present invention.

FIG. 4 is a cross-sectional diagram that illustrates another example of the organic luminescence device of the present invention. In FIG. 4, as compared with the example of FIG. 3, the device is constructed such that a hole-injection layer 7 is inserted in the anode 2 side. It is effective in the improvement of an adhesion between the anode 2 and the hole-transporting layer 5 or the improvement of an injection property of holes, so that it is effective in lowering voltage.

Figure 5:
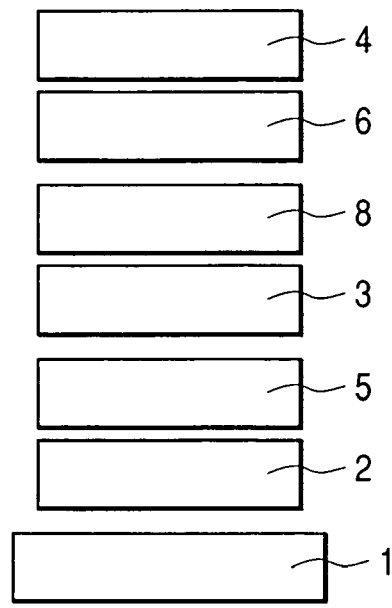
FIG. 5 is a cross-sectional diagram that illustrates another example of the organic luminescence device in accordance with the present invention.
Figure 6:
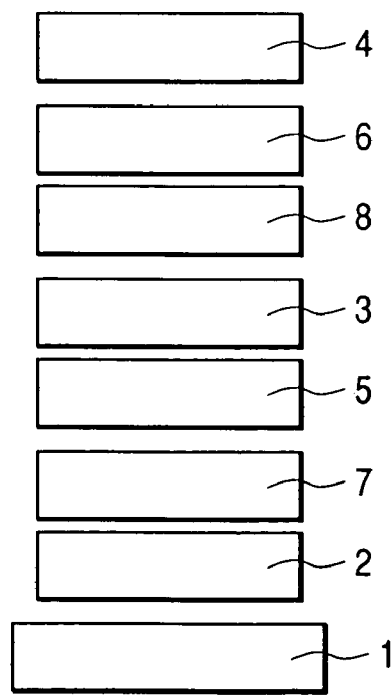
FIG. 6 is a cross-sectional diagram that illustrates another example of the organic luminescence device in accordance with the present invention.

FIGS. 5 and 6 are cross-sectional diagrams that illustrate other examples of the organic luminescence device of the present invention. In each of FIGS. 5 and 6, as compared with the examples of FIGS. 3 and 4, the device is constructed such that a layer (a hole-blocking layer 8) that prevents a hole or an exciton from passing toward the cathode 4 side is inserted between the luminescent layer 3 and the electron-transporting layer 6. The use of a compound having an extremely high ionization-potential as the hole-blocking layer 8 allows a configuration effective to an improvement in luminescence efficiency.

However, in FIGS. 1 to 6, there are shown common basic device configurations. The configuration of the organic luminescence device using the compound of the present invention is not limited thereto. For instance, it is possible to adopt various layer configurations such as one in which an insulating layer is formed at the interface between the electrode and the organic layer, one in which an adhesive layer or an interference layer is formed, and one in which the hole-transporting layer is composed of two layers with different ionization potentials.

The monoamino compound represented by the general formula [1] to be used in the present invention can be used in any modes of FIGS. 1 to 6.

In particular, an organic layer using the compound of the present invention is useful as a luminescent layer, an electron-transporting layer, or a hole-transporting layer. In addition, a layer formed by a vacuum deposition method, a solution-coating method, or the like hardly causes crystallization or the like and is excellent in stability with time.

In the present invention, in particular the monoamino compound represented by the general formula [1] is used as a component of the luminescent layer. However, hole-transporting compounds, luminescent compounds, electron-transporting compounds, or the like, which have been known, may be used together if required.

Examples of those compounds will be given below.
Hole-transporting Compound
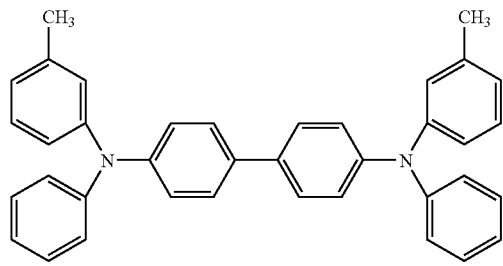
TPD
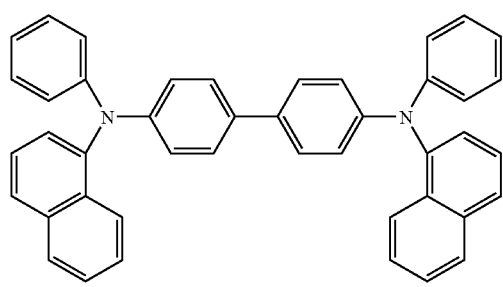
α-NPD
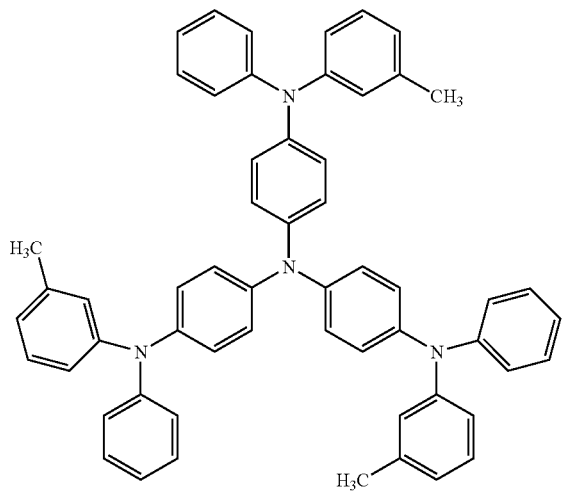
m-MTDATA
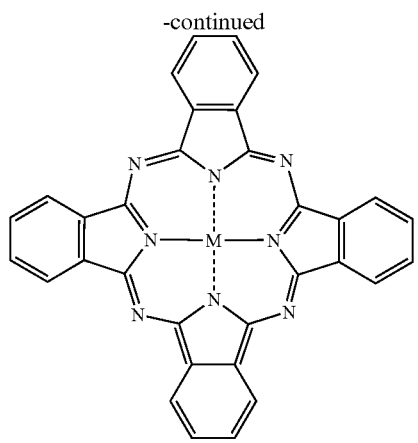
Pc-M
M: Cu, Mg, AlCl, TiO, SiCl$_2$, Zn, Sn, MnCl, GaCl, etc
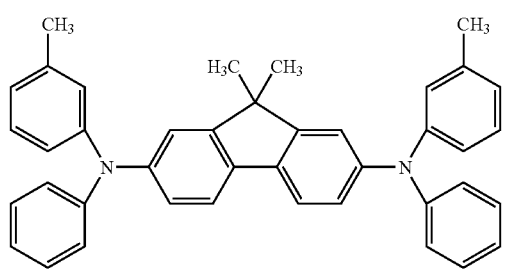
DTDPFL
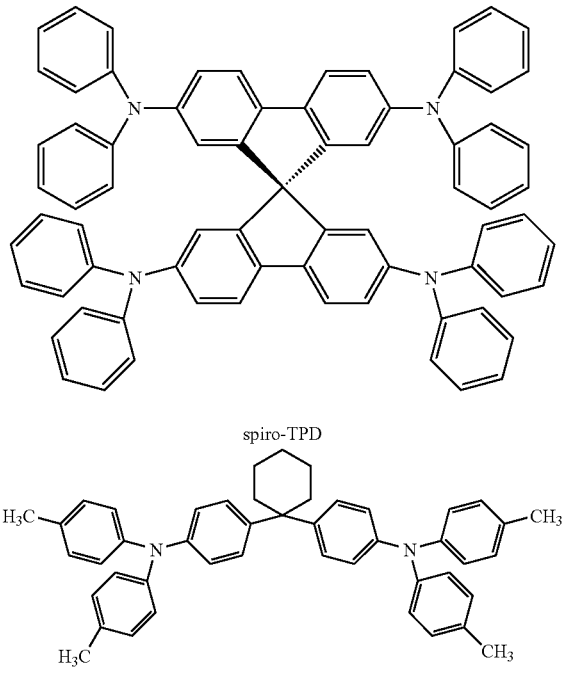
spiro-TPD
TPAC -continued
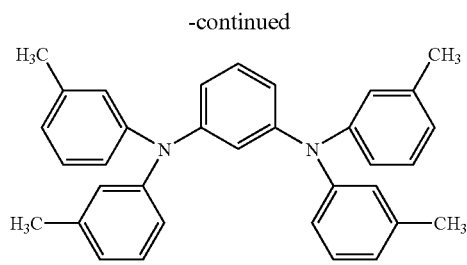
PDA
Electron-transporting Luminescent Material
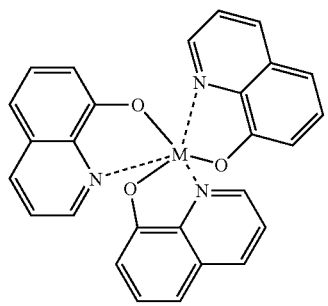
M: Al, Ga
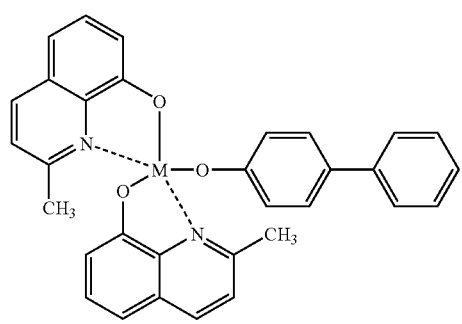
M: Al, Ga
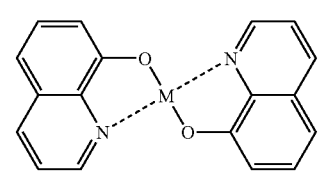
M: Zn, Mg, Be
-continued
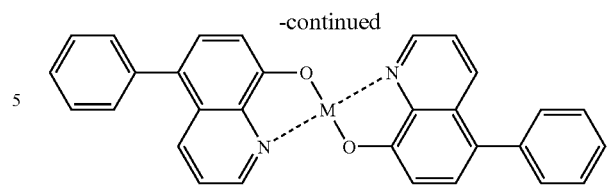
M: Zn, Mg, Be
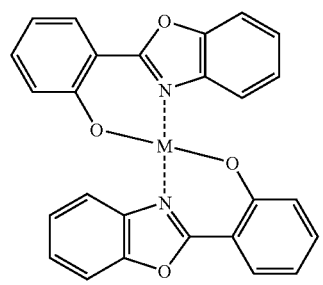
M: Zn, Mg, Be
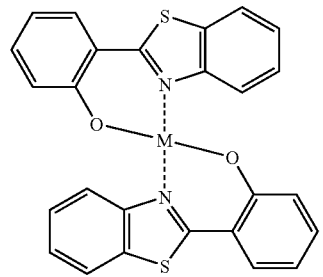
M: Zn, Mg, Be
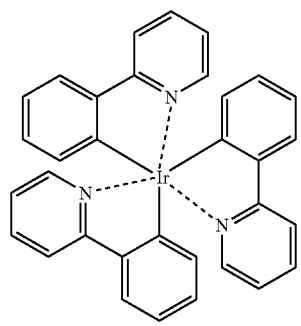

-continued
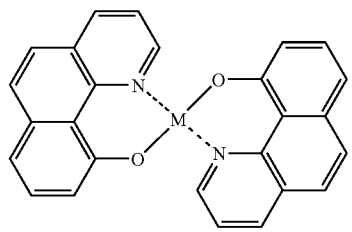
M: Zn, Mg, Be
-continued
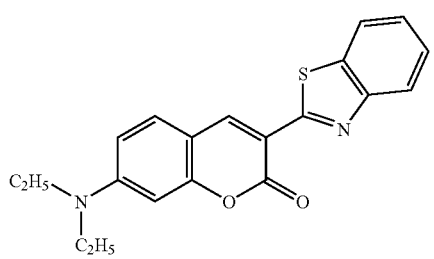
M: Al, Ga
Luminescent Material
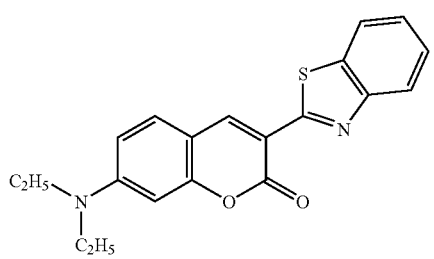
Coumarin6
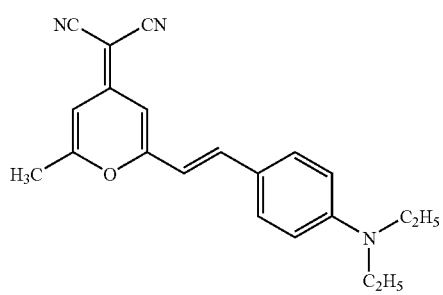
DCM-1
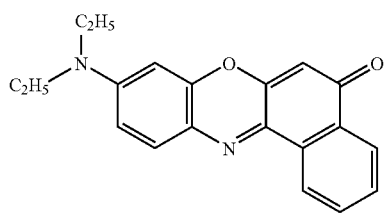
Nile red
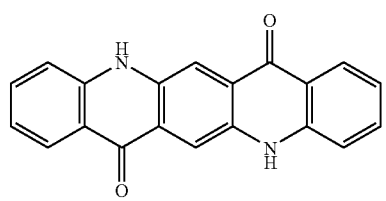
Quinacridone
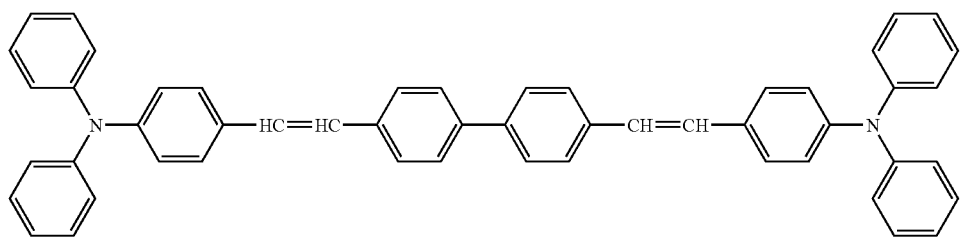
DTPABVi

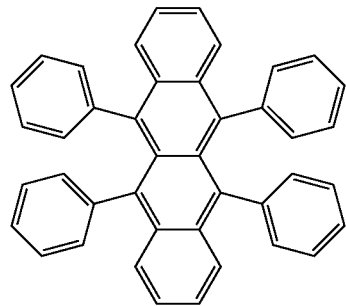
Rubrene
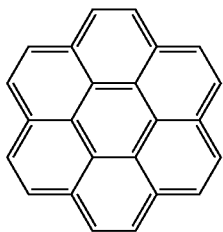
Coronene
Luminescent Layer Matrix Material and Electron-transporting Material
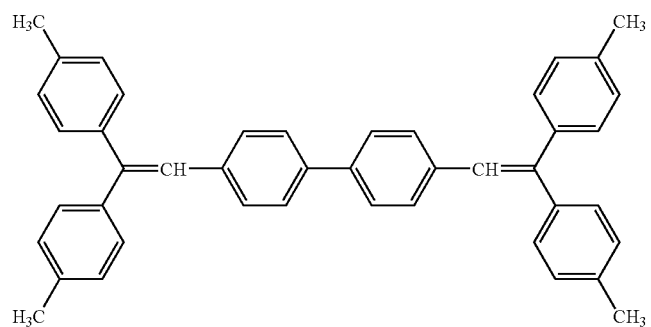
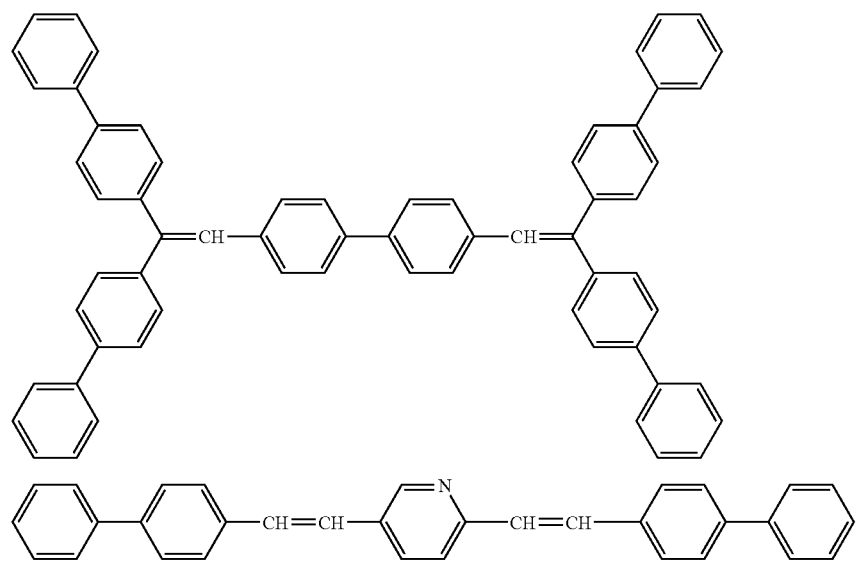

-continued
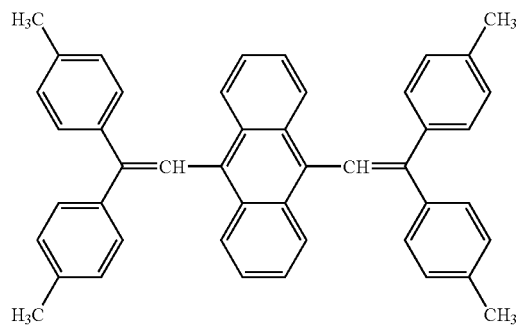
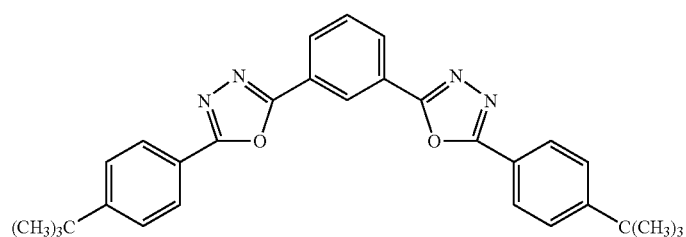
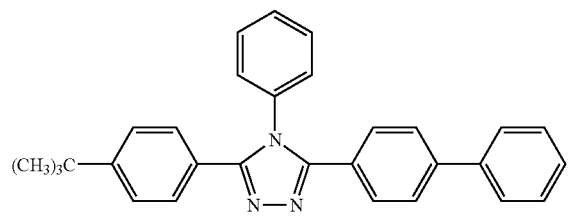
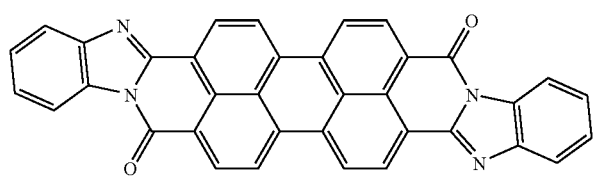
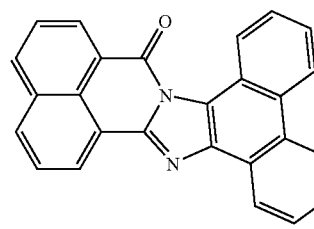
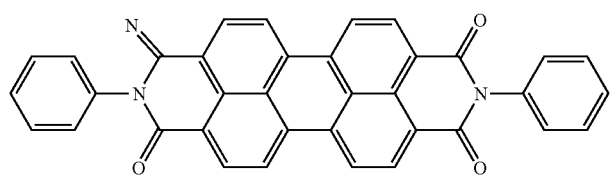
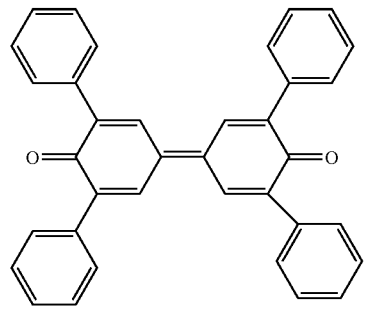

Polymeric Hole-transporting Material
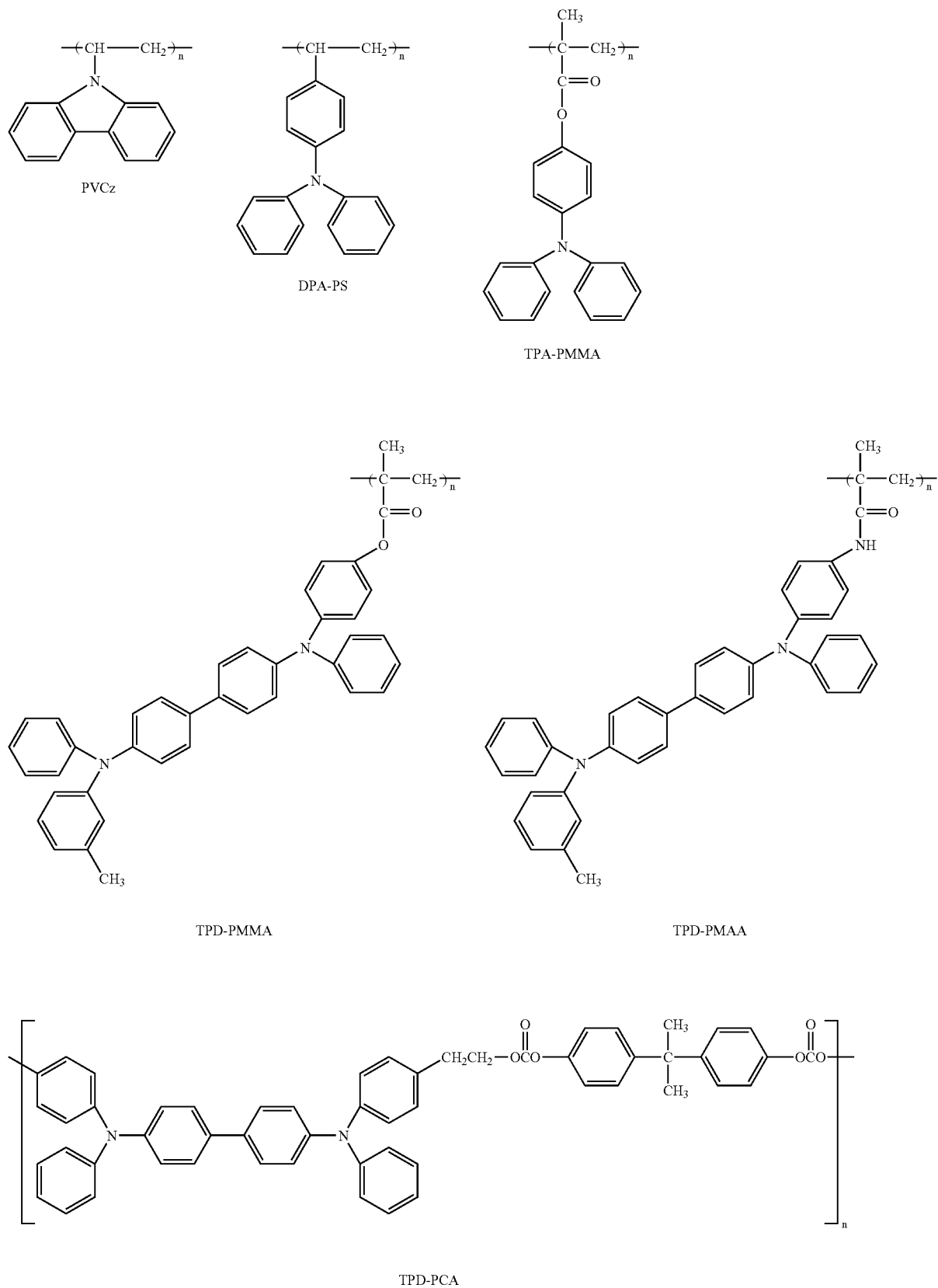

Polymeric Luminescent Material and Charge-transporting Material

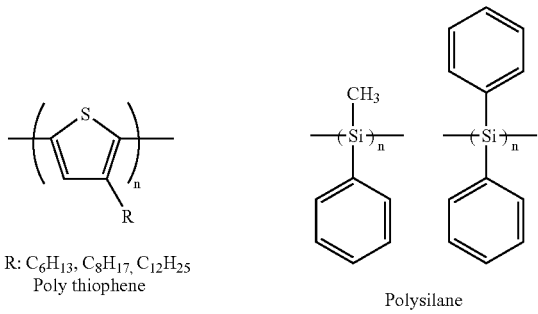
Poly thiophene

Polysilane

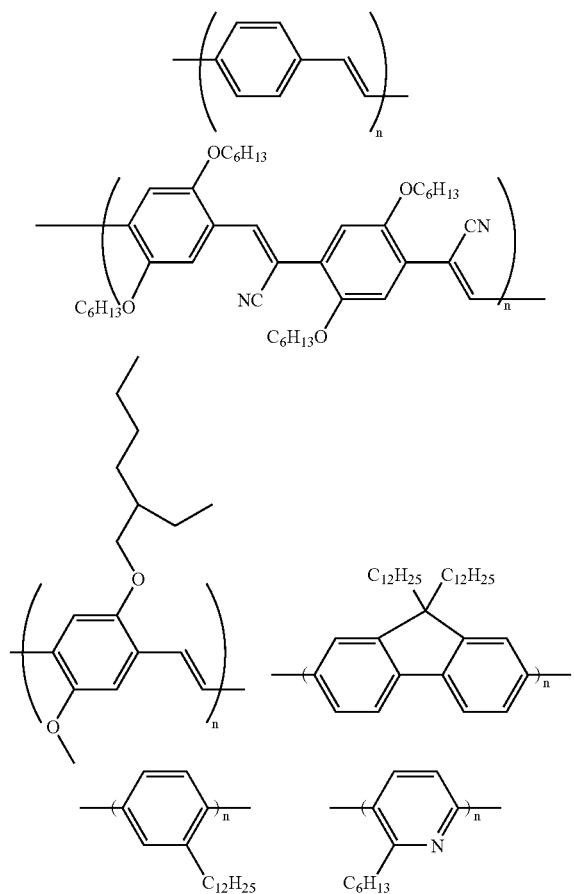

In the organic luminescence device of the invention, the layer containing the monoamino compound represented by the general formula [1] and the layer made of another organic compound are generally formed as thin films by a vacuum deposition method, or by a coating method after being dissolved in an appropriate solvent. In particular, in the case of forming a film with a coating method, the film may be formed in combination with an appropriate binder resin.

The above binder resin can be selected from a wide variety of the binder resins including, for example, polyvinyl carbazole resin, polycarbonate resin, polyester resin, polyarylate resin, polystyrene resin, acrylic resin, methacryl resin, butyral resin, polyvinyl acetal resin, diallyl phthalate resin, phenol resin, epoxy resin, silicone resin, polysulfone resin, and urea resin, although not limited to them. In addition, those resins may be used solely or one or two or more resins may be combined with each other as a copolymer.

The anode material may be one preferably having a large work function. For example, a simple metal substance such as gold, platinum, nickel, palladium, cobalt, selenium, or vanadium, or an alloy thereof, or a metal oxide such as tin oxide, zinc oxide, indium tin oxide (ITO), or indium zinc oxide can be used. In addition, a conductive polymer such as polyaniline, polypyrrole, polythiophene, or polyphenylene sulfide can be also used. Those electrode substances may be used solely or two or more substances may be used together.

On the other hand, the cathode material may be one preferably having a small work function. For example, a simple metal substance such as lithium, sodium, potassium, calcium, magnesium, aluminum, indium, silver, lead, tin, or chromium, or an alloy of plural substances can be used. It is also possible to use a metal oxide such as indium tin oxide (ITO). In addition, the cathode may be constructed as a single layer or may have a multi-layer configuration.

The substance used in the present invention may be, although not particularly limited to, a non-transparent substrate such as a metallic substrate or a ceramic substrate, or a transparent substrate formed of glass, quartz, plastic sheets, or the like. In addition, it is also possible to control the luminescence color by using a color filter film, a fluorescent color-converting filter film, a dielectric reflection film, or the like as a substrate.

Note that, a protective layer or a sealing layer may be formed on the prepared device for preventing the device from contacting with oxygen, moisture, or the like. The protective layer may be a diamond thin film; a film made of an inorganic material such as a metal oxide or a metal nitride; a polymer film made of a fluorocarbon resin, polyparaxylene, polyethylene, a silicone resin, or a polystyrene resin, or the like; or furthermore a photo-curing resin. Furthermore, it is also possible to package the device itself with an appropriate sealing resin while covering it with a glass, a gas-impermeable film, a metal, or the like.

EXAMPLES

Hereinafter, the present invention will be described more specifically with examples. However, the present invention is not limited to those examples.

Example 1

Method of Producing Exemplified Compound No. [1]-38

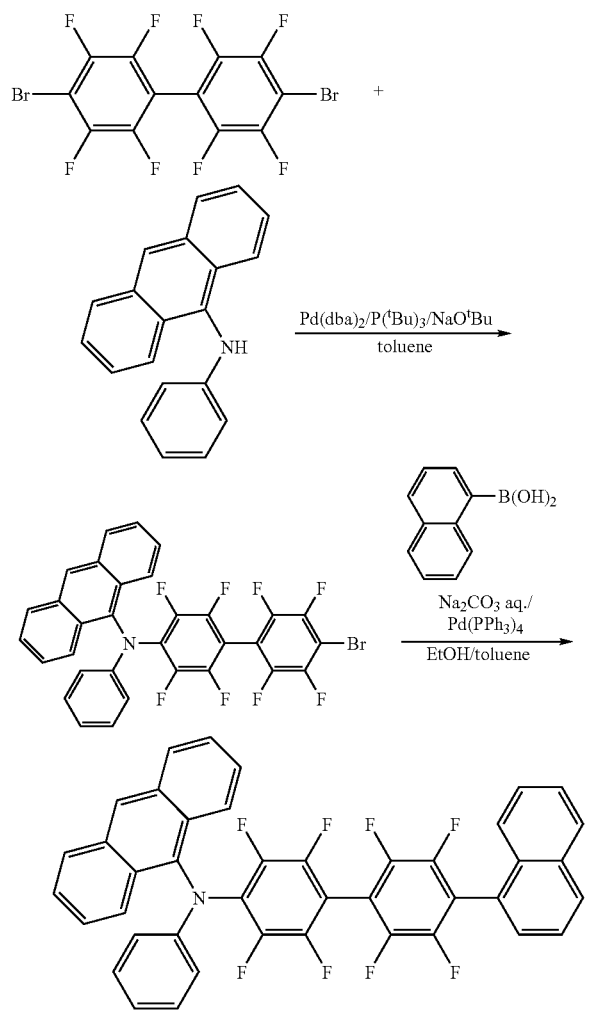

[1]-38

In a nitrogen flow, 160 mg (0.282 mmol) of palladium bis(benzylideneacetone) and 170 mg (0.846 mmol) of tri-tert-butylphosphine were dissolved in 40 ml of toluene and then stirred for 15 minutes at room temperature. Then, 0.58 g (1.27 mmol) of 4,4'-dibromo-2,2',3,3',5,5',6,6'-octafluoro-1,1'-biphenyl dissolved in 50 ml of toluene was dropped into the mixture and it was stirred for 30 minutes. Furthermore, 0.34 g (1.27 mmol) of N-(9-anthracenyl)-N-phenylamine was dissolved in 50 ml of toluene and was then dropped therein, followed by the addition of 0.18 g (1.91 mmol) of sodium tert-butoxide. Then, the mixture was heated and stirred for about 8 hours in an oil bath heated at 120° C. After returning the reaction solution to room temperature, 50 ml of water was added thereto and the resultant solution was then separated into an aqueous layer and an organic layer. Furthermore, the aqueous layer was extracted with toluene and ethyl acetate, and was then combined with the previous organic layer and dried with magnesium sulfate. The solvent was evaporated and then the residue was purified by silica-gel-column chromatography (toluene:hexane=1:2) to obtain 0.55 g of 4-bromo-4'-[N-(9-anthracenyl)-N-phenylamino]-2,2',3,3',5,5',6,6'-octafluoro-1,1'-biphenyl.

In a nitrogen flow, 1 g (1.55 mmol) of 4-bromo-4'-[N-(9-anthracenyl)-N-phenylamino]-2,2',3,3',5,5',6,6'-octafluoro-1,1'-biphenyl and 0.40 g (2.33 mmol) of naphthalene-1-boronic acid were dissolved and stirred in a deaerated mixture solvent of 80 ml of toluene and 40 ml of ethanol, followed by adding 23 ml of a sodium carbonate aqueous solution prepared by dissolving 6 g of anhydrous sodium carbonate in 30 ml of water in a dropwise manner. After stirring the mixture for 30 minutes, 135 mg (0.117 mmol) of tetrakis(triphenylphosphine)palladium was added thereto. Then, the mixture was heated and stirred for about 3 hours in an oil bath heated at 80° C. After returning the reaction solution to room temperature, 40 ml of water and 50 ml of ethyl acetate were added thereto and the resultant solution was then separated into an aqueous layer and an organic layer. Furthermore, the aqueous layer was extracted with toluene and ethyl acetate, and was then combined with the previous organic layer and dried with magnesium sulfate. The solvent was evaporated and then the residue was purified by silicagel-column chromatography (toluene:hexane=1:2) to obtain 0.90 g of the exemplified compound [1]-38.

Example 2

Method of Producing the Exemplified Compound No. [1]-109

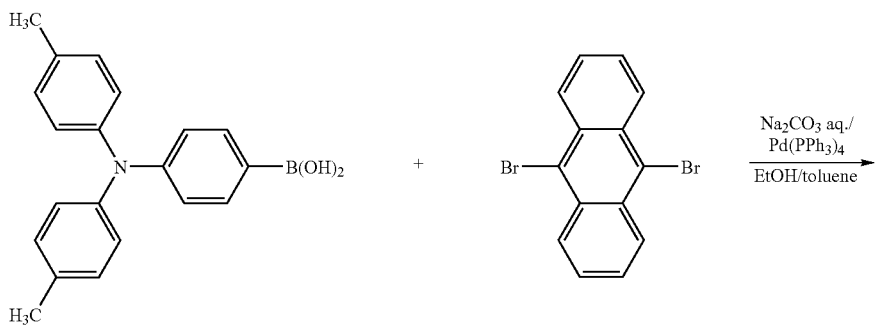

-continued

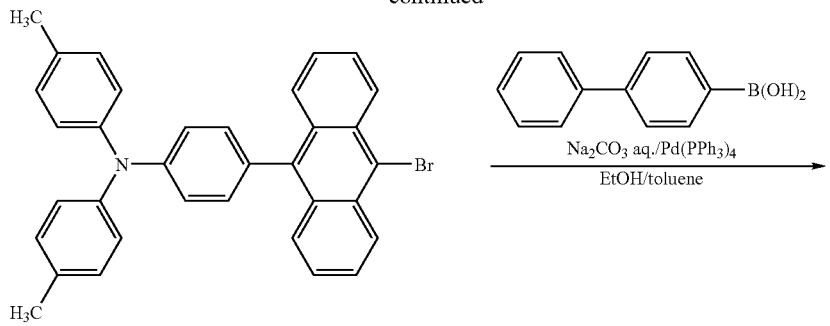

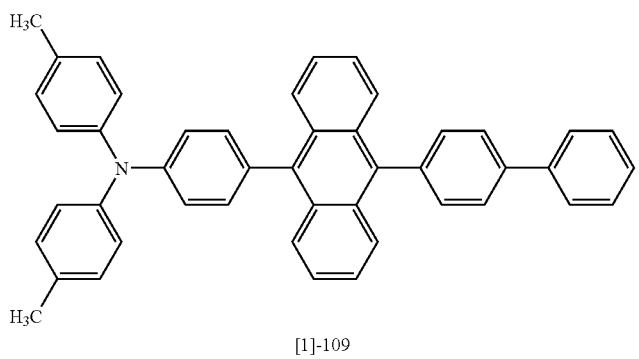

[1]-109

In a nitrogen flow, 1 g (2.98 mmol) of 9,10-dibromoanthracene and 1.44 g (4.46 mmol) of bis(4-methylphenyl)aminobenzene-4-boronic acid were dissolved and stirred in a deaerated mixture solvent of 100 ml of toluene and 50 ml of ethanol, followed by dropping a sodium carbonate aqueous solution prepared by dissolving 9 g of anhydrous sodium carbonate in 45 ml of water. After stirring the mixture for 30 minutes, 257 mg (0.223 mmol) of tetrakis(triphenylphosphine)palladium was added thereto. Then, the mixture was heated and stirred for about 3 hours in an oil bath heated at 80° C. After returning the reaction solution to room temperature, 40 ml of water and 50 ml of ethyl acetate were added thereto and the resultant solution was then separated into an aqueous layer and an organic layer. Furthermore, the aqueous layer was extracted with toluene and ethyl acetate, and was then combined with the previous organic layer and dried with magnesium sulfate. The solvent was evaporated and then the residue was purified by silicagel-column chromatography (toluene:hexane=1:2) to obtain 1.13 g of 9-[bis(4-methylphenyl)amino]phenyl-10-bromoanthracene.

In a nitrogen flow, 1 g (1.89 mmol) of 9-[bis(4-methylphenyl)amino]phenyl-10-bromoanthracene and 0.56 g (2.84 mmol) of 1,1'-bisphenyl-4-boronic acid were dissolved and stirred in a deaerated mixture solvent of 100 ml of toluene and 50 ml of ethanol, followed by dropping a sodium carbonate, aqueous solution prepared by dissolving 6 g of anhydrous sodium carbonate in 30 ml of water. After stirring the mixture for 30 minutes, 164 mg (0.142 mmol) of tetrakis(triphenylphosphine)palladium was added thereto. Then, the mixture was heated and stirred for about 3 hours in an oil bath heated at 80° C. After returning the reaction solution to room temperature, 40 ml of water and 50 ml of ethyl acetate were added thereto and the resultant solution was then separated into an aqueous layer and an organic layer. Furthermore, the aqueous layer was extracted with toluene and ethyl acetate, and was then combined with the previous organic layer and dried with magnesium sulfate. The solvent was, evaporated and then the residue was purified by silicagel-column chromatography (toluene:hexane=1:2) to obtain 1.04 g of the exemplified compound [1]-109.

Example 3

An organic luminescence device constructed as shown in FIG. 3 was produced by a method described below.

A glass substrate provided as a substrate 1, on which a film of indium tin oxide (ITO) of 120 nm in thickness was formed as an anode 2 by a sputtering method, was used as a transparent conductive support substrate. This substrate was sequentially subjected to ultrasonic cleaning with acetone and isopropyl alcohol (IPA), and was then washed with IPA by boiling, followed by drying. Furthermore, one washed with UV/ozone was used as a transparent conductive support substrate.

A chloroform solution was prepared by using a compound represented by the following structural formula as a hole-transporting material so the concentration of the solution would be 0.5% by weight.

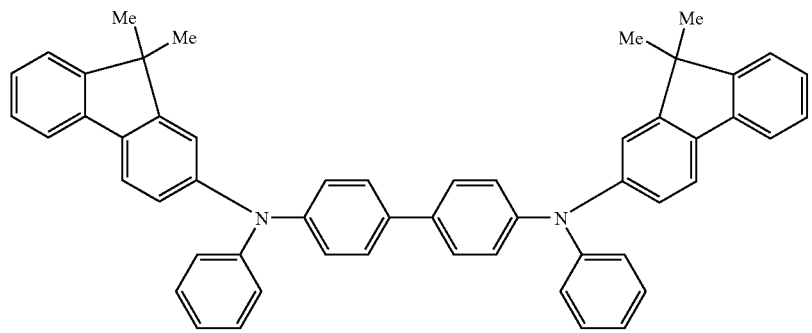

This solution was dropped on the ITO electrode (the anode 2) and was then spin-coated at a rotation speed of 500 RPM for 10 seconds at first and next at a rotation speed of 1000 RPM for 1 minute thereby forming a thin film. Subsequently, it was dried in a vacuum oven at 80° C. for 10 minutes to completely remove the solvent in the thin film. The thickness of the resulting TPD film (the hole-transporting layer 5) was 50 nm.

Then, the above exemplified compound No. [1]-70 and the above exemplified compound No. [2]-50 (weight ratio of 5:100) were deposited together on the hole-transporting layer 5 to form a luminescent layer 3 of 20 nm in thickness. The film formation was performed under the conditions of the degree of vacuum of $1.0 \times 10^{-4}$ Pa and the rate of film formation of 0.2 to 0.3 nm/sec.

Furthermore, aluminum quinolinol (Alq3) was formed into a film of 40 nm in thickness as an electron-transporting layer 6 by a vacuum deposition method. Those organic layers were deposited under the conditions of the degree of vacuum of $1.0 \times 10^{-4}$ Pa and the rate of film formation of 0.2 to 0.3 nm/second.

Next, by using a deposition material made of an aluminum-lithium alloy (a lithium content of 1% by atom), a metal-layer film of 10 nm in thickness was formed on the organic layer described earlier by a vacuum deposition method, and furthermore an aluminum film of 150 nm in thickness was formed thereon by a vacuum deposition method to obtain an organic luminescence device having an aluminum-lithium alloy film as an electron-injecting electrode (a cathode 4). The film formation was performed under the conditions of the degree of vacuum of $1.0 \times 10^{-4}$ Pa and the rate of film formation of 1.0 to 1.2 nm/second at the time of deposition.

The resulting organic EL device was covered with a protective glass plate in an atmosphere of dried air and was sealed with an acrylic resin adhesive so as to prevent the device from being deteriorated by the adsorption of moisture.

When a voltage of 8 V was applied to the device obtained in this way, where the ITO electrode (the anode 2) was provided as a positive electrode and the Al—Li electrode (the cathode 4) was provided as a negative electrode, blue luminescence with a luminescent luminance of 1650 cd/m², a maximum luminance of 5770 cd/m², and a luminescence efficiency of 0.621 m/W was observed.

Examples 4 to 8

Devices were prepared in the same way as that of Example 3 except that the exemplified compounds shown in Table 9 were used in stead of the exemplified compound [1]-70.

TABLE 9

| Example | Exemplified compound No. | Applied voltage (V) | Luminance (cd/m²) | Maximum Luminance (cd/m²) | Efficiency (lm/W) |
|---|---|---|---|---|---|
| 4 | [1]-38 | 8 | 1840 | 6150 | 0.65 |
| 5 | [1]-45 | 8 | 2100 | 7220 | 0.71 |
| 6 | [1]-86 | 9 | 1560 | 4900 | 0.53 |
| 7 | [1]-100 | 8 | 2900 | 8300 | 0.82 |
| 8 | [1]-109 | 8 | 2200 | 7270 | 0.72 |

Example 9

A device was prepared in the same way as that of Example 3 except that the above exemplified compound No. [1]-70 and the above exemplified compound No. [2]-15 (weight ratio of 5:100) were deposited together to form a luminescent layer 3 of 20 nm in thickness.

When a voltage of 9 V was applied on the device obtained in this way, where the ITO electrode (the anode 2) was provided as a positive electrode and the Al—Li electrode (the cathode 4) was provided as a negative electrode, blue luminescence with a luminescent luminance of 1620 cd/m², a maximum luminance of 4850 cd/m², and a luminescence efficiency of 0.55 lm/W was observed.

Example 10

A device was prepared in the same way as that of Example 9 except that the exemplified compound [1]-109 was used in stead of the exemplified compound [1]-70.

When a voltage of 9 V was applied on the device obtained in this way, where the ITO electrode (the anode 2) was provided as a positive electrode and the Al—Li electrode (the cathode 4) was provided as a negative electrode, blue luminescence with a luminescent luminance of 1850 cd/m², a maximum luminance of 6920 cd/m², and a luminescence efficiency of 0.66 lm/W was observed.

Example 11

A device was prepared in the same way as that of Example 3, except that the above exemplified compound No. [1]-70 and the above exemplified compound No. [3]-1 (weight ratio of 5:100) were deposited together to form a luminescent layer 3 of 20 nm in thickness.

When a voltage of 8 V was applied on the device obtained in this way, where the ITO electrode (the anode 2) was provided as a positive electrode and the Al—Li electrode (the cathode 4) was provided as a negative electrode, blue luminescence with a luminescent luminance of 1810 cd/m$^2$, a maximum luminance of 6980 cd/m$^2$, and a luminescence efficiency of 0.70 lm/W was observed.

Example 12

A device was prepared in the same way as that of Example 11, except that the exemplified compound [1]-75 was used in stead of the exemplified compound [1]-70.

When a voltage of 8 V was applied on the device obtained in this way, where the ITO electrode (the anode 2) was provided as a positive electrode and the Al—Li electrode (the cathode 4) was provided as a negative electrode, blue luminescence with a luminescent luminance of 1870 cd/m$^2$, a maximum luminance of 7050 cd/m$^2$, and a luminescence efficiency of 0.73 lm/W was observed.

Example 13

A device was prepared in the same way as that of Example 3, except that the above exemplified compound No. [1]-38 and the above exemplified compound No. [4]-1 (weight ratio of 5:100) were deposited together to form a luminescent layer 3 of 20 nm in thickness.

When a voltage of 8 V was applied on the device obtained in this way, where the ITO electrode (the anode 2) was provided as a positive electrode and the Al—Li electrode (a cathode 4) was provided as a negative electrode, blue luminescence with a luminescent luminance of 2180 cd/m$^2$, a maximum luminance of 7560 cd/m$^2$, and a luminescence efficiency of 0.80 lm/W was observed.

Example 14

A device was prepared in the same way as that of Example 3, except that the above exemplified compound No. [1]-70 and the above exemplified compound No. [5]-2 (weight ratio of 5:100) were deposited together to form a luminescent layer 3 of 20 nm in thickness.

When a voltage of 8 V was applied on the device obtained in this way, where the ITO electrode (the anode 2) was provided as a positive electrode and the Al—Li electrode (the cathode 4) was provided as a negative electrode, blue luminescence with a luminescent luminance of 2800 cd/m$^2$, a maximum luminance of 7950 cd/m$^2$, and a luminescence efficiency of 0.85 lm/W was observed.

Example 15

A device was prepared in the same way as that of Example 3, except that the above exemplified compound No. [1]-109 and the above exemplified compound No. [5]-9 (weight ratio of 5:100) were deposited together to form a luminescent layer 3 of 20 nm in thickness.

When a voltage of 8 V was applied on the device obtained in this way, where the ITO electrode (the anode 2) was provided as a positive electrode and the Al—Li electrode (the cathode 4) was provided as a negative electrode, blue luminescence with a luminescent luminance of 4250 cd/m$^2$, a maximum luminance of 8230 cd/m$^2$, and a luminescence efficiency of 1.08 lm/W was observed.

Example 16

A device was prepared in the same way as that of Example 3, except that the above exemplified compound No. [1]-86 and the above exemplified compound No. [6]-1 (weight ratio of 5:100) were deposited together to form a luminescent layer 3 of 20 nm in thickness.

When a voltage of 9 V was applied on the device obtained in this way, where the ITO electrode (the anode 2) was provided as a positive electrode and the Al—Li electrode (the cathode 4) was provided as a negative electrode, blue luminescence with a luminescent luminance of 1420 cd/m$^2$, a maximum luminance of 3870 cd/m$^2$, and a luminescence efficiency of 0.48 lm/W was observed.

Example 17

A device was prepared in the same way as that of Example 3, except that the above exemplified compound No. [1]-70 was deposited to form a luminescent layer 3 of 20 nm in thickness.

When a voltage of 8 V was applied on the device obtained in this way, where the ITO electrode (the anode 2) was provided as a positive electrode and the Al—Li electrode (the cathode 4) was provided as a negative electrode, blue luminescence with a luminescent luminance of 720 cd/m$^2$, a maximum luminance of 4830 cd/m$^2$, and a luminescence efficiency of 0.50 lm/W was observed.

Examples 18-23

The luminescence spectrums of the devices prepared in Examples 3, 10, 12, 13, 14, and 15 were observed by means of MCPD-7000 and CIE-chromaticity coordinates thereof were measured. The results are shown in Table 10.

TABLE 10

| Example | Example of device | CIE-chromaticity coordinates (x, y) |
|---------|-------------------|-------------------------------------|
| 18      | 3                 | 0.15, 0.09                          |
| 19      | 10                | 0.15, 0.10                          |
| 20      | 12                | 0.15, 0.10                          |
| 21      | 13                | 0.15, 0.11                          |
| 22      | 14                | 0.16, 0.10                          |
| 23      | 15                | 0.15, 0.11                          |

Example 24

When a voltage was applied to the device prepared in Example 15 in an atmosphere of nitrogen for 100 hours while retaining a current density at 7.0 mA/cm$^2$, an initial luminance of 510 cd/m$^2$ changed to a luminance of 450 cd/m$^2$ after 100 hours, indicating small deterioration of luminance.

Comparative Example 1

A device was prepared in the same way as that of Example 3 except that the following styryl compound was used as a luminescent layer 3.

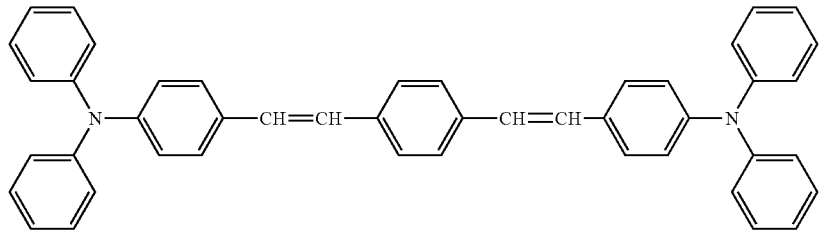

When a voltage of 10 V was applied on the device obtained in this way, where the ITO electrode (the anode 2) was provided as a positive electrode and the Al—Li electrode (the cathode 4) was provided as a negative electrode, green-tinged bluish white luminescence with a luminescent luminance of 120 cd/m$^2$, a maximum luminance of 3800 cd/m$^2$, and a luminescence efficiency of 0.17 lm/W was observed.

Comparative Example 2

A device was prepared in the same way as that of Example 1, except that the above styryl compound and the above exemplified compound No. [4]-1 (weight ratio of 5:100) were deposited together to form a luminescent layer 3 of 20 nm in thickness.

When a voltage of 10 V was applied on the device obtained in this way, where the ITO electrode (the anode 2) was provided as a positive electrode and the Al—Li electrode (the cathode 4) was provided as a negative electrode, green-tinged bluish white luminescence with a luminescent luminance of 125 cd/m$^2$, a maximum luminance of 4500 cd/m$^2$, and a luminescence efficiency of 0.30 lm/W was observed.

Comparative Example 3

The luminescence spectrum of the device prepared in Comparative Example 2 was observed by means of MCPD-7000 and CIE-chromaticity coordinates thereof were measured. As a result, (x, y)=(0, 16, 0, 30) was obtained.

As described above with reference to the embodiments and examples, the organic luminescence device using the monoamino compound represented by the general formula [1] of the present invention obtains, as a single layer or a mixed layer of dopant/host, luminescence with a high luminance at a low applied voltage, and also the color purity and durability thereof are excellent.

Furthermore, the device can be prepared by using a vapor-deposition method, a casting method, or the like, and the device having a large area can be easily prepared at a comparatively low cost.

The invention claimed is:

1. An organic luminescence device comprising at least a pair of electrodes including an anode and a cathode and one or a plurality of layers containing an organic compound sandwiched between the pair of electrodes, wherein at least one of the layers containing the organic compound contains at least one of compounds represented by the following general formula [1]:

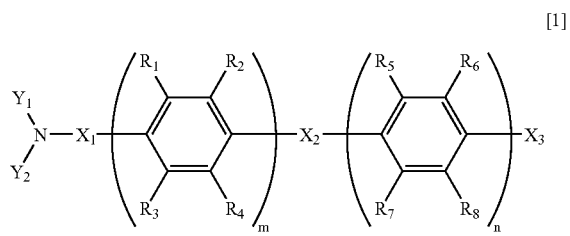

[1]

(wherein $X_1$ and $X_2$ represent divalent groups respectively selected from the group consisting of a substituted or unsubstituted alkylene group, aralkylene group, arylene group and heterocyclic group; and an alkylene group, an aralkylene group, an alkenylene group, an amino group, a silyl group, a carbonyl group, an ether group and a thioether group, each of which has a coupling group including a substituted or unsubstituted arylene group or a divalent heterocyclic group, in which $X_1$ and $X_2$ may be identical with or different from each other, and also $X_1$ and $X_2$ may be directly bonded with each other;

$X_3$ represents a group selected from the group consisting of substituted or unsubstituted alkyl group, aralkyl group, aryl group, and heterocyclic group, in which $X_3$ may be identical with or different from $X_1$ or $X_2$ and in which the substituent is selected from the group consisting of alkyl, benzyl, phenethyl, aralkyl, alkoxy, phenoxy, 4-butylphenoxy, benzyloxy, phenyl, alkylphenyl, chlorophenyl, biphenyl, terphenyl, naphthyl, anthryl, phenanthryl, pyrenyl, heterocyclic, halogen, cyano, and nitro;

$Y_1$ and $Y_2$ represent groups respectively from the group consisting of a substituted or unsubstituted alkyl group, aralkyl group, aryl group and heterocyclic group; a substituted or unsubstituted alkylene group, aralkylene group, alkenylene group, amino group, and silyl group, each of which has a coupling group including a substituted or unsubstituted arylene group or a divalent heterocyclic group; and an unsubstituted carbonyl group, ether group, and thioether group, each of which has a coupling group including a substituted unsubstituted arylene group or a divalent heterocyclic group, in which $Y_1$ and $Y_2$ may be identical with or different from each other;

$Y_1$ and $Y_2$, or $X_1$, $Y_1$ and $Y_2$ may be bonded with each other to form a ring;

$R_1$ to $R_8$ represent groups respectively selected from the group consisting of a hydrogen atom, a halogen group, and a substituted or unsubstituted alkyl group, aralkyl group, and aryl group, in which $R_1$ to $R_8$ may be identical with or different from each other; and m+n denotes an integer number of 1 to 10, wherein the layer containing the compound represented by the general formula [1] contains at least one of the compounds represented by the following general formula [2]:

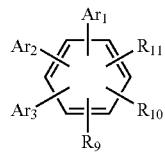
[2]

(wherein $Ar_1$ to $Ar_3$ represent groups respectively selected from the group consisting of a substituted or unsubstituted aryl group and heterocyclic group, in which $Ar_1$ to $Ar_3$ may be identical with or different from each other, or one of them may be a hydrogen atom, a substituted or unsubstituted alkyl group, or a substituted or unsubstituted aralkyl group; and $R_9$ to $R_{11}$ represent groups respectively selected from the group consisting of a hydrogen atom, a halogen group, substituted or unsubstituted alkyl group and aralkyl group, a substituted amino group, and a cyano group).

2. An organic luminescence device comprising at least a pair of electrodes including an anode and a cathode and one or a plurality of layers containing an organic compound sandwiched between the pair of electrodes, wherein at least one of the layers containing the organic compound contains at least one of compounds represented by the following general formula [1]:

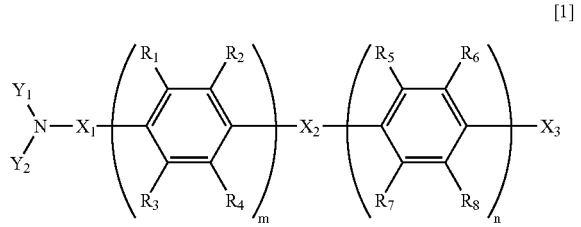
[1]

(wherein $X_1$ and $X_2$ represent divalent groups respectively selected from the group consisting of a substituted or unsubstituted alkylene group, aralkylene group, arylene group and heterocyclic group; and an alkylene group, an aralkylene group, an alkenylene group, an amino group, a silyl group, a carbonyl group, an ether group and a thioether group, each of which has a coupling group including a substituted or unsubstituted arylene group or a divalent heterocyclic group, in which $X_1$ and $X_2$ may be identical with or different from each other, and also $X_1$ and $X_2$ may be directly bonded with each other;

$X_3$ represents a group selected from the group consisting of substituted or unsubstituted alkyl group, aralkyl group, aryl group, and heterocyclic group, in which $X_3$ may be identical with or different from $X_1$ or $X_2$ and in which the substituent is selected from the group consisting of alkyl, benzyl, phenethyl, aralkyl, alkoxy, phenoxy, 4-butylphenoxy, benzyloxy, phenyl, alkylphenyl, chlorophenyl, biphenyl, terphenyl, naphthyl, anthryl, phenanthryl, pyrenyl, heterocyclic, halogen, cyano, and nitro;

$Y_1$ and $Y_2$ represent groups respectively from the group consisting of a substituted or unsubstituted alkyl group, aralkyl group, aryl group and heterocyclic group; a substituted or unsubstituted alkylene group, aralkylene group, alkenylene group, amino group, and silyl group, each of which has a coupling group including a substituted or unsubstituted arylene group or a divalent heterocyclic group; and an unsubstituted carbonyl group, ether group, and thioether group, each of which has a coupling group including a substituted unsubstituted arylene group or a divalent heterocyclic group, in which $Y_1$ and $Y_2$ may be identical with or different from each other;

$Y_1$ and $Y_2$, or $X_1$, $Y_1$ and $Y_2$ may be bonded with each other to form a ring;

$R_1$ to $R_8$ represent groups respectively selected from the group consisting of a hydrogen atom, a halogen group, and a substituted or unsubstituted alkyl group, aralkyl group, and aryl group, in which $R_1$ to $R_8$ may be identical with or different from each other; and m+n denotes an integer number of 1 to 10, wherein the layer containing the compound represented by the general formula [1] contains at least one of the compounds represented by the following general formula [3]:

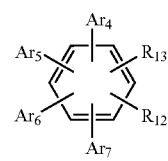
[3]

(wherein $Ar_4$ to $Ar_7$ represent groups respectively selected from the group consisting of a substituted or unsubstituted aryl group and heterocyclic group, in which $Ar_4$ to $Ar_7$ may be identical with or different from each other; and $R_{12}$ and $R_{13}$ represent groups selected from the group consisting of a hydrogen atom, a halogen group, substituted or unsubstituted alkyl group and aralkyl group, a substituted amino group, and a cyano group).

3. An organic luminescence device comprising at least a pair of electrodes including an anode and a cathode and one or a plurality of layers containing an organic compound sandwiched between the pair of electrodes, wherein at least one of the layers containing the organic compound contains at least one of compounds represented by the following general formula [1]:

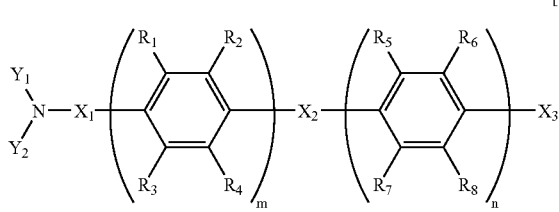
[1]

(wherein $X_1$ and $X_2$ represent divalent groups respectively selected from the group consisting of a substituted or unsubstituted alkylene group, aralkylene group, arylene group and heterocyclic group; and an alkylene group, an aralkylene group, an alkenylene group, an amino group, a silyl group, a carbonyl group, an ether group and a thioether group, each of which has a coupling group including a substituted or unsubstituted arylene group or a divalent heterocyclic group, in which $X_1$ and $X_2$ may be identical with or different from each other, and also $X_1$ and $X_2$ may be directly bonded with each other;

$X_3$ represents a group selected from the group consisting of substituted or unsubstituted alkyl group, aralkyl group, aryl group, and heterocyclic group, in which $X_3$ may be identical with or different from $X_1$ or $X_2$ and in which the substituent is selected from the group consisting of alkyl, benzyl, phenethyl, aralkyl, alkoxy, phenoxy, 4-butylphenoxy, benzyloxy, phenyl, alkylphenyl, chlorophenyl, biphenyl, terphenyl, naphthyl, anthryl, phenanthryl, pyrenyl, heterocyclic, halogen, cyano, and nitro;

$Y_1$ and $Y_2$ represent groups respectively from the group consisting of a substituted or unsubstituted alkyl group, aralkyl group, aryl group and heterocyclic group; a substituted or unsubstituted alkylene group, aralkylene group, alkenylene group, amino group, and silyl group, each of which has a coupling group including a substituted or unsubstituted arylene group or a divalent heterocyclic group; and an unsubstituted carbonyl group, ether group, and thioether group, each of which has a coupling group including a substituted unsubstituted arylene group or a divalent heterocyclic group, in which $Y_1$ and $Y_2$ may be identical with or different from each other;

$Y_1$ and $Y_2$, or $X_1$, $Y_1$ and $Y_2$ may be bonded with each other to form a ring;

$R_1$ to $R_8$ represent groups respectively selected from the group consisting of a hydrogen atom, a halogen group, and a substituted or unsubstituted alkyl group, aralkyl group, and aryl group, in which $R_1$ to $R_8$ may be identical with or different from each other; and m+n denotes an integer number of 1 to 10, wherein the layer containing the compound represented by the general formula [1] contains at least one of the compounds represented by the following general formula [4]:

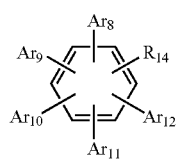

[4]

(wherein $Ar_8$ to $Ar_{12}$ represent groups respectively selected from the group consisting of a substituted or unsubstituted aryl group and heterocyclic group, in which $Ar_8$ to $Ar_{12}$ may be identical with or different from each other; and $R_{14}$ represents a group selected from the group consisting of a hydrogen atom, a halogen group, substituted or unsubstituted alkyl group, aralkyl group, aryl group and heterocyclic group, a substituted amino group, and a cyano group).

4. An organic luminescence device comprising at least a pair of electrodes including an anode and a cathode and one or a plurality of layers containing an organic compound sandwiched between the pair of electrodes, wherein at least one of the layers containing the organic compound contains at least one of compounds represented by the following general formula [1]:

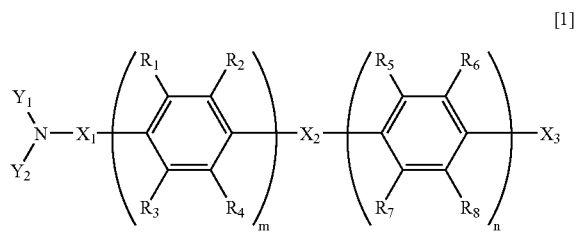

[1]

(wherein $X_1$ and $X_2$ represent divalent groups respectively selected from the group consisting of a substituted or unsubstituted alkylene group, aralkylene group, arylene group and heterocyclic group; and an alkylene group, an aralkylene group, an alkenylene group, an amino group, a silyl group, a carbonyl group, an ether group and a thioether group, each of which has a coupling group including a substituted or unsubstituted arylene group or a divalent heterocyclic group, in which $X_1$ and $X_2$ may be identical with or different from each other, and also $X_1$ and $X_2$ may be directly bonded with each other;

$X_3$ represents a group selected from the group consisting of substituted or unsubstituted alkyl group, aralkyl group, aryl group, and heterocyclic group, in which $X_3$ may be identical with or different from $X_1$ or $X_2$ and in which the substituent is selected from the group consisting of alkyl, benzyl, phenethyl, aralkyl, alkoxy, phenoxy, 4-butylphenoxy, benzyloxy, phenyl, alkylphenyl, chlorophenyl, biphenyl, terphenyl, naphthyl, anthryl, phenanthryl, pyrenyl, heterocyclic, halogen, cyano, and nitro;

$Y_1$ and $Y_2$ represent groups respectively from the group consisting of a substituted or unsubstituted alkyl group, aralkyl group, aryl group and heterocyclic group; a substituted or unsubstituted alkylene group, aralkylene group, alkenylene group, amino group, and silyl group, each of which has a coupling group including a substituted or unsubstituted arylene group or a divalent heterocyclic group; and an unsubstituted carbonyl group, ether group, and thioether group, each of which has a coupling group including a substituted unsubstituted arylene group or a divalent heterocyclic group, in which $Y_1$ and $Y_2$ may be identical with or different from each other;

$Y_1$ and $Y_2$, or $X_1$, $Y_1$ and $Y_2$ may be bonded with each other to form a ring;

$R_1$ to $R_8$ represent groups respectively selected from the group consisting of a hydrogen atom, a halogen group, and a substituted or unsubstituted alkyl group, aralkyl group, and aryl group, in which $R_1$ to $R_8$ may be identical with or different from each other; and m+n denotes an integer number of 1 to 10, wherein the layer containing the compound represented by the general formula [1] contains at least one of the compounds represented by the following general formula [5]:

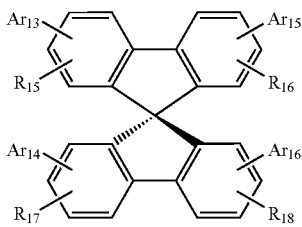

(wherein $Ar_{13}$ to $Ar_{16}$ represent groups respectively selected from the group consisting of a substituted or unsubstituted aryl group and heterocyclic group, in which $Ar_{13}$ to $Ar_{16}$ may be identical with or different from each other, or at most three of $Ar_{13}$ to $Ar_{16}$ may be a hydrogen atom, a substituted or unsubstituted alkyl group, or a substituted or unsubstituted aralkyl group; and $R_{15}$ to $R_{18}$ represent groups respectively selected from the group consisting of a hydrogen atom, a halogen group, substituted or unsubstituted alkyl group, aralkyl group, aryl group and heterocyclic group, a substituted amino group, and a cyano group).

5. An organic luminescence device comprising at least a pair of electrodes including an anode and a cathode and one or a plurality of layers containing an organic compound sandwiched between the pair of electrodes, wherein at least one of the layers containing the organic compound contains at least one of compounds represented by the following general formula [1]:

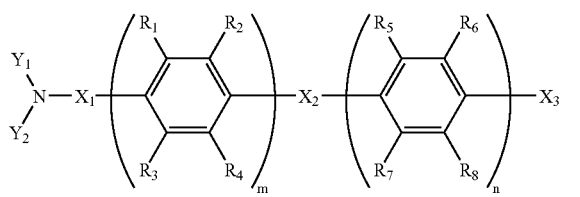

(wherein $X_1$ and $X_2$ represent divalent groups respectively selected from the group consisting of a substituted or unsubstituted alkylene group, aralkylene group, arylene group and heterocyclic group; and an alkylene group, an aralkylene group, an alkenylene group, an amino group, a silyl group, a carbonyl group, an ether group and a thioether group, each of which has a coupling group including a substituted or unsubstituted arylene group or a divalent heterocyclic group, in which $X_1$ and $X_2$ may be identical with or different from each other, and also $X_1$ and $X_2$ may be directly bonded with each other;

$X_3$ represents a group selected from the group consisting of substituted or unsubstituted alkyl group, aralkyl group, aryl group, and heterocyclic group, in which $X_3$ may be identical with or different from $X_1$ or $X_2$ and in which the substituent is selected from the group consisting of alkyl, benzyl, phenethyl, aralkyl, alkoxy, phenoxy, 4-butylphenoxy, benzyloxy, phenyl, alkylphenyl, chlorophenyl, biphenyl, terphenyl, naphthyl, anthryl, phenanthryl, pyrenyl, heterocyclic, halogen, cyano, and nitro;

$Y_1$ and $Y_2$ represent groups respectively from the group consisting of a substituted or unsubstituted alkyl group, aralkyl group, aryl group and heterocyclic group; a substituted or unsubstituted alkylene group, aralkylene group, alkenylene group, amino group, and silyl group, each of which has a coupling group including a substituted or unsubstituted arylene group or a divalent heterocyclic group; and an unsubstituted carbonyl group, ether group, and thioether group, each of which has a coupling group including a substituted unsubstituted arylene group or a divalent heterocyclic group, in which $Y_1$ and $Y_2$ may be identical with or different from each other;

$Y_1$ and $Y_2$, or $X_1$, $Y_1$ and $Y_2$ may be bonded with each other to form a ring;

$R_1$ to $R_8$ represent groups respectively selected from the group consisting of a hydrogen atom, a halogen group, and a substituted or unsubstituted alkyl group, aralkyl group, and aryl group, in which $R_1$ to $R_8$ may be identical with or different from each other; and m+n denotes an integer number of 1 to 10, wherein the layer containing the compound represented by the general formula [1] contains at least one of the compounds represented by the following general formula [6]:

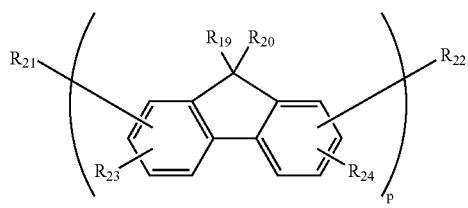

(wherein $R_{19}$ and $R_{20}$ represent groups respectively selected from the group consisting of a hydrogen atom, and substituted or unsubstituted alkyl group, aralkyl group, and aryl group, in which the $R_{19}$ groups or the $R_{20}$ groups bonded with different fluorene groups may be identical with or different from each other, and $R_{19}$ and $R_{20}$ bonded with the same fluorene group may be identical with or different from each other; and $R_{21}$ to $R_{24}$ represent groups respectively selected from the group consisting of a hydrogen atom, a halogen group, substituted or unsubstituted alkyl group, aralkyl group, and alkoxy group, a substituted silyl group, and a cyano group; and p is an integer number of 2 to 10).

6. An organic luminescence device according to claim 1, wherein the layer containing the compound represented by the general formula [1] is provided as a luminescent layer.

7. An organic luminescence device according to claim 2, wherein the layer containing the compound represented by the general formula [1] is provided as a luminescent layer.

8. An organic luminescence device according to claim 3, wherein the layer containing the compound represented by the general formula [1] is provided as a luminescent layer.

9. An organic luminescence device according to claim 4, wherein the layer containing the compound represented by the general formula [1] is provided as a luminescent layer.

10. An organic luminescence device according to claim 5, wherein the layer containing the compound represented by the general formula [1] is provided as a luminescent layer.

* * * * *

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

ON COVER PAGE AT (56) FOREIGN PATENT DOCUMENTS

"2002-8866 1/2000" should read --2002-8866 1/2002--; "2000-5069166" should read --2000-506916--; "504794 A1" should read --0 504 794 A1--; and "0918259 A1" should read --0 918 259 A1--.

ON COVER PAGE AT (57) ABSTRACT

Line 8, " 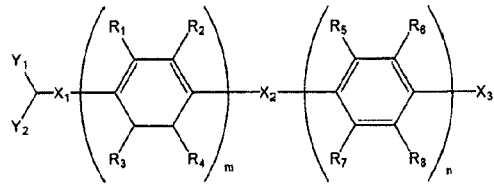 " should read

-- 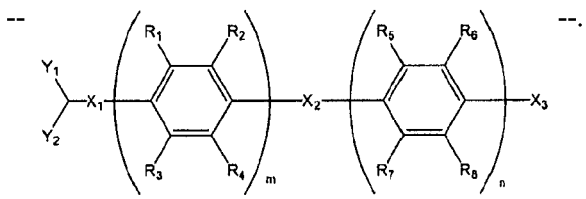 --.

COLUMN 1

Line 9, "filed" should read --field--.

UNITED STATES PATENT AND TRADEMARK OFFICE
CERTIFICATE OF CORRECTION

PATENT NO.       : 7,387,845 B2
APPLICATION NO.  : 10/525622
DATED            : June 17, 2008
INVENTOR(S)      : Akihito Saitoh et al.

It is certified that error appears in the above-identified patent and that said Letters Patent is hereby corrected as shown below:

COLUMN 2

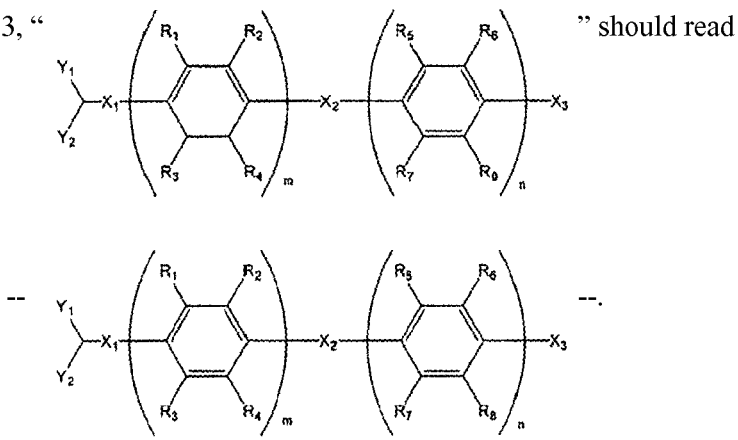

Line 33, " " should read -- --.

COLUMN 3

Line 49, "[I]." should read --[1].--.

COLUMN 4

Line 49, "tylene" should read --thylene--.

COLUMN 5

Line 19, "include" should read --included--.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 27

Line 63, "described" should read --described in--.

COLUMN 30

Line 65, "followings" should read --following--.

COLUMN 31

Compound [2]-2, " 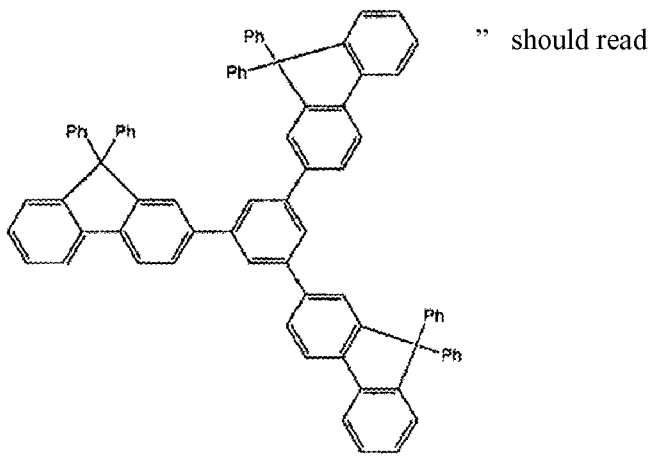 " should read

UNITED STATES PATENT AND TRADEMARK OFFICE
CERTIFICATE OF CORRECTION

PATENT NO. : 7,387,845 B2 Page 4 of 33
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

-- 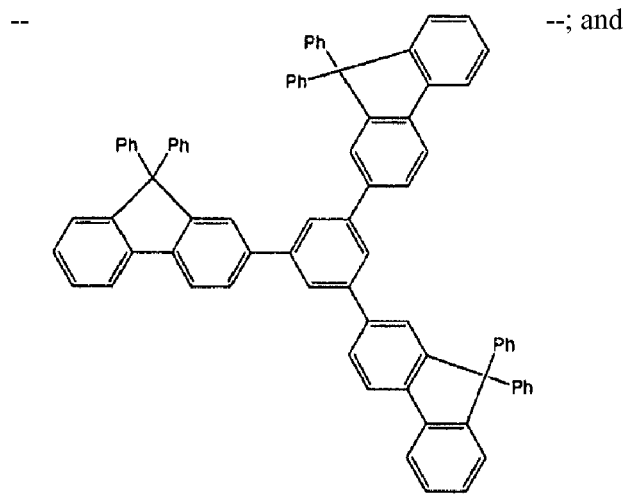 --; and

Compound [2]-4, " 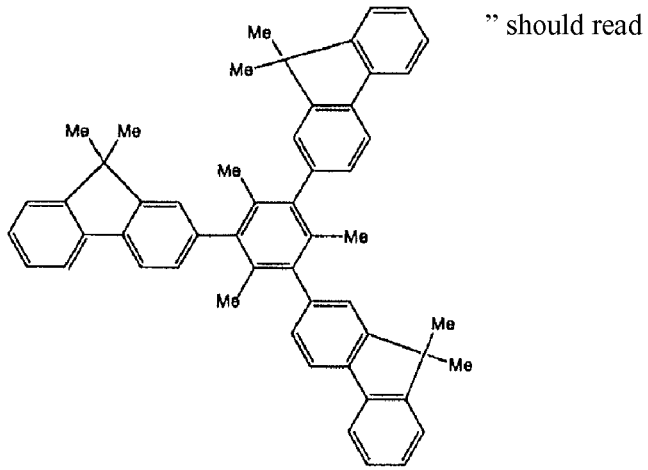 " should read

UNITED STATES PATENT AND TRADEMARK OFFICE
CERTIFICATE OF CORRECTION

PATENT NO.       : 7,387,845 B2
APPLICATION NO. : 10/525622
DATED            : June 17, 2008
INVENTOR(S)      : Akihito Saitoh et al.

It is certified that error appears in the above-identified patent and that said Letters Patent is hereby corrected as shown below:

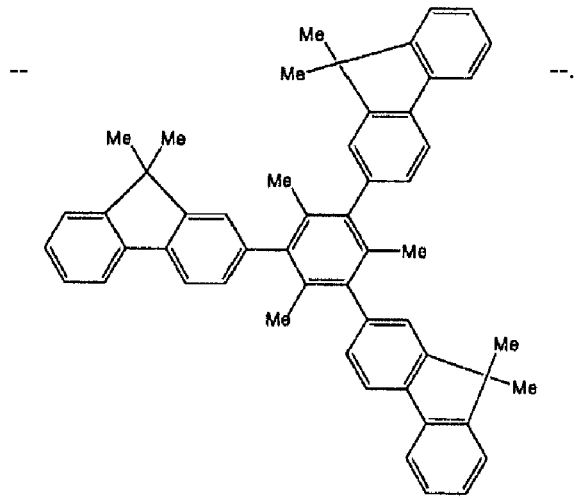

COLUMN 32

Compound [2]-1, " 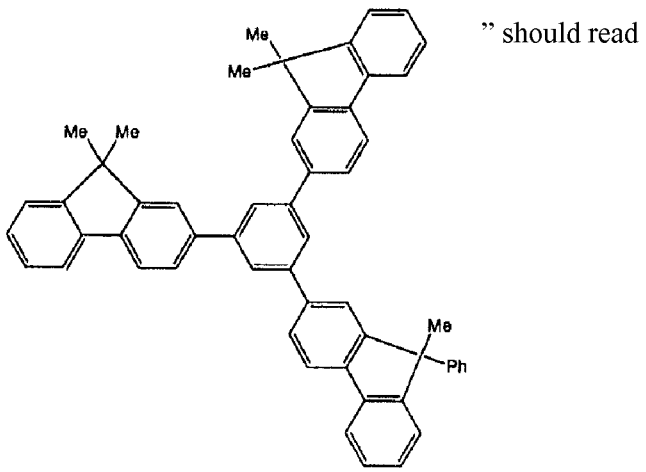 " should read

UNITED STATES PATENT AND TRADEMARK OFFICE
CERTIFICATE OF CORRECTION

PATENT NO.      : 7,387,845 B2
APPLICATION NO. : 10/525622
DATED           : June 17, 2008
INVENTOR(S)     : Akihito Saitoh et al.

It is certified that error appears in the above-identified patent and that said Letters Patent is hereby corrected as shown below:

Compound [2]-3, " 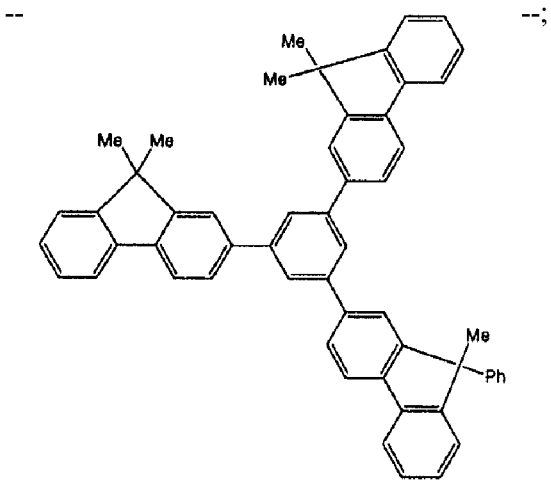 " should read -- 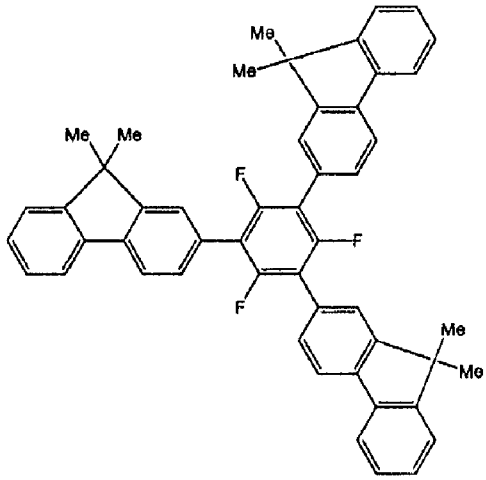 --;

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

-- 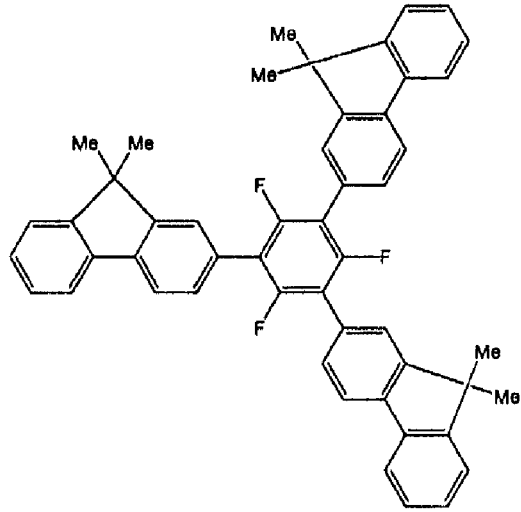 --; and

Compound [2]-5, " 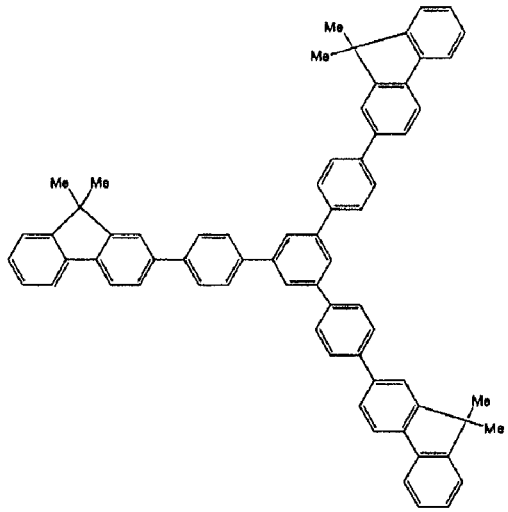 " should read

UNITED STATES PATENT AND TRADEMARK OFFICE
CERTIFICATE OF CORRECTION

| | | |
|---|---|---|
| PATENT NO. | : 7,387,845 B2 | |
| APPLICATION NO. | : 10/525622 | |
| DATED | : June 17, 2008 | |
| INVENTOR(S) | : Akihito Saitoh et al. | |

It is certified that error appears in the above-identified patent and that said Letters Patent is hereby corrected as shown below:

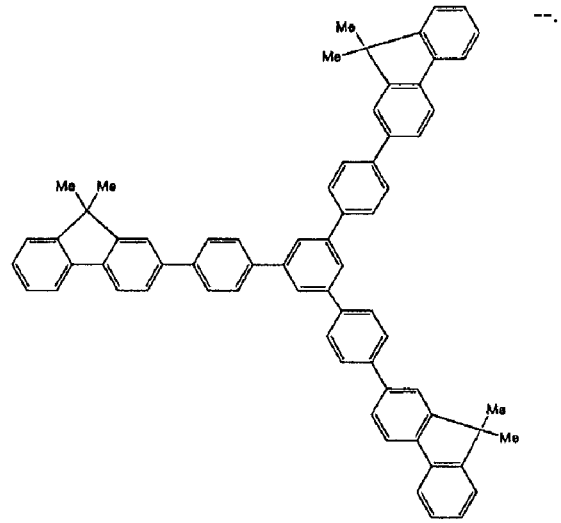

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMNS 33-34

Compound [2]-6, " 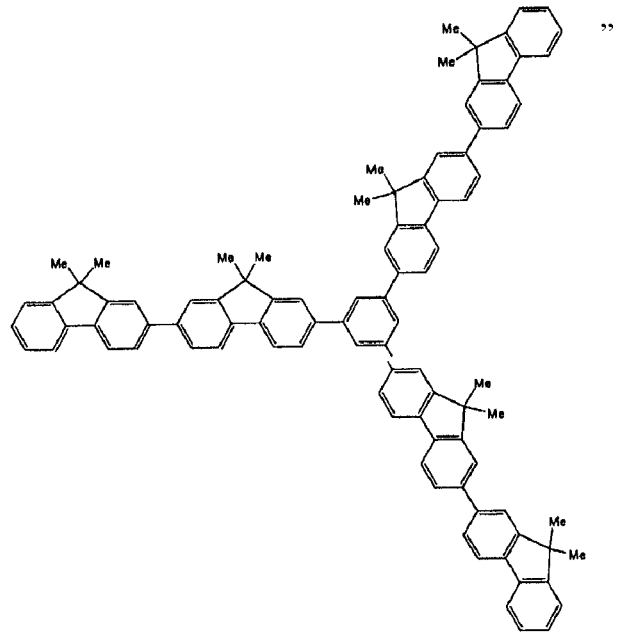 "

should read

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

-- 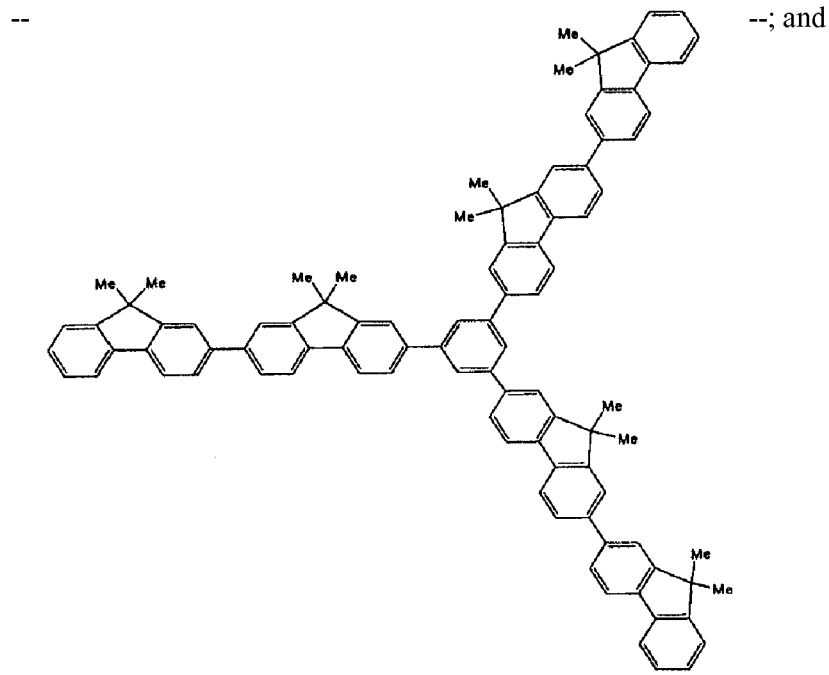 --; and

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

Compound [2]-7, "
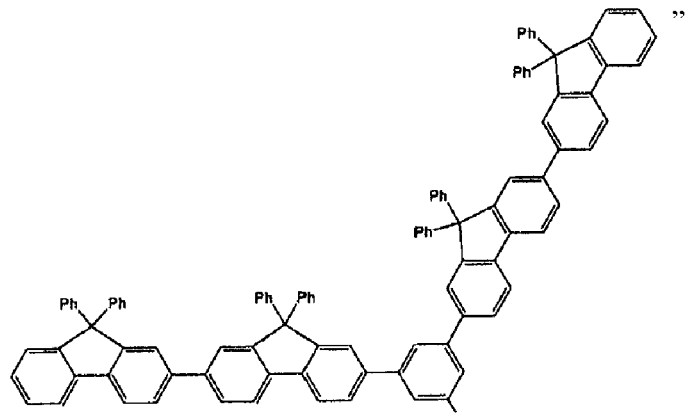
"

should read

--
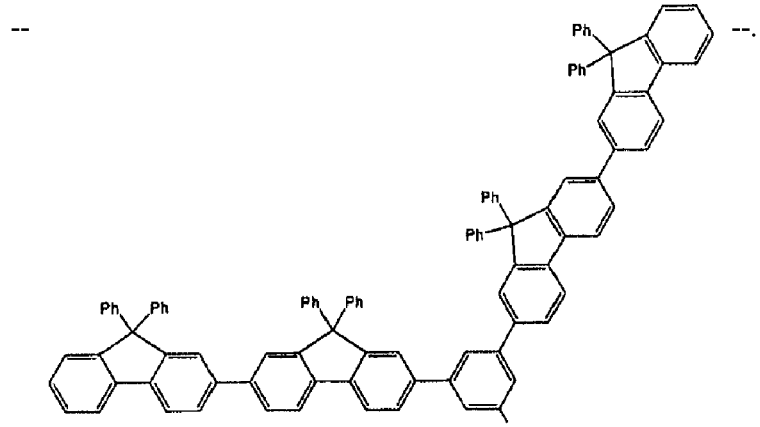
--.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 37

Compound [2]-12, " 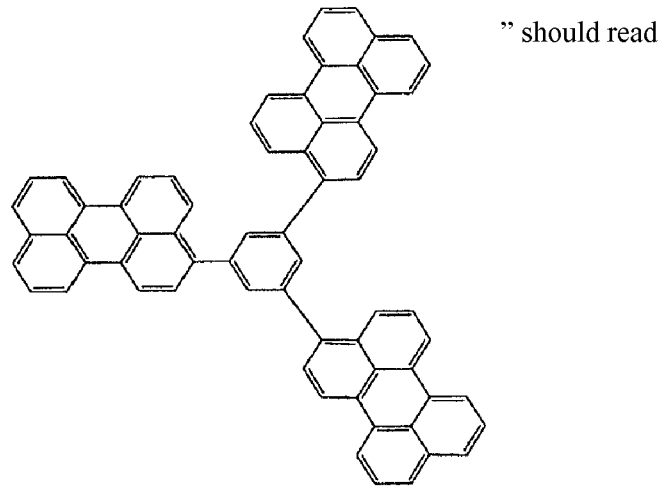 " should read

-- 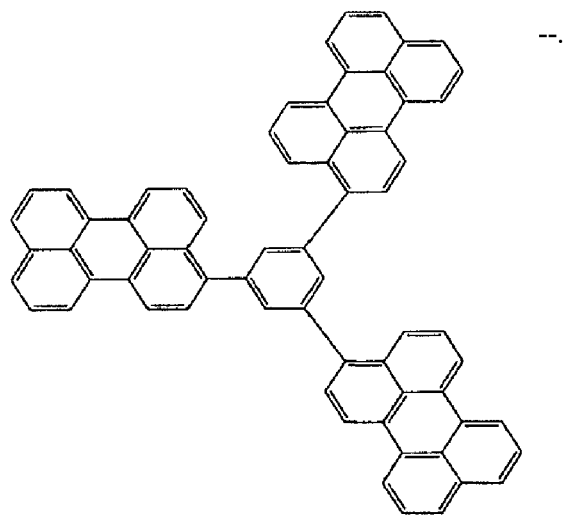 --.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 38

Compound [2]-13, " 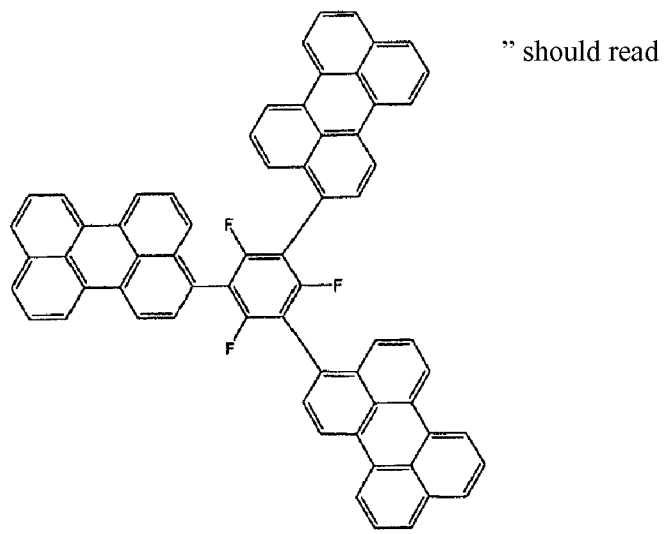 " should read

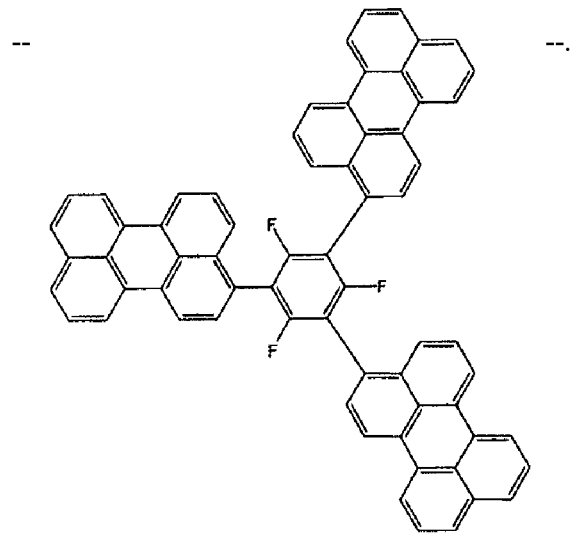

-- --.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 39

Compound [2]-14, " 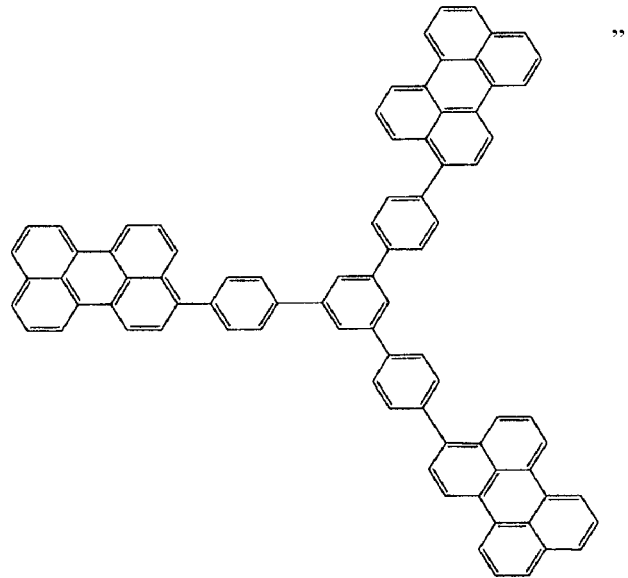 "

should read

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

-- 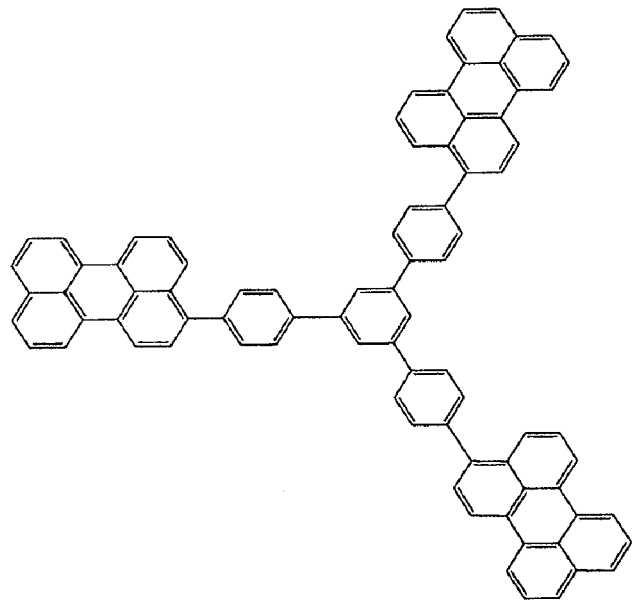 --.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 45

Compound [3]-11, " 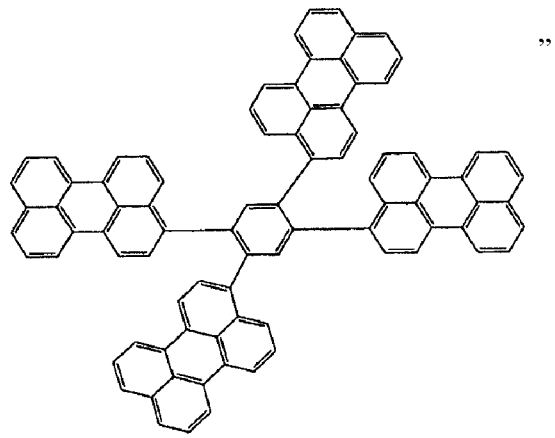 "

should read

-- 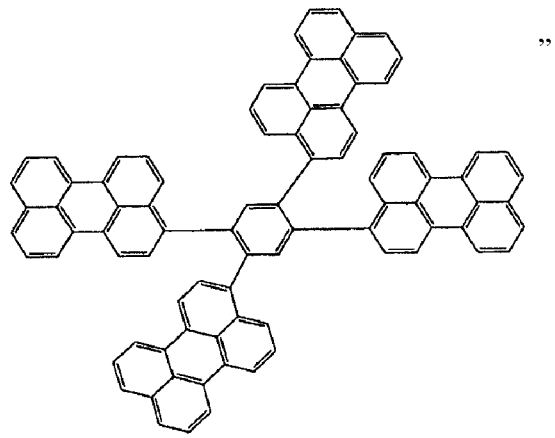 --.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 46

Compound [3]-12, " 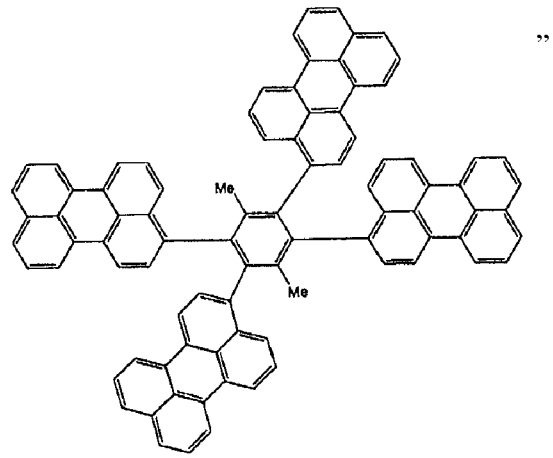 "

should read

-- 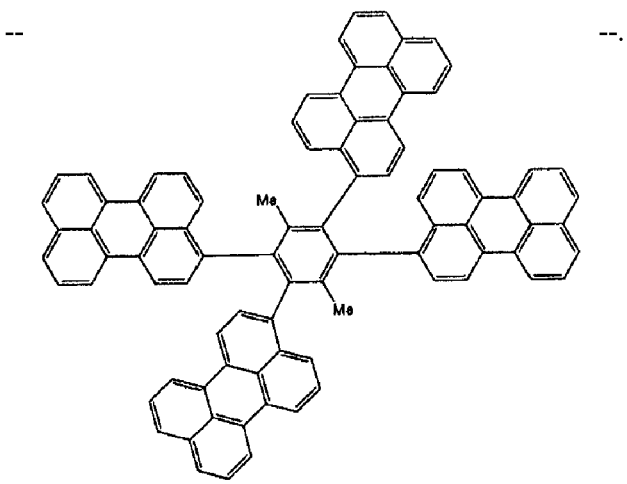 --.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 47

Compound [3]-13, " 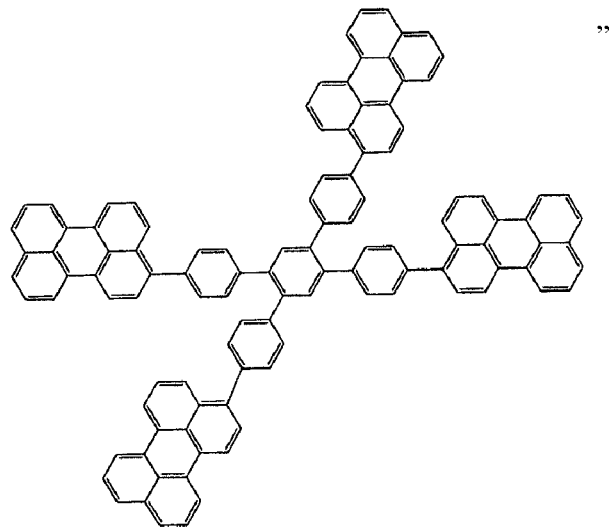 "

should read

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

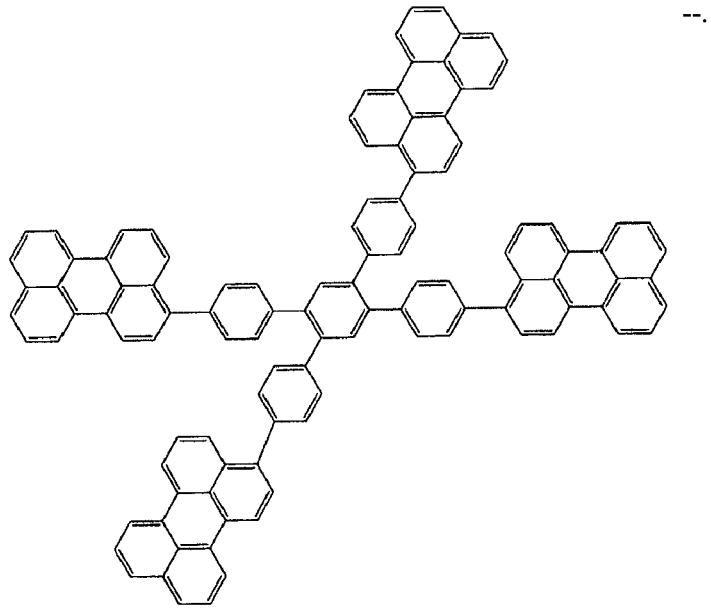

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 53

Compound [4]-6,

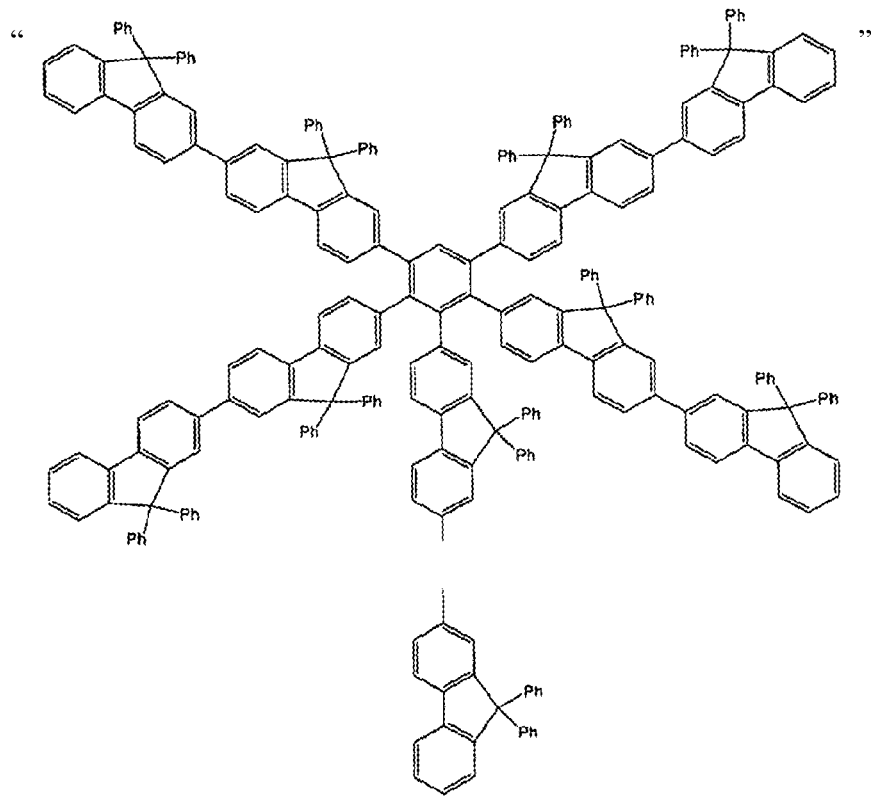

should read

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

-- 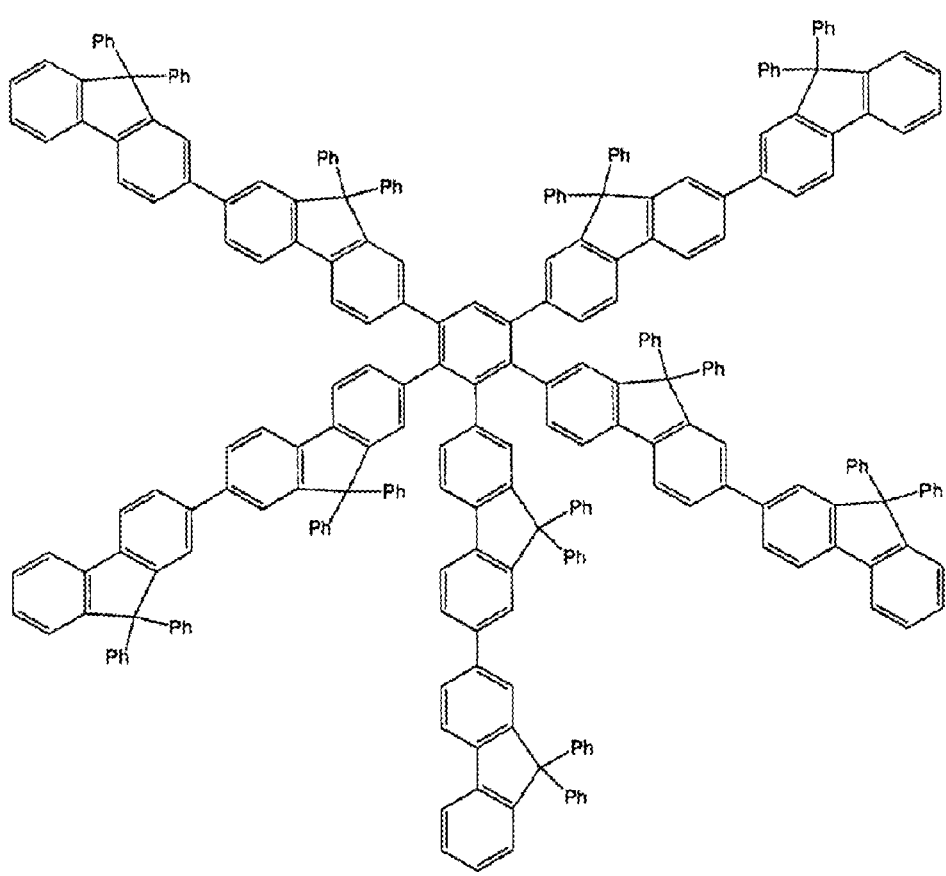 --.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 57

Compound [4]-11,

"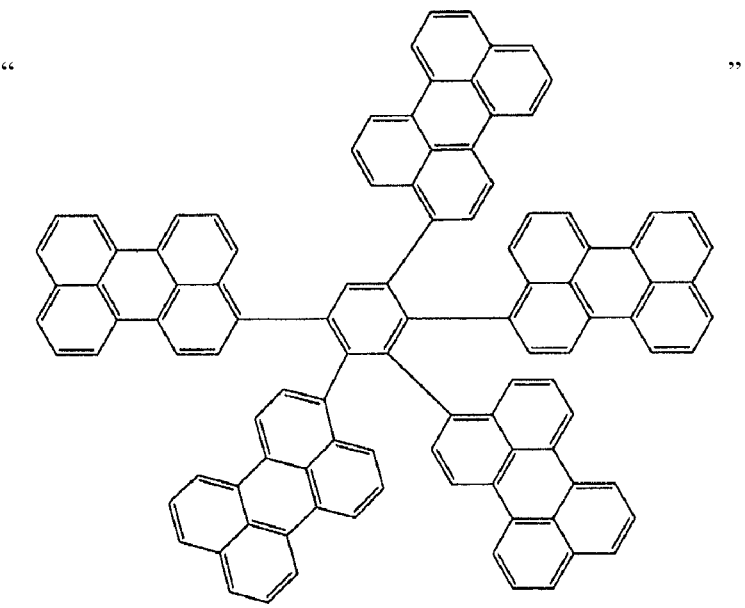"

should read

UNITED STATES PATENT AND TRADEMARK OFFICE
CERTIFICATE OF CORRECTION

PATENT NO. : 7,387,845 B2  
APPLICATION NO. : 10/525622  
DATED : June 17, 2008  
INVENTOR(S) : Akihito Saitoh et al.

Page 23 of 33

It is certified that error appears in the above-identified patent and that said Letters Patent is hereby corrected as shown below:

-- 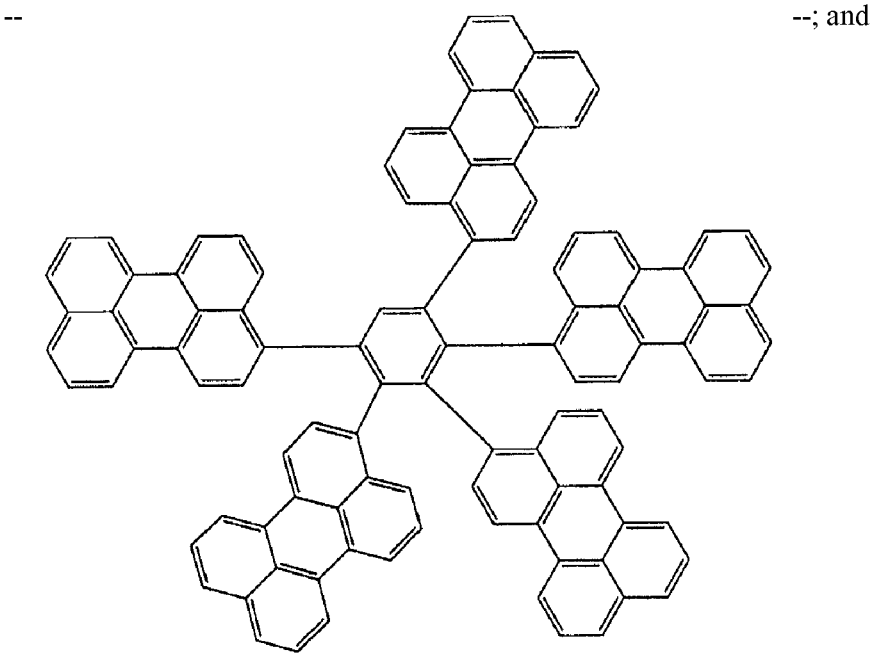 --; and

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

Compound [4]-13,

"

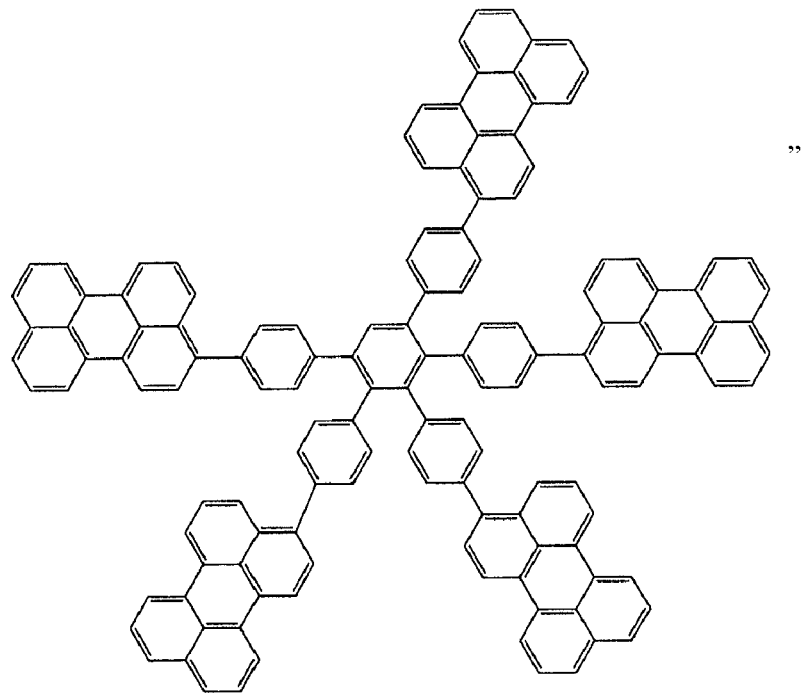

"

should read

UNITED STATES PATENT AND TRADEMARK OFFICE
CERTIFICATE OF CORRECTION

PATENT NO.         : 7,387,845 B2                                Page 25 of 33
APPLICATION NO.    : 10/525622
DATED              : June 17, 2008
INVENTOR(S)        : Akihito Saitoh et al.

It is certified that error appears in the above-identified patent and that said Letters Patent is hereby corrected as shown below:

-- 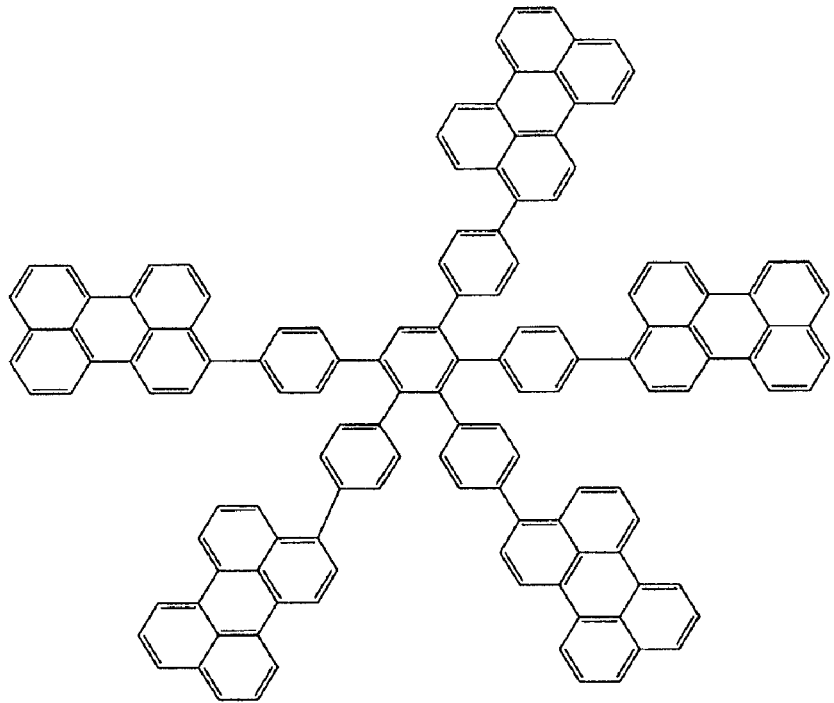 --.

UNITED STATES PATENT AND TRADEMARK OFFICE
CERTIFICATE OF CORRECTION

PATENT NO.       : 7,387,845 B2
APPLICATION NO.  : 10/525622
DATED            : June 17, 2008
INVENTOR(S)      : Akihito Saitoh et al.

It is certified that error appears in the above-identified patent and that said Letters Patent is hereby corrected as shown below:

COLUMN 58

Compound [4]-12,

"

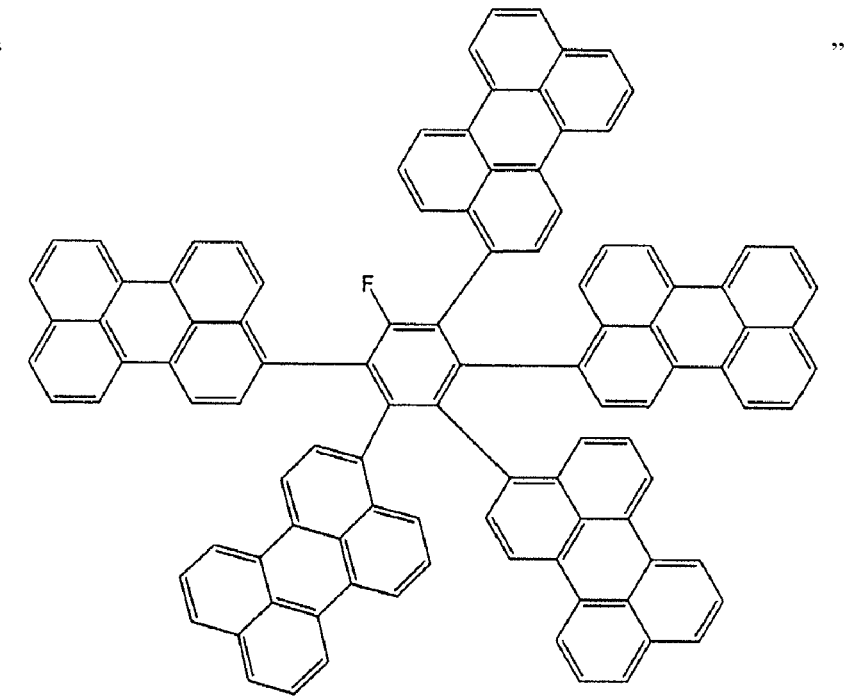

"

should read

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

-- 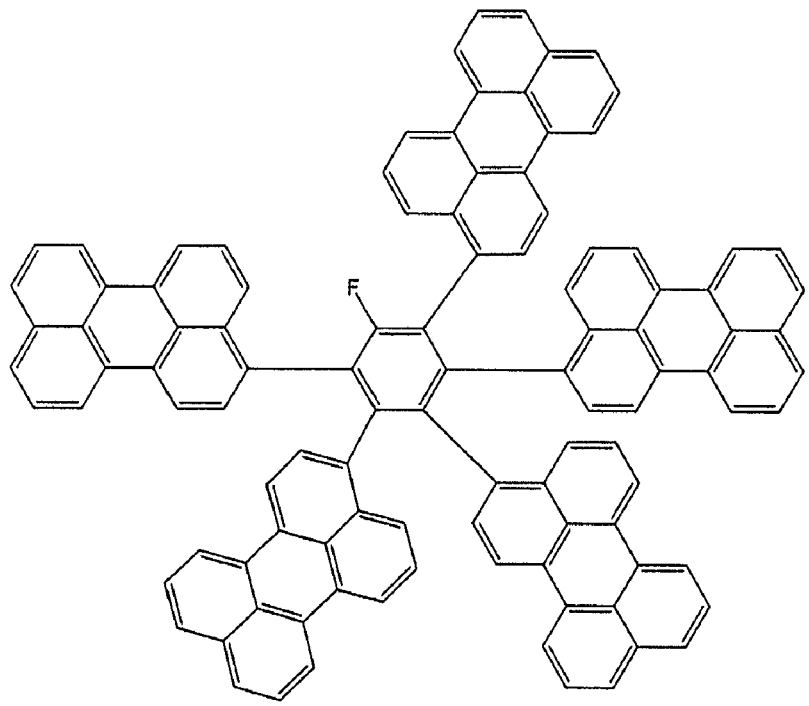 --.

UNITED STATES PATENT AND TRADEMARK OFFICE
CERTIFICATE OF CORRECTION

PATENT NO.       : 7,387,845 B2
APPLICATION NO.  : 10/525622
DATED            : June 17, 2008
INVENTOR(S)      : Akihito Saitoh et al.

It is certified that error appears in the above-identified patent and that said Letters Patent is hereby corrected as shown below:

COLUMN 67-68

Compound [5]-13,

"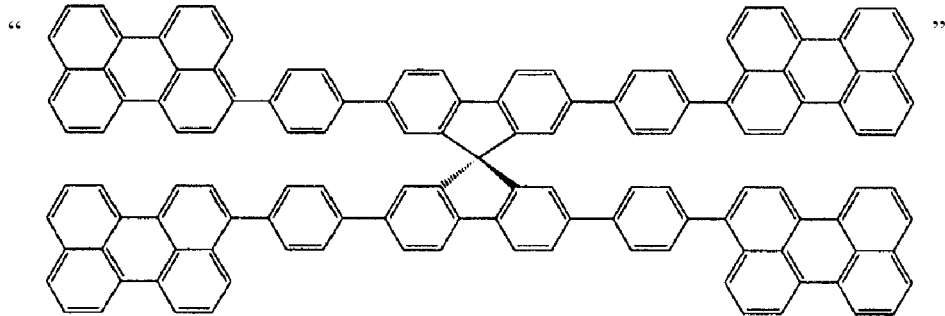"

should read

--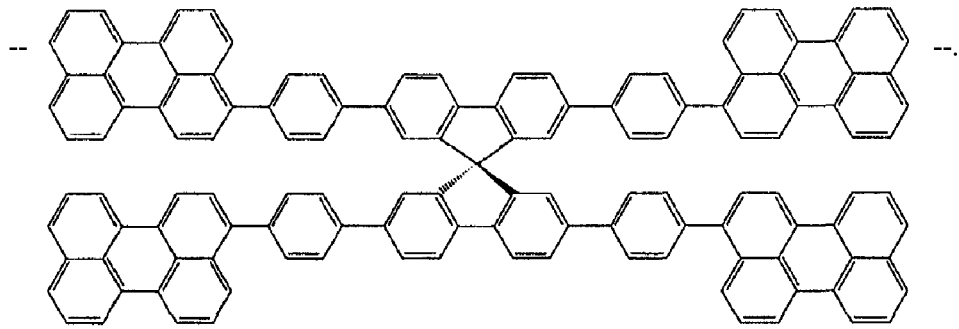--.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 68

Compound [5]-12,

" 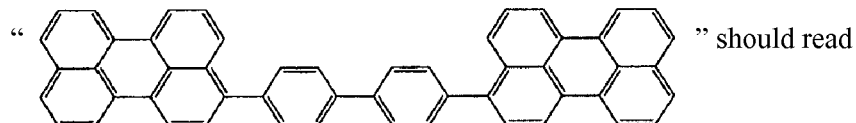 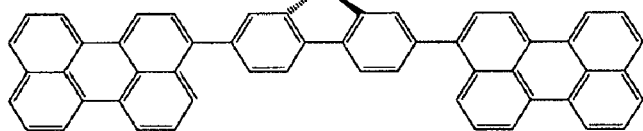 " should read

-- 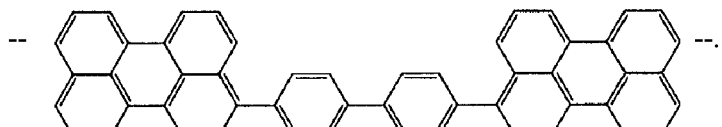 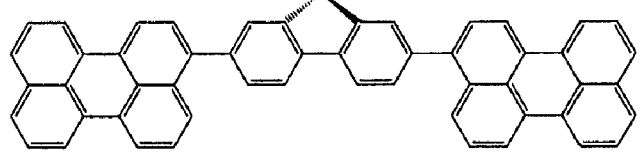 --.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 72

Compound PcM, " 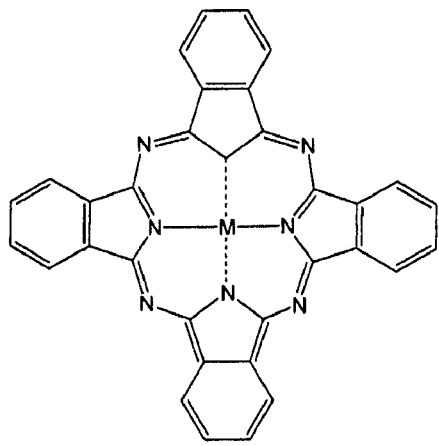 " should read

-- 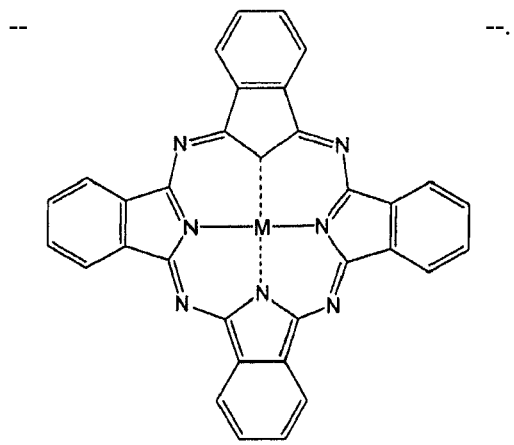 --.

UNITED STATES PATENT AND TRADEMARK OFFICE
CERTIFICATE OF CORRECTION

PATENT NO.       : 7,387,845 B2
APPLICATION NO.  : 10/525622
DATED            : June 17, 2008
INVENTOR(S)      : Akihito Saitoh et al.

It is certified that error appears in the above-identified patent and that said Letters Patent is hereby corrected as shown below:

COLUMN 79

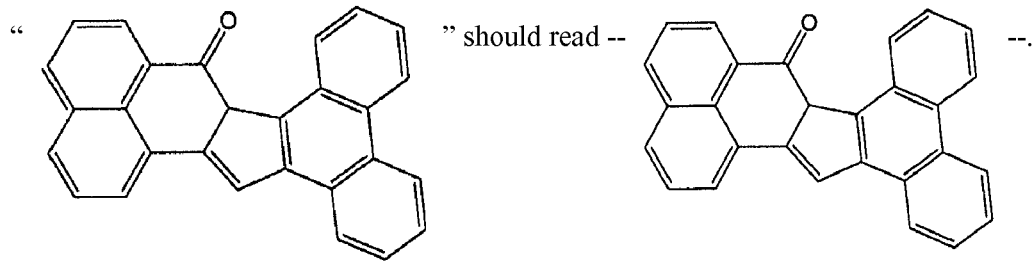

COLUMN 80

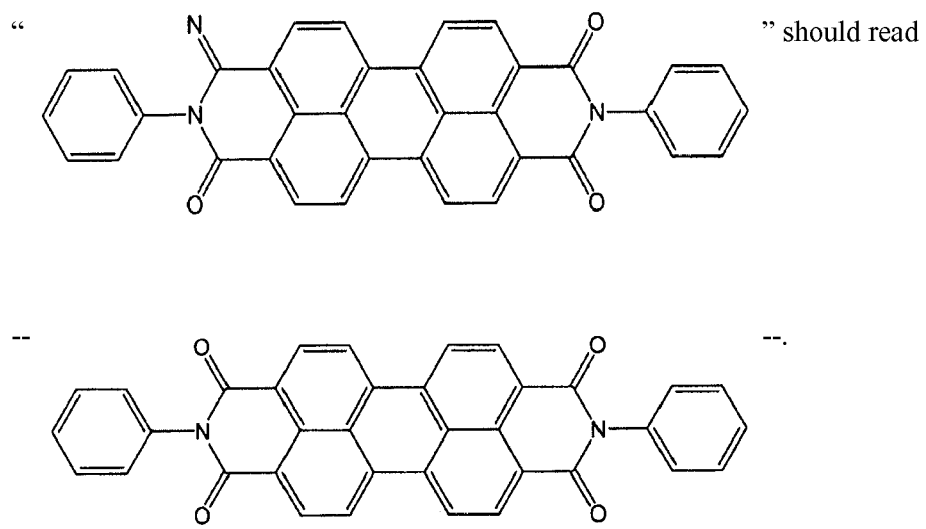

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 83

Line 14, "Poly thiophene" should read --Polythiophene--.

COLUMN 85

Line 4, "[1]-38]" should read --[1]-38--.

COLUMN 86

Line 50, "[1]-109]" should read --[1]-109--.

COLUMN 90

Line 21, "in stead" should read --instead--;
Table 9, "Examplified" should read --Exemplified--;
Line 54, "in" should read --instead--; and
Line 55, "stead" should be deleted.

COLUMN 91

Line 16, "in stead" should read --instead--.

COLUMN 94

Line 56, "substituted" should read --substituted or--.

UNITED STATES PATENT AND TRADEMARK OFFICE
CERTIFICATE OF CORRECTION

PATENT NO. : 7,387,845 B2
APPLICATION NO. : 10/525622
DATED : June 17, 2008
INVENTOR(S) : Akihito Saitoh et al.

It is certified that error appears in the above-identified patent and that said Letters Patent is hereby corrected as shown below:

COLUMN 96

Line 10, "substituted" should read --substituted or--.

COLUMN 97

Line 28, "substituted" should read --substituted or--.

COLUMN 100

Line 10, "substituted" should read --substituted or--.

Signed and Sealed this

Ninth Day of December, 2008

JON W. DUDAS
*Director of the United States Patent and Trademark Office*